(12) United States Patent
Umeda et al.

(10) Patent No.: US 9,343,686 B2
(45) Date of Patent: May 17, 2016

(54) COMPOUND, SOLAR CELL MODULE, AND SOLAR POWER GENERATION DEVICE

(71) Applicant: Sharp Kabushiki Kaisha, Osaka-shi, Osaka (JP)

(72) Inventors: Tokiyoshi Umeda, Osaka (JP); Daisuke Tsukio, Osaka (JP); Yukio Takenaka, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 14/412,014

(22) PCT Filed: May 20, 2013

(86) PCT No.: PCT/JP2013/063948
§ 371 (c)(1),
(2) Date: Dec. 30, 2014

(87) PCT Pub. No.: WO2014/010305
PCT Pub. Date: Jan. 16, 2014

(65) Prior Publication Data
US 2015/0162547 A1    Jun. 11, 2015

(30) Foreign Application Priority Data

Jul. 9, 2012    (JP) .................................. 2012-153975
Aug. 13, 2012  (JP) .................................. 2012-179567

(51) Int. Cl.
*C07D 471/22*     (2006.01)
*H01L 31/00*      (2006.01)
*H01L 51/00*      (2006.01)
*H01L 31/055*     (2014.01)
*H01L 31/054*     (2014.01)
*H01L 51/44*      (2006.01)

(52) U.S. Cl.
CPC .......... *H01L 51/0072* (2013.01); *C07D 471/22* (2013.01); *H01L 31/055* (2013.01); *H01L 31/0547* (2014.12); *H01L 51/0053* (2013.01); *H01L 51/447* (2013.01); *Y02E 10/52* (2013.01)

(58) Field of Classification Search
USPC ...................................... 546/27; 136/263, 252
See application file for complete search history.

(56) References Cited

U.S. PATENT DOCUMENTS 8,299,354 B2 * 10/2012 Bhaumik ............. C07D 471/22
                                                  136/257

FOREIGN PATENT DOCUMENTS

JP    03-273686 A    12/1991

OTHER PUBLICATIONS

Quante et al., "Synthesis of Soluble Perylenebisamidine Derivatives. Novel Long-Wavelength Absorbing and Fluorescent Dyes," Chem. Mater., vol. 9, 1997, pp. 495-500.
Debije et al., "Promising Fluorescent Dye for Solar Energy Conversion Based on a Perylene Perinone," Applied Optics, vol. 50, No. 2, Jan. 10, 2011, pp. 163-169.

* cited by examiner

*Primary Examiner* — Charanjit Aulakh
(74) *Attorney, Agent, or Firm* — Keating & Bennett, LLP

(57) ABSTRACT

A compound is represented by the following general formula (IA0) or (IB0). A solar cell module for which the compound is used is used for a solar power generation device.

10 Claims, 20 Drawing Sheets

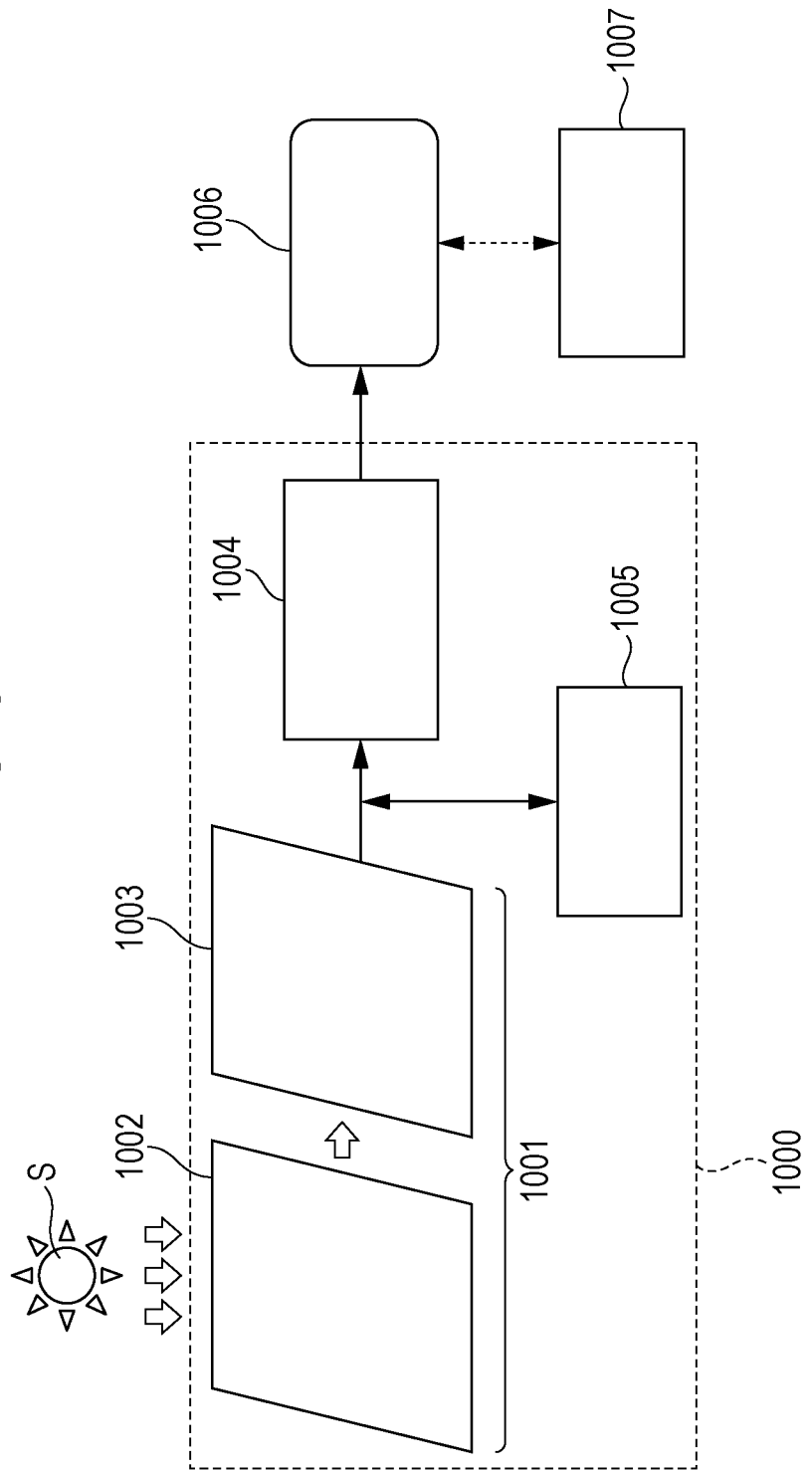

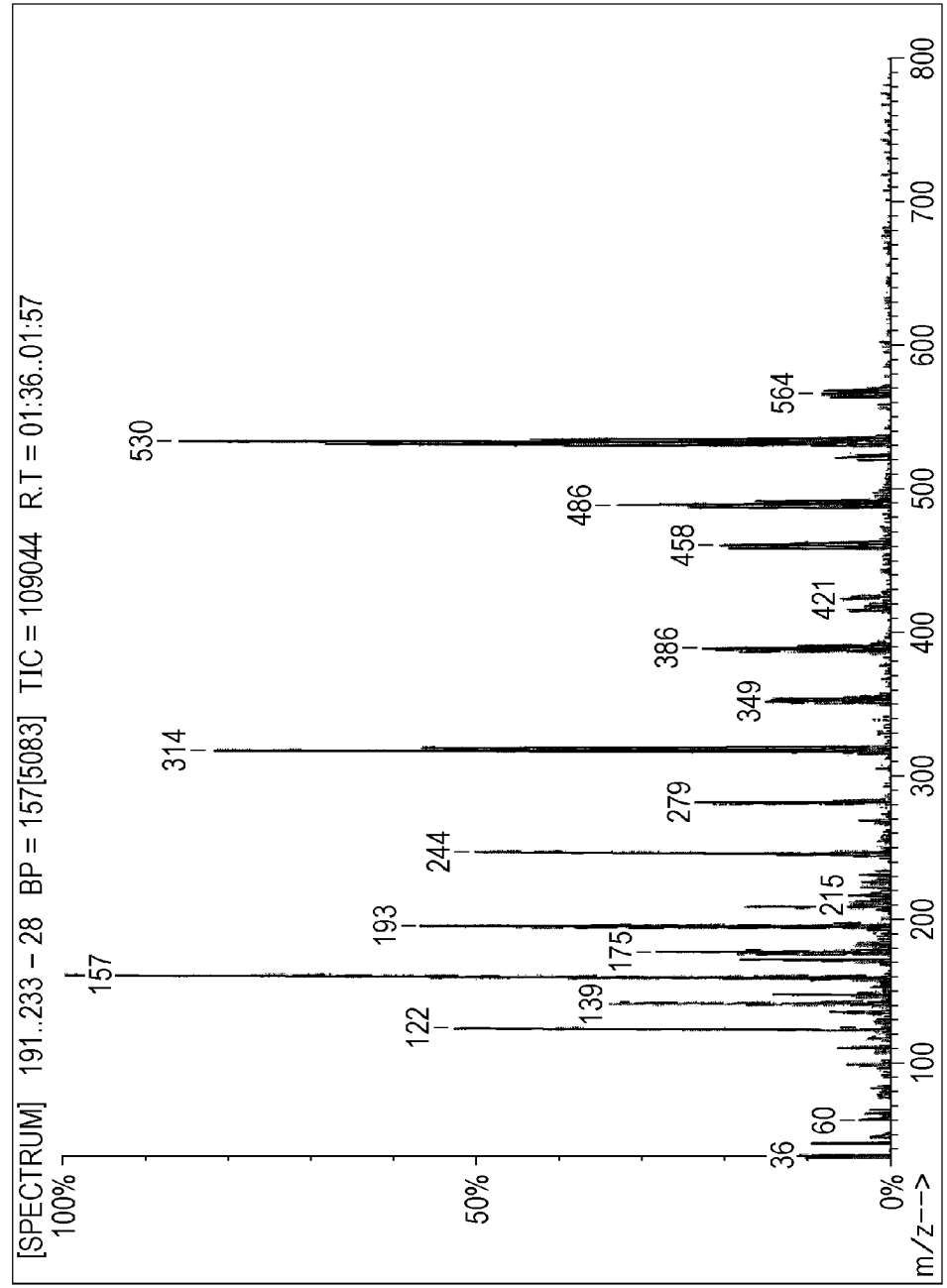

COMPOUND, SOLAR CELL MODULE, AND SOLAR POWER GENERATION DEVICE

TECHNICAL FIELD

The present invention relates to a novel compound, a solar cell module which uses the compound, and a solar power generation device which includes the solar cell module.

This patent application claims the benefit of priority of Japanese Patent Application No. 2012-153975 filed in Japan on Jul. 9, 2012 and Japanese Patent Application No. 2012-179567 filed in Japan on Aug. 13, 2012, the contents of which are herein incorporated by reference.

BACKGROUND ART

As a solar power generation device that includes a solar cell element in a portion of a light guide and generates power by allowing light propagating through the inside of the light guide to be incident on the solar cell element, a solar power generation device (solar energy recovery window) described in PTL 1 is known.

The solar power generation device is configured such that some of the solar light incident from a main surface of the light guide is allowed to propagate through the inside of the light guide and to be guided to the solar cell element. The light guide contains a phosphor (fluorescent substance). The phosphor absorbs the solar light (incident light) incident on the light guide and is excited and then emits light. Power is generated by radiation light (fluorescence) from the phosphor at this time propagating through the inside of the light guide and being incident on the solar cell element.

In such a solar power generation device, the light emitting capability of the phosphor may be a factor that determines the power generation amount. Further, in order to increase the power generation amount of the solar power generation device, it is desirable that a phosphor capable of absorbing light having a sufficiently long wavelength is used, that is, it is important to select an appropriate phosphor.

Various kinds of materials have been investigated as a phosphor so far, and, for example, a compound represented by the following formula (9)-1 (hereinafter, simply written as the "compound (9)-1") is disclosed in NPLs 1 and 2.

[Chem. 1]

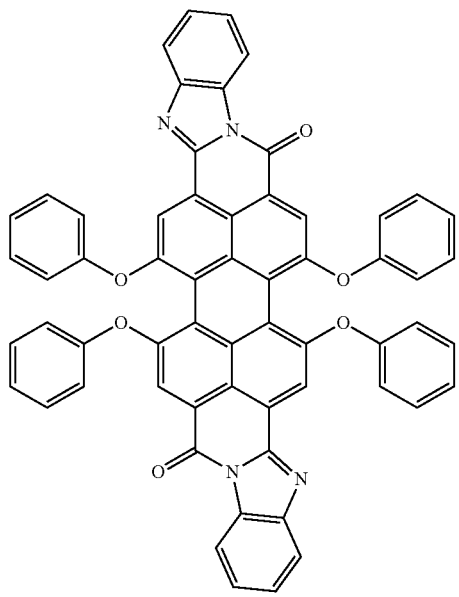

(9)-1

CITATION LIST

Patent Literature

PTL 1: Japanese Unexamined Patent Application Publication No. 3-273686

Non Patent Literature

NPL 1: Michael G. Debije, et al., Appl. Opt., 50(2011)163
NPL 2: Heribert Quante, et al., Chem. Mater., 1997, 9, 495

SUMMARY OF INVENTION

Technical Problem

However, the peak wavelength of absorbable light (light absorption peak wavelength) for the compound (9)-1 is approximately 630 nm, and the value of the absorption wavelength of light is not sufficiently long. In a case where such a compound is used in a solar cell module for a solar power generation device, since it is difficult to expect an increase in the power generation amount of the solar power generation device, application of a novel compound has been desired.

Several aspects of the present invention have been made in consideration of the above-described problem, and provide a novel compound capable of absorbing light having a sufficiently long wavelength, a solar cell module using the compound, and a solar power generation device including the solar cell module.

Solution to Problem

According to an aspect of the present invention, a compound represented by the following general formula (IA0) or (IB0) is provided.

[Chem. 2]

(IA0)

-continued (IBO)

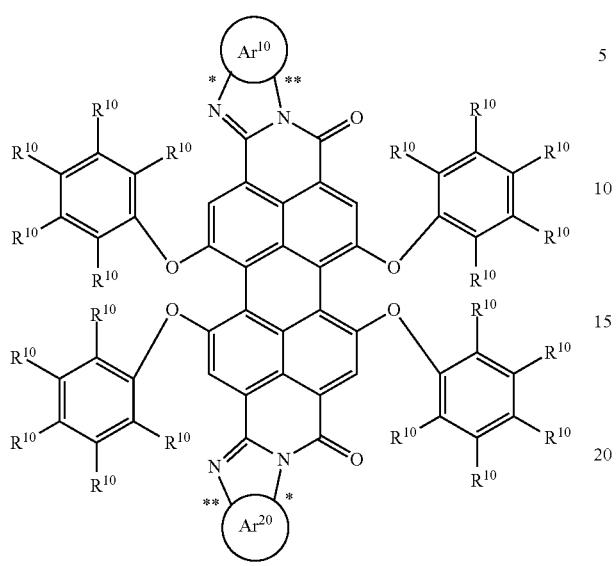

(In the formulae, $R^{10}$ represents a hydrogen atom, an alkyl group, an alkenyl group, an alkynyl group, an aryl group, an alkyl carbonyl amino group, or a group represented by the following general formula (z)-10 or (z)-20, and a plurality of Zs may be the same as or different from one another; $Ar^{10}$ and $Ar^{20}$ each independently represent a group represented by the following general formula (I)-110, (I)-120, (I)-130, (I)-210, or (I)-220; $R^{10}$ represents a hydrogen atom or an alkyl group when $Ar^1$ and $Ar^2$ each independently represent a group represented by the following general formula (I)-210 or (I)-220; a bond marked with a symbol "*" is attached to a carbon atom marked with the symbol "*" of the group, and a bond marked with a symbol "" is attached to a carbon atom marked with the symbol "" of the group.)

[Chem. 3]

(II)-110

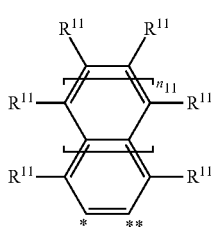

(II)-120

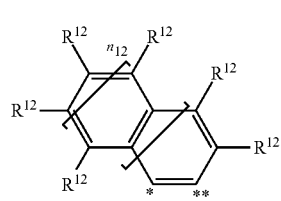

(II)-130

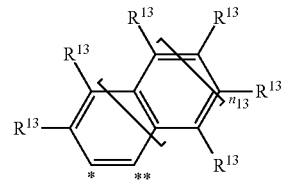

(I)-210

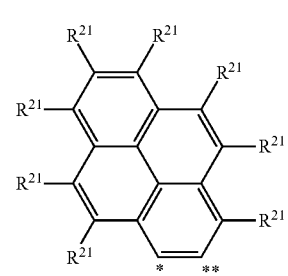

(I)-220

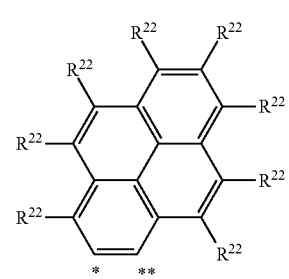

[Chem. 4]

(Z)-10

(Z)-20

(In the formulae, $R^1$ represents a hydrogen atom, an alkyl group, or an aryl group, and two $R^1$s may be the same as or different from each other; $R^2$ represents a hydrogen atom or an alkyl group; $R^{11}$, $R^{12}$, $R^{13}$, $R^{21}$, and $R^{22}$ each independently represent a hydrogen atom or an alkyl group, and a plurality of $R^{11}$s, $R^{12}$s, $R^{13}$s, $R^{21}$s, and $R^{22}$s may be the same as or different from one another; and $n_{11}$ is an integer of 0 to 2, and $n_{11}$ is 1 or 2 when all R10 and R11 represent a hydrogen atom or an alkyl group, $n_{12}$ and $n_{13}$ are each independently 1 or 2, and a plurality of $n_{11}$s, $n_{12}$s, and $n_{13}$s may be the same as or different from one another.)

According to an aspect of the present invention, a compound represented by the following general formula (IA) or (IB) is provided.

[Chem. 5]

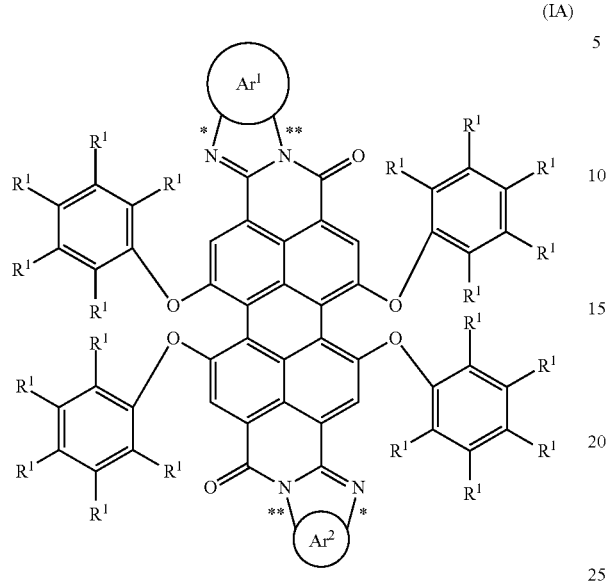

(IA)

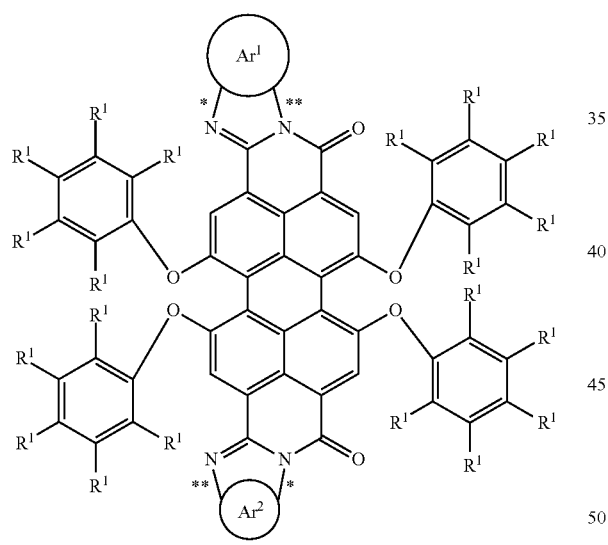

(IB)

(In the formulae, $R^1$ represents a hydrogen atom or an alkyl group, and a plurality of $R^1$s may be the same as or different from one another; $Ar^1$ and $Ar^2$ each independently represent a group represented by the following general formula (I)-11, (I)-12, (I)-13, (I)-21, or (I)-22; and a bond marked with a symbol "*" is attached to a carbon atom marked with the symbol "*" of the group, and a bond marked with a symbol "" is attached to a carbon atom marked with the symbol "" of the group.)

[Chem. 6]

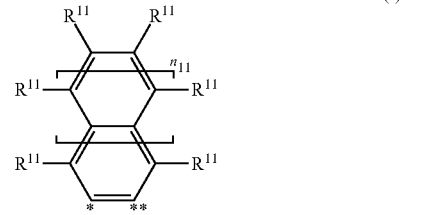

(I)-11

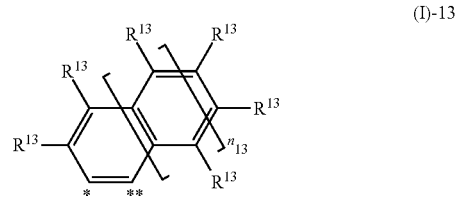

(I)-12

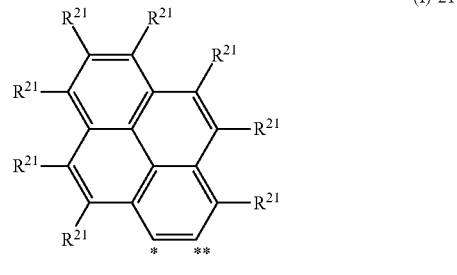

(I)-13

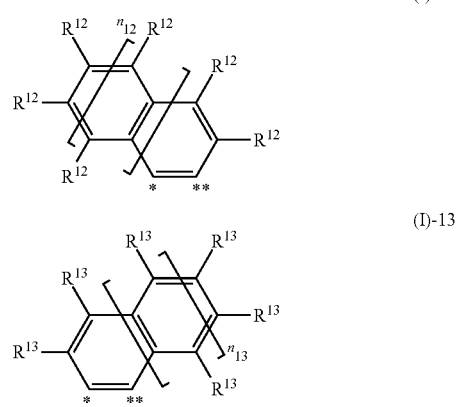

(I)-21

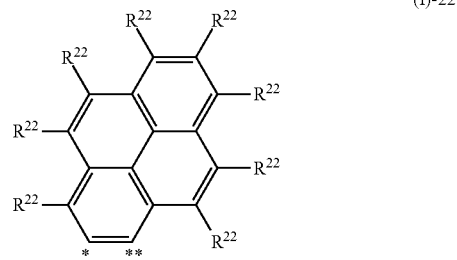

(I)-22

(In the formulae, $R^{11}$, $R^{12}$, $R^{13}$, $R^{21}$, and $R^{22}$ each independently represent a hydrogen atom or an alkyl group, and a plurality of $R^{11}$s, $R^{12}$s, $R^{13}$s, $R^{21}$s, and $R^{22}$s may be the same as or different from one another; and $n_{11}$, $n_{12}$, and $n_{13}$ are each independently 1 or 2, and a plurality of $n_{11}$s, $n_{12}$s, and $n_{13}$s may be the same as or different from one another.)

Further, in the compound according to the aspect of the present invention, $R^1$, $R^{11}$, $R^{12}$, $R^{13}$, $R^{21}$, and $R^{22}$ may each independently represent a hydrogen atom or an alkyl group having 1 to 22 carbon atoms.

Further, in the compound according to the aspect of the present invention, $R^1$, $R^{11}$, $R^{12}$, $R^{13}$, $R^{21}$, and $R^{22}$ may each independently represent a hydrogen atom or an alkyl group having 6 to 18 carbon atoms.

According to another aspect of the present invention, a compound represented by the following general formula (IIA) or (IIB) is provided.

[Chem. 7]

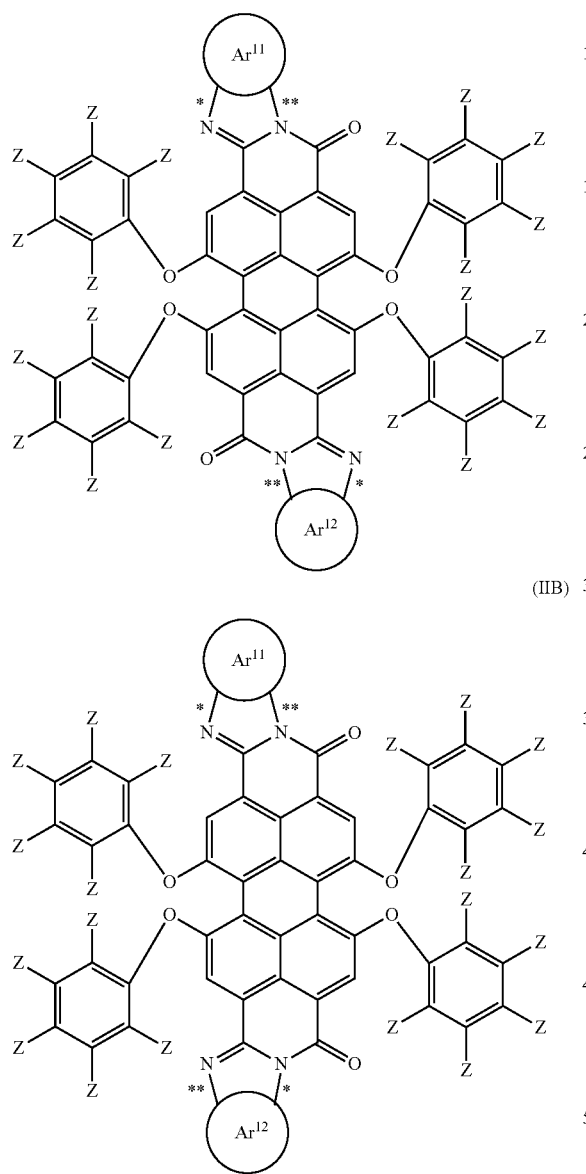

(In the formulae, Z represents a hydrogen atom, an alkyl group, an alkenyl group, an alkynyl group, an aryl group, an alkyl carbonyl amino group, or a group represented by the following general formula (z)-1 or (z)-2, a plurality of Zs may be the same as or different from one another, and, in this case, at least one Z represents an alkenyl group, an alkynyl group, an aryl group, an alkyl carbonyl amino group, or a group represented by the following general formula (z)-1 or (z)-2; $Ar^{11}$ and $Ar^{12}$ each independently represent a group represented by the following general formula (II)-11, (II)-12, or (II)-13; and a bond marked with a symbol "*" is attached to a carbon atom marked with the symbol "*" of the group, and a bond marked with a symbol "" is attached to a carbon atom marked with the symbol "" of the group.)

[Chem. 8]

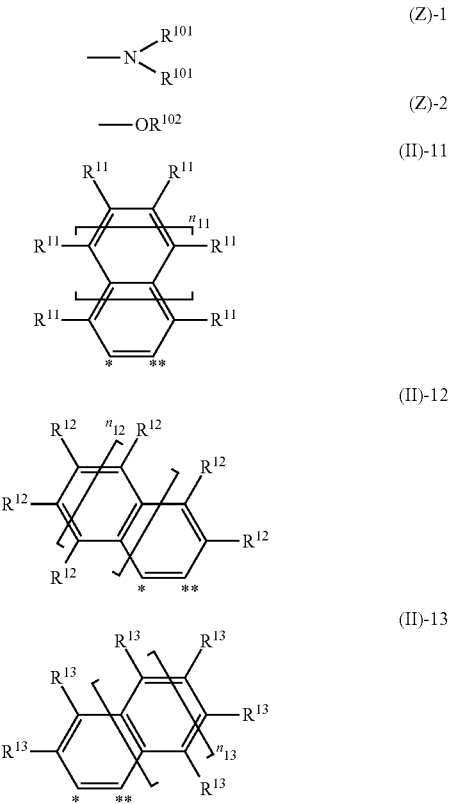

(In the formulae, $R^{101}$ represents a hydrogen atom, an alkyl group, or an aryl group, and two $R^{101}$s may be the same as or different from each other; $R^{102}$ represents a hydrogen atom or an alkyl group; $R^{11}$, $R^{12}$, and $R^{13}$ each independently represent a hydrogen atom or an alkyl group, and a plurality of $R^{11}$s, $R^{12}$s, and $R^{13}$s may be the same as or different from one another; and $n_{11}$ represents an integer of 0 to 2, $n_{12}$ and $n_{13}$ are each independently 1 or 2, and a plurality of $n_{11}$s, $n_{12}$s, and $n_{13}$s may be the same as or different from one another).

In the compound according to another aspect of the present invention, Z may represent a hydrogen atom, an alkyl group having 1 to 22 carbon atoms, or a group represented by the general formula (z)-1 or (z)-2, $R^{101}$ may represent a hydrogen atom, an alkyl group having 1 to 10 carbon atoms, or an aryl group having 6 to 12 carbon atoms, $R^{102}$ may represent an alkyl group having 1 to 10 carbon atoms, and $R^{11}$, $R^{12}$, and $R^{13}$ may each independently represent a hydrogen atom or an alkyl group having 1 to 22 carbon atoms.

Further, in the compound according to the other aspect of the present invention, Z may represent a hydrogen atom, an alkyl group having 6 to 18 carbon atoms, or a group represented by the general formula (z)-1 or (z)-2, and $R^{11}$, $R^{12}$, and $R^{13}$ may each independently represent a hydrogen atom or an alkyl group having 6 to 18 carbon atoms.

Further, according to still another aspect of the present invention, a solar cell module which uses the compound is provided.

Further, the solar cell module according to still another aspect of the present invention includes a light guide which includes a light incident surface and a light emitting surface whose area is smaller than that of the light incident surface; and a solar cell element which receives light emitted from the light emitting surface and generates power, in which the light guide further contains the compound and uses, as the emitted light, radiation light from the compound that is generated by incident light on the light incident surface being absorbed by the compound.

Further, according to still another aspect of the present invention, a solar power generation device including the solar cell module is provided.

Advantageous Effects of Invention

According to the aspects of the present invention, a novel compound capable of absorbing light having a sufficiently long wavelength, a solar cell module using the compound, and a solar power generation device including the solar cell module are provided.

BRIEF DESCRIPTION OF DRAWINGS

FIG. 6 is a view schematically illustrating a configuration of a solar power generation device according to an embodiment of the present invention.

FIG. 7 is a diagram illustrating results of mass analysis of a product of a reaction formula (1-11) of Example 7.

DESCRIPTION OF EMBODIMENTS

Compound

Figure 1:
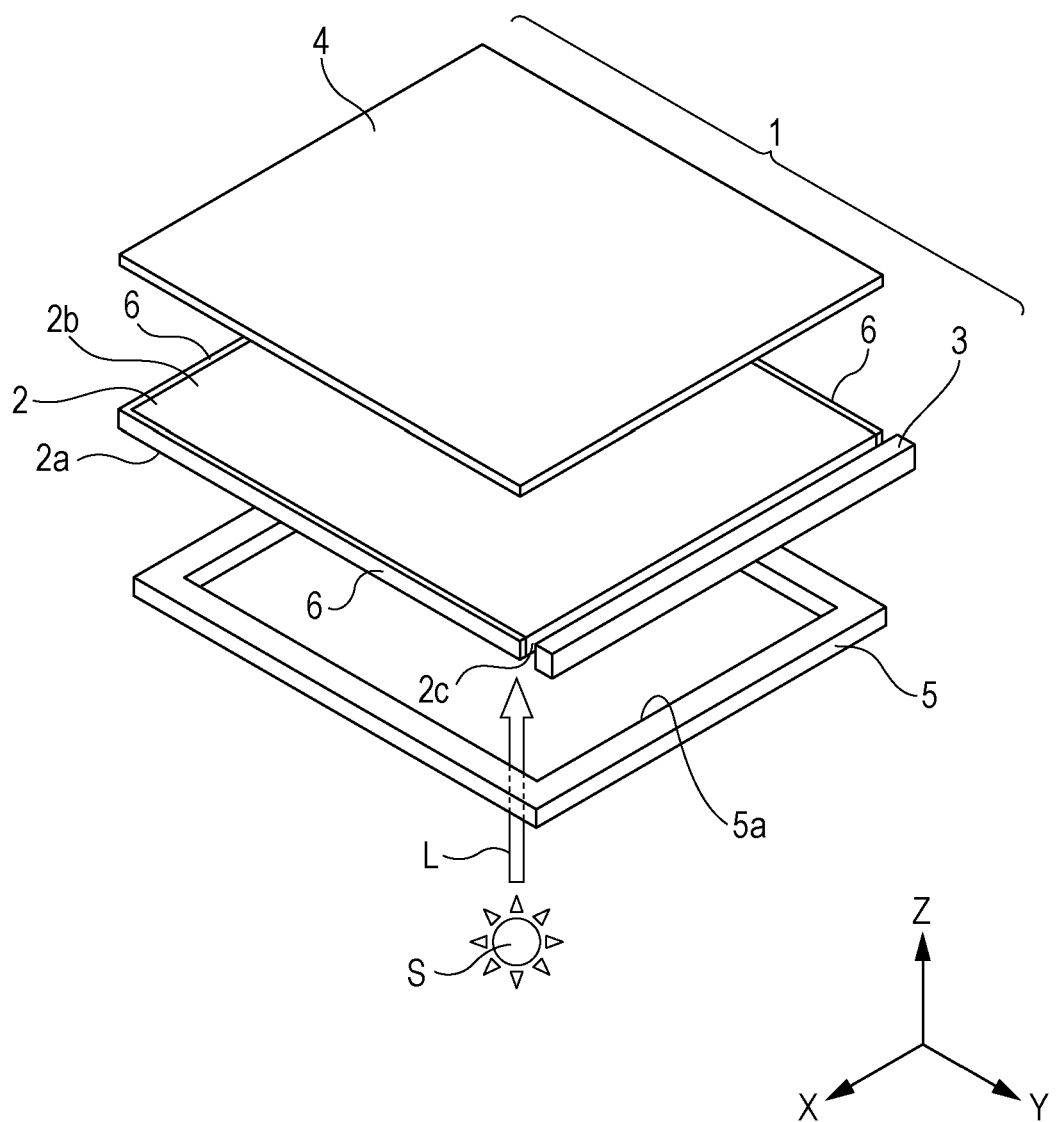
FIG. 1 is a view schematically illustrating a configuration of a solar cell module according to an embodiment of the present invention.

A compound according to the present embodiment is represented by the following general formula (IA0) or (IB0) (hereinafter, these compounds are also simply written as compounds (I0) collectively in some cases). Since the compounds (I0) are novel fluorescent compounds and have a high absorption coefficient with respect to light having a long wavelength, such light can be sufficiently absorbed by the compounds. Among the compounds (I0), the compound represented by the following general formula (IA0) is a syn body and the compound represented by the following general formula (IB0) is an antibody.

[Chem. 9]

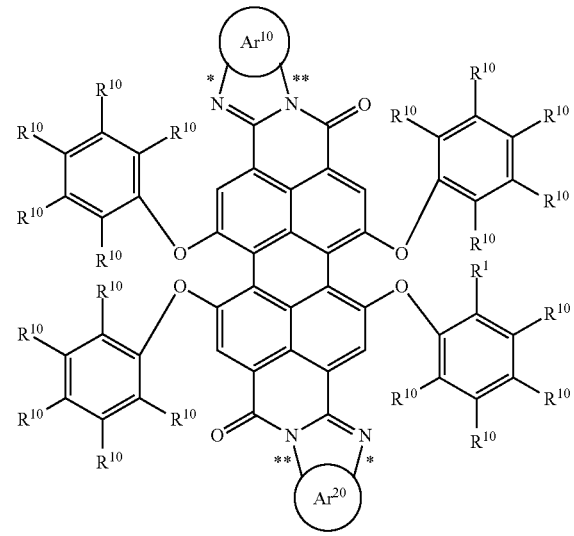

(IA0)

-continued

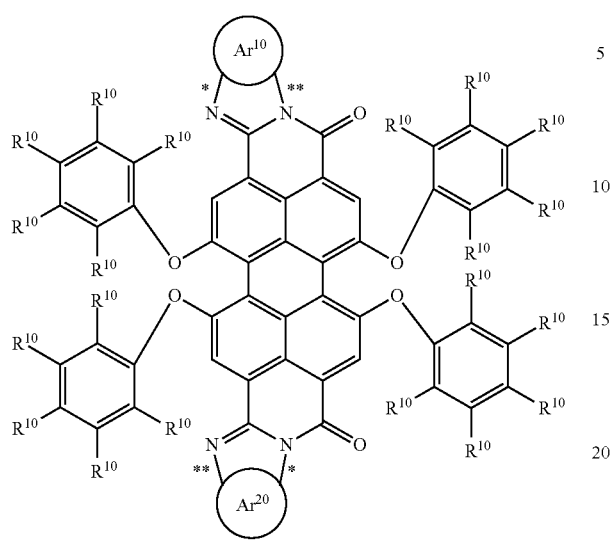
(IB0)

(In the formulae, $R^{10}$ represents a hydrogen atom, an alkyl group, an alkenyl group, an alkynyl group, an aryl group, an alkyl carbonyl amino group, or a group represented by the following general formula (z)-10 or (z)-20, and a plurality of Zs may be the same as or different from one another; $Ar^{10}$ and $Ar^{20}$ each independently represent a group represented by the following general formula (I)-110, (I)-120, (I)-130, (I)-210, or (I)-220; $R^{10}$ represents a hydrogen atom or an alkyl group when $Ar^1$ and $Ar^2$ each independently represent a group represented by the following general formula (I)-210 or (I)-220; and a bond marked with a symbol "*" is attached to a carbon atom marked with the symbol "*" of the group, and a bond marked with a symbol "" is attached to a carbon atom marked with the symbol "" of the group.)

[Chem. 10]

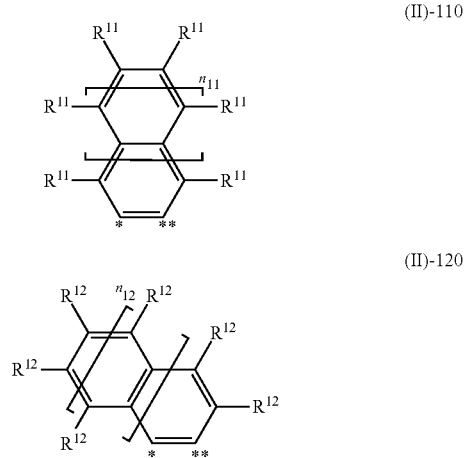

(II)-110

(II)-120

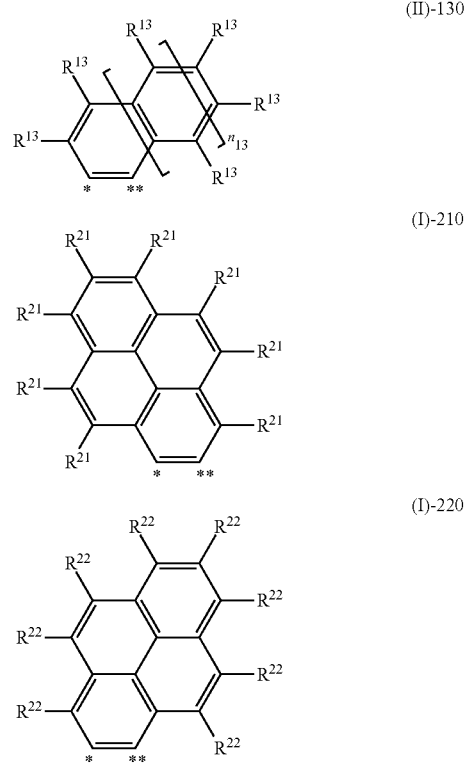

(II)-130

(I)-210

(I)-220

[Chem. 11]

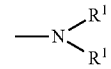
(Z)-10

(Z)-20

(In the formulae, $R^1$ represents a hydrogen atom, an alkyl group, or an aryl group, and two $R^1$s may be the same as or different from each other; $R^2$ represents a hydrogen atom or an alkyl group; $R^{11}$, $R^{12}$, $R^{13}$, $R^{21}$, and $R^{22}$ each independently represent a hydrogen atom or an alkyl group, and a plurality of $R^{11}$s, $R^{12}$s, $R''$s, $R''$s, and $R^{22}$s may be the same as or different from one another; and $n_{11}$ is an integer of 0 to 2, and $n_{11}$ is 1 or 2 when all R10 and R11 represent a hydrogen atom or an alkyl group, $n_{12}$ and $n_{13}$ are each independently 1 or 2, and a plurality of $n_{11}$s, $n_{12}$s, and $n_{13}$s may be the same as or different from one another.)

In the formulae, $R^{10}$ represents a hydrogen atom, an alkyl group, an alkenyl group, an alkynyl group, an aryl group, an alkyl carbonyl amino group, or a group represented by the general formula (z)-1 or (z)-2.

In the formulae, $R^1$ represents a hydrogen atom, an alkyl group, or an aryl group, and two $R^1$s may be the same as or different from each other. That is, the group represented by the general formula (z)-10 is an amino group, a monoalkyl amino group, a dialkyl amino group, a monoaryl amino group, a diaryl amino group, or an alkyl aryl amino group.

The alkyl group in $R^1$ may be linear, branched, or cyclic, and the alkyl group may be monocyclic or polycyclic when the alkyl group is cyclic. In addition, the number of carbon atoms of the alkyl group is preferably in the range of 1 to 20 and more preferably in the range of 1 to 10.

The number of carbon atoms of the linear or branched alkyl group is preferably 1 to 20, and examples of the alkyl group include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, a 1-methylbutyl group, an n-hexyl group, a 2-methylpentyl group, a 3-methylpentyl group, a 2,2-dimethylbutyl group, a 2,3-dimethylbutyl group, an n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, an n-octyl group, an isooctyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an icosyl group.

Among these, the number of carbon atoms of the linear or branched alkyl group is more preferably in the range of 1 to 10.

The number of carbon atoms of the cyclic alkyl group is preferably in the range of 3 to 20 and more preferably in the range of 3 to 10, and examples of the alkyl group include a cyclopropyl group, a cyclobutyl group, a cyclopentyl group, a cyclohexyl group, a cycloheptyl group, a cyclooctyl group, a cyclononyl group, a cyclodecyl group, a norbornyl group, an isobornyl group, a 1-adamantyl group, a 2-adamantyl group, and a tricyclodecyl group.

The aryl group in $R^1$ may be monocyclic or polycyclic and the number of carbon atoms thereof is preferably in the range of 6 to 12, and examples thereof include a phenyl group, a 1-naphthyl group, a 2-naphthyl group, an o-toluyl group (1-methylphenyl group), an m-toluyl group (2-methylphenyl group), a p-toluyl group (3-methylphenyl group), and a xylyl group (dimethylphenyl group). Further, one or more hydrogen atoms of these aryl groups may be substituted with an alkyl group. Here, as the alkyl group with which hydrogen atoms are substituted, groups which are the same as the above-described alkyl groups in $R^1$ can be exemplified.

The aryl group in $R^1$ is preferably monocyclic and more preferably a phenyl group.

It is preferable that $R^1$ represent a hydrogen atom, an alkyl group having 1 to 10 carbon atoms, or an aryl group having 6 to 12 carbon atoms.

In the formulae, $R^2$ represents a hydrogen atom or an alkyl group. That is, the group represented by the general formula (z)-20 is a hydroxyl group or an alkoxy group.

As the alkyl group in $R^2$, groups which are the same as the alkyl groups in $R^1$ can be exemplified, and the alkyl group in $R^2$ may be the same as or different from the alkyl group in $R^1$ in the same molecule.

It is preferable that $R^2$ represent an alkyl group having 1 to 10 carbon atoms.

The alkyl group in $R^{10}$ may be linear, branched, or cyclic, and the alkyl group may be monocyclic or polycyclic when the alkyl group is cyclic. Further, the number of carbon atoms of the alkyl group in Z is preferably in the range of 1 to 22, and more preferably in the range of 6 to 18 in terms of improving solubility in a solvent described below.

The number of carbon atoms of the linear or branched alkyl group in $R^{10}$ is preferably in the range of 1 to 22, and examples of the alkyl group include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, a 1-methylbutyl group, an n-hexyl group, a 2-methylpentyl group, a 3-methylpentyl group, a 2,2-dimethylbutyl group, a 2,3-dimethylbutyl group, an n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, an n-octyl group, an isooctyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a henicosyl group, and a docosyl group.

Among these, the number of carbon atoms of the linear or branched alkyl group is more preferably in the range of 6 to 18.

The number of carbon atoms of the cyclic alkyl group in $R^{10}$ is preferably in the range of 3 to 22, and examples of the alkyl group include a cyclopropyl group, a cyclobutyl group, a cyclopentyl group, a cyclohexyl group, a cycloheptyl group, a cyclooctyl group, a cyclononyl group, a cyclodecyl group, a norbornyl group, an isobornyl group, a 1-adamantyl group, a 2-adamantyl group, and a tricyclodecyl group. Further, groups in which one or more hydrogen atoms of these cyclic alkyl groups are substituted with a linear, branched, or cyclic alkyl group can be exemplified. Here, as the linear, branched, or cyclic alkyl group with which hydrogen atoms are substituted, groups which are the same as the above-described alkyl groups in Z can be exemplified.

Among these, the number of carbon atoms of the cyclic alkyl group is more preferably in the range of 6 to 18.

In a case where compounds (I0) include an alkyl group as $R^{10}$, the solubility in a solvent is improved by selecting an appropriate solvent for the compounds (I0) in the same manner as the case in which $R^{11}$, $R^{12}$, or $R^{13}$ described below represents an alkyl group. When the compounds (I0) with high solubility in a solvent are used, a solar power generation device, described below, whose power generation amount is increased can be more easily obtained. In this case, even in a case where the compounds (I0) without an alkyl group as $R^{10}$ are used, it is possible to obtain a solar power generation device whose power generation amount is sufficiently high.

The alkenyl group in $R^{10}$ may be linear, branched, or cyclic, and a group in which any one single bond (C—C) between carbon atoms is substituted with a double bond (C=C) can be exemplified as the alkyl group having 2 or more carbon atoms in $R^{10}$. Preferred examples of the alkenyl group include a vinyl group (ethenyl group, —CH=CH$_2$), an allyl group (2-propenyl group, —CH$_2$—CH=CH$_2$), a 1-propenyl group (—CH=CH—CH$_3$), an isopropenyl group (—C(CH$_3$)=CH$_2$), a 1-butenyl group (—CH=CH—CH$_2$—CH$_3$), a 2-butenyl group (—CH$_2$—CH=CH—CH$_3$), a 3-butenyl group (—CH$_2$—CH$_2$—CH=CH$_2$), a cyclohexenyl group, and a cyclopentenyl group.

The alkynyl group in $R^{10}$ may be linear, branched, or cyclic, and a group in which any one single bond (C—C) between carbon atoms is substituted with a triple bond (C≡C) can be exemplified as the alkyl group having 2 or more carbon atoms in $R^{10}$. Preferred examples of the alkenyl group include an ethynyl group (—CH≡CH) and a propargyl group (—CH$_2$—C≡CH).

As the aryl group in $R^{10}$, groups which are the same as the above-described aryl groups in $R^1$ can be exemplified.

A group in which one hydrogen atom of an amino group (—NH$_2$) is substituted with an alkyl carbonyl group can be exemplified as the alkyl carbonyl amino group in $R^{10}$. Further, a monovalent group in which the alkyl group in Z is bonded to a carbon atom of a carbonyl group (—C(=O)—) can be exemplified as the alkyl carbonyl group.

As a preferred example of the alkyl carbonyl amino group in $R^{10}$, a methyl carbonyl amino group (—NH—C(=O)—CH$_3$) or the like can be exemplified.

A plurality (twenty) of $R^{10}$s may be the same as or different from one another. That is, all $R^{10}$s may be the same as or different from one another, or some of $R^{10}$s may be different from one another.

In the case where $R^{10}$ represents an alkenyl group, an alkynyl group, an aryl group, an alkyl carbonyl amino group, or a group represented by the general formula (z)-10 or (z)-20, positions and the number of these $R^{10}$s in the compounds (I0) are not particularly limited.

In addition, in the compounds (I0), when $R^{10}$ is a relatively bulky group, a benzene ring skeleton to which $R^{10}$ is bonded is difficult to rotate using a bond between adjacent oxygen atoms as an axis because of large steric hindrance. For example, a case where a benzene ring skeleton does not rotate while focusing on the benzene ring skeleton in the same position in regard to compounds (I0) of two molecules is considered. A Group other than a hydrogen atom as $R^{10}$ is bonded to a carbon atom on the second position of the benzene ring skeleton in one compound (I0) and all hydrogen atoms as $R^{10}$ are bonded to other carbon atoms. In contrast, a group other than a hydrogen atom as $R^{10}$ is bonded to a carbon atom on the sixth position of the benzene ring skeleton in another compound (I0) and all hydrogen atoms as $R^{10}$ are bonded to other carbon atoms. These compounds (I0) are differentiated from each other as a stereoisomer even when the groups other than a hydrogen atom are the same as each other. Similarly, a compound (I0) in which a group other than a hydrogen atom as $R^{10}$ is bonded to a carbon atom on the third position of the benzene ring skeleton and all hydrogen atoms as $R^{10}$ are bonded to other carbon atoms is differentiated from a compound (I0) in which a group other than a hydrogen atom as Z is bonded to a carbon atom on the fifth position of the benzene ring skeleton and all hydrogen atoms as $R^{10}$ are bonded to other carbon atoms as a stereoisomer even when the above-described groups other than a hydrogen atom are the same as each other. In addition, the example described herein is merely an example and the stereoisomer is not limited thereto.

In the formulae, $Ar^{10}$ and $Ar^{20}$ each independently represent a group represented by the general formula (I)-110, (I)-120, (I)-130, (I)-210, or (I)-220. In this case, in a case where $Ar^{10}$ and $Ar^{20}$ each independently represent a group represented by the general formula (I)-210 or (I)-220, $R^{10}$ is a hydrogen atom or an alkyl group.

In the general formulae (IA0) and (IB0), a group represented by the general formula (I)-110, (I)-120, or (I)-130 and a group represented by the general formula (I)-210 or (I)-220 may or may not coexist.

When $Ar^{10}$ and $Ar^{20}$ each independently represent a group represented by the general formula (I)-11, (I)-12, (I)-13, (I)-21, or (I)-22, the light absorption peak wavelength of the compounds (I) becomes long. Further, the fluorescence quantum yield becomes large.

Further, in the present embodiment, the term "peak wavelength" means a wavelength of a main peak of a light spectrum, and spectrum intensity is preferably a wavelength with the maximum peak.

In the general formulae (IA0) and (IB0), bonds marked with a symbol "*" are attached to carbon atoms marked with the symbol "*" of the group represented by the general formula (I)-110, (I)-120, (I)-130, (I)-210, or (I)-220. That is, when it is described using the general formula (IA0) as an example, the bond stretched from N (nitrogen atom) of "—C(=N)—" toward $Ar^{10}$ is attached to the carbon atom marked with the symbol "*" of any one of the above-described groups as $Ar^{10}$, and the bond stretched from N (nitrogen atom) of "—C(=N)—" toward $Ar^{20}$ is attached to the carbon atom marked with the symbol "*" of any one of the above-described groups as $Ar^{20}$.

Similarly, in the general formulae (IA0) and (IB0), bonds marked with a symbol "" are attached to carbon atoms marked with the symbol "" of the group represented by the general formula (I)-110, (I)-120, (I)-130, (I)-210, or (I)-220. That is, when it is described using the general formula (IA0) as an example, the bond stretched from N (nitrogen atom) of "—C—N—C(=O)—" toward $Ar^{10}$ is attached to the carbon atom marked with the symbol "" of any one of the above-described groups as $Ar^{10}$, and the bond stretched from N (nitrogen atom) of "—C—N—C(=O)—" toward $Ar^{20}$ is attached to the carbon atom marked with the symbol "" of any one of the above-described groups as $Ar^{20}$.

In the formulae, $R^{11}$, $R^{12}$, $R^{13}$, $R^{21}$, and $R^{22}$ each independently represent a hydrogen atom or an alkyl group.

As the alkyl groups in $R^{11}$, $R^{12}$, $R^{13}$, $R^{21}$, and $R^{22}$, groups which are the same as the alkyl groups in $R^{10}$ can be exemplified, and the alkyl groups in $R^{11}$, $R^{12}$, $R^{13}$, $R^{21}$, and $R^{22}$ may be the same as or different from the alkyl groups in $R^{10}$ in the same molecule.

A plurality of $R^{11}$s, $R^{12}$s, $R^{13}$s, $R^{21}$s, and $R^{22}$s may be the same as or different from one another. For example, in the general formula (I)-110, a plurality ("$2n_{11}+4$") of $R^{11}$s may be the same as or different from one another. Moreover, in the general formula (I)-210, a plurality (eight) of $R^{21}$s may be the same as or different from one another.

In the case where any one or more $R^{11}$s, $R^{12}$, $R^{13}$, $R^{21}$s, or $R^{22}$s represent an alkyl group, the positions and the number of these alkyl groups in the compounds (I0) are not particularly limited.

It is preferable that $R^{11}$, $R^{12}$, $R^{13}$, $R^{21}$, and $R^{22}$ each independently represent a hydrogen atom or an alkyl group having 1 to 22 carbon atoms and more preferable that $R^{11}$, $R^{12}$, $R^{13}$, $R^{21}$, and $R^{22}$ each independently represent a hydrogen atom or an alkyl group having 6 to 18 carbon atoms.

In a case where the compounds (I0) include one or more alkyl groups in a molecule as $R^1$, $R^{11}$, $R^{12}$, $R^{13}$, $R^{21}$, or $R^{22}$, the solubility in a solvent is improved by selecting an appropriate solvent. When the compounds (I0) with high solubility in a solvent are used, a solar power generation device, described below, whose power generation amount is increased can be more easily obtained. In this case, in a case where the compounds (I0) without an alkyl group as $R^1$, $R^{11}$, $R^{12}$, $R^{13}$, $R^{21}$, or $R^{22}$ are used, it is possible to obtain a solar power generation device whose power generation amount is sufficiently high.

In the formulae, $n_{11}$ represents an integer of 0 to 2, and $n^{12}$ and $n^{13}$ each independently represent 1 or 2. For example, in the general formula (I)-110, when $n_{11}$ is 2, the group represented by the general formula (I)-110 is a group having a structure in which three benzene ring skeletons are condensed. Moreover, when $n_{11}$ is 0, the group represented by the general formula (I)-110 is a group having one benzene ring skeleton.

A plurality of $n_{11}$s, $n_{12}$s, and $n_{13}$s may be the same as or different from one another.

For example, in the general formulae (IA0) and (IB0), when both $Ar^{10}$ and $Ar^{20}$ represent a group represented by the general formula (I)-110, $n_{11}$ in $Ar^{10}$ and $n_{11}$ in $Ar^{20}$ may be the same as or different from each other. The same applies to $n_{12}$ in the general formula (I)-120 and $n_{13}$ in the general formula (I)-130.

The light absorption peak wavelength of the compound (I0) tends to be long as $n_{11}$, $n_{12}$, or $n_{13}$ is larger.

Further, it is preferable that $n_{11}$, $n_{12}$, or $n_{13}$ in $Ar^{10}$ and $Ar^{20}$ be the same as each other in terms of facilitating production of the compounds (I0) using a production method described below.

The peak wavelength of absorbable light of the compounds (I0) is preferably 640 nm or greater, and the absorption wavelength of light becomes sufficiently long by selecting an appropriate structure of the compounds (I0) so that the peak wavelength of absorbable light becomes 700 nm or greater.

The peak wavelength of absorbable light of the compounds (I0) can be acquired using quantum chemical calculation. At this time, a versatile quantum chemical calculation software can be used and Gaussian 09 (manufactured by Gaussian, Inc.) can be exemplified as the software. In addition, the peak wavelength of light can be acquired by level B3LYP/6-31G of a non-empirical molecular orbital calculation method.

Hereinafter, compounds 1 and 2 will be described as an example of the above-described compound.

<Compound 1>

A compound according to the present embodiment is represented by the following general formula (IA) or (IB) (hereinafter, these compounds are also simply written as compounds (I) collectively in some cases). Since the compounds (I) are novel fluorescent compounds and have a high absorption coefficient with respect to light having a long wavelength, such light can be sufficiently absorbed by the compounds. Among the compounds (I), the compound represented by the following general formula (IA) is a syn body and the compound represented by the following general formula (IB) is an antibody.

[Chem. 12]

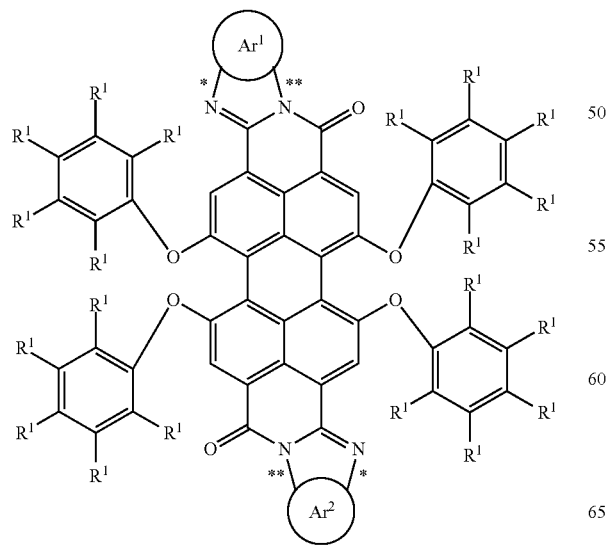

(IA)

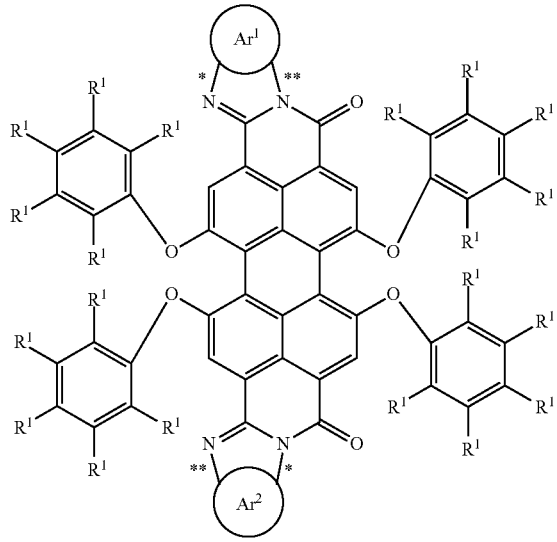

(IB)

(In the formulae, $R^1$ represents a hydrogen atom or an alkyl group, and a plurality of $R^1$s may be the same as or different from one another; $Ar^1$ and $Ar^2$ each independently represent a group represented by the following general formula (I)-11, (I)-12, (I)-13, (I)-21, or (I)-22; and a bond marked with a symbol "*" is attached to a carbon atom marked with the symbol "*" of the group, and a bond marked with a symbol "" is attached to a carbon atom marked with the symbol "" of the group.)

[Chem. 13]

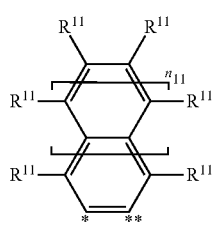

(I)-11

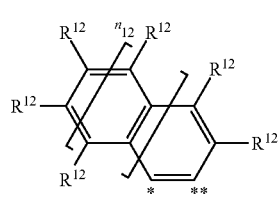

(I)-12

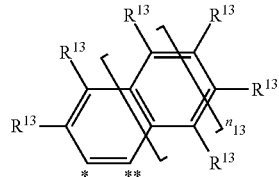

(I)-13

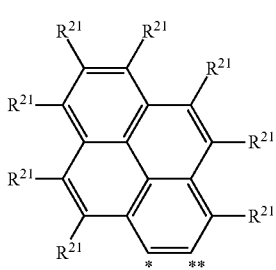

(I)-21

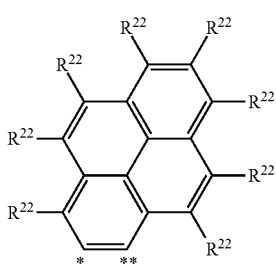

(I)-22

(In the formulae, $R^{11}$, $R^{12}$, $R^{13}$, $R^{21}$, and $R^{22}$ each independently represent a hydrogen atom or an alkyl group, and a plurality of $R^{11}$s, $R^{12}$s, $R^{13}$s, $R^{21}$s, and $R^{22}$s may be the same as or different from one another; and $n_{11}$, $n_{12}$, and $n_{13}$ are each independently 1 or 2, and a plurality of $n_{11}$s, $n_{12}$s, and $n_{13}$s may be the same as or different from one another.)

In the formulae, $R^1$ represents a hydrogen atom or an alkyl group.

The alkyl group in $R^1$ may be linear, branched, or cyclic, and the alkyl group may be monocyclic or polycyclic when the alkyl group is cyclic. In addition, the number of carbon atoms of the alkyl group is preferably in the range of 1 to 22, and more preferably in the range of 6 to 18 in terms of improving solubility in a solvent described below.

The number of carbon atoms of the linear or branched alkyl group is preferably in the range of 1 to 22, and examples of the alkyl group include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, a 1-methylbutyl group, an n-hexyl group, a 2-methylpentyl group, a 3-methylpentyl group, a 2,2-dimethylbutyl group, a 2,3-dimethylbutyl group, an n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, an n-octyl group, an isooctyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a henicosyl group, and a docosyl group.

Among these, the number of carbon atoms of the linear or branched alkyl group is more preferably in the range of 6 to 18.

The number of carbon atoms of the cyclic alkyl group is preferably in the range of 3 to 22, and examples of the alkyl group include a cyclopropyl group, a cyclobutyl group, a cyclopentyl group, a cyclohexyl group, a cycloheptyl group, a cyclooctyl group, a cyclononyl group, a cyclodecyl group, a norbornyl group, an isobornyl group, a 1-adamantyl group, a 2-adamantyl group, and a tricyclodecyl group. Further, groups in which one or more hydrogen atoms of these cyclic alkyl groups are substituted with a linear, branched, or cyclic alkyl group can be exemplified. Here, as the linear, branched, or cyclic alkyl group with which hydrogen atoms are substituted, groups which are the same as the above-described alkyl groups in $R^1$ can be exemplified.

Among these, the number of carbon atoms of the cyclic alkyl group is more preferably in the range of 6 to 18.

A plurality (twenty) of $R^1$s may be the same as or different from one another. That is, all $R^1$s may be the same as or different from one another, or some of $R^1$s may be different from one another.

In the case where any one or more $R^1$s represent an alkyl group, positions and the number of the alkyl group in the compounds (I) are not particularly limited. Among these, in a benzene ring skeleton to which $R^1$s and an oxygen atom are bonded, it is preferable that $R^1$s (in the para position with respect to the oxygen atom) bonded to the carbon atom on the fourth position be alkyl groups. Further, among four benzene ring skeleton skeletons, the number of $R^1$s, which are bonded to the carbon atoms on the fourth position, being alkyl groups is preferably 2 or more and more preferably 3 or more. In addition, it is particularly preferable that $R^1$s bonded to the carbon atoms on the fourth position be alkyl groups in all of four benzene ring skeletons.

In addition, in the compound (I), a benzene ring skeleton to which $R^1$ is bonded is difficult to rotate using a bond between adjacent hydrogen atoms as an axis because of large steric hindrance. For example, a case where a benzene ring skeleton does not rotate while focusing on the benzene ring skeleton in the same position in regard to compounds (I) of two molecules is considered. An alkyl group as $R^1$ is bonded to the carbon atom on the second position of the benzene ring skeleton in one compound (I) and all hydrogen atoms as $R^1$ are bonded to other carbon atoms. In contrast, an alkyl group as $R^1$ is bonded to the carbon atom on the sixth position of the benzene ring skeleton in another compound (I) and all hydrogen atoms as $R^1$ are bonded to other carbon atoms. These compounds (I) are differentiated from each other as a stereoisomer even when the alkyl groups are the same as each other. Similarly, a compound (I) in which an alkyl group as $R^1$ is bonded to a carbon atom on the third position of the benzene ring skeleton and all hydrogen atoms as $R^1$ are bonded to other carbon atoms is differentiated from a compound (I) in which an alkyl group as $R^1$ is bonded to the carbon atom on the fifth position of the benzene ring skeleton and all hydrogen atoms as $R^{10}$ are bonded to other carbon atoms as a stereoisomer even when alkyl groups are the same as each other. In addition, the example described herein is merely an example and the stereoisomer is not limited thereto.

It is preferable that $R^1$ represent a hydrogen atom or an alkyl group having 1 to 22 carbon atoms and more preferable that $R^1$ represent a hydrogen atom or an alkyl group having 6 to 18 carbon atoms.

In the formulae, $Ar^1$ and $Ar^2$ each independently represent a group represented by the general formula (I)-11, (I)-12, (I)-13, (I)-21, or (I)-22.

In the general formulae (IA) and (IB), a group represented by the general formula (I)-11, (I)-12, or (I)-13 and a group represented by the general formula (I)-21 or (I)-22 may or may not coexist. Hereinafter, in the compounds (I), compounds (I) in which both $Ar^1$ and $Ar^2$ represent a group represented by the general formula (I)-11, (I)-12, or (I)-13 are particularly simply written as "compounds (1)" and compounds (I) in which both $Ar^1$ and $Ar^2$ represent a group represented by the general formula (I)-21 or (I)-22 are particularly simply written as "compounds (2)."

When $Ar^1$ and $Ar^2$ each independently represent a group represented by the general formula (I)-11, (I)-12, (I)-13, (I)-21, or (I)-22, the light absorption peak wavelength of the compound (I) becomes long. Further, the fluorescence quantum yield becomes large.

Further, in the present embodiment, the term "peak wavelength" means a wavelength of a main peak of a light spectrum, and spectrum intensity is preferably a wavelength with the maximum peak.

In the general formulae (IA) and (IB), bonds marked with a symbol "*" are attached to carbon atoms marked with the symbol "*" of the group represented by the general formula (I)-11, (I)-12, (I)-13, (I)-21, or (I)-22. That is, when it is described using the general formula (IA) as an example, the bond stretched from N (nitrogen atom) of "—C(=N)—" toward Ar¹ is attached to the carbon atom marked with the symbol "*" of any one of the above-described groups as Ar¹, and the bond stretched from N (nitrogen atom) of "—C(=N)—" toward Ar² is attached to the carbon atom marked with the symbol "*" of any one of the above-described groups as Ar².

Similarly, in the general formulae (IA) and (IB), bonds marked with a symbol "" are attached to carbon atoms marked with the symbol "" of the group represented by the general formula (I)-11, (I)-12, (I)-13, (I)-21, or (I)-22. That is, when it is described using the general formula (IA) as an example, the bond stretched from N (nitrogen atom) of "—C—N—C(=O)—" toward Ar¹ is attached to the carbon atom marked with the symbol "" of any one of the above-described groups as Ar¹, and the bond stretched from N (nitrogen atom) of "—C—N—C(=O)—" toward Ar² is attached to the carbon atom marked with the symbol "" of any one of the above-described groups as Ar².

In the formulae, $R^{11}$, $R^{12}$, $R^{13}$, $R^{21}$, and $R^{22}$ each independently represent a hydrogen atom or an alkyl group.

As the alkyl groups in $R^{11}$, $R^{12}$, $R^{13}$, $R^{21}$, and $R^{22}$, groups which are the same as the alkyl groups in $R^1$ can be exemplified, and the alkyl groups in $R^{11}$, $R^{12}$, $R^{13}$, $R^{21}$, and $R^{22}$ may be the same as or different from the alkyl groups in $R^1$ in the same molecule.

A plurality of $R^{11}$s, $R^{12}$s, $R^{13}$s, $R^{21}$s, and $R^{22}$s may be the same as or different from one another. For example, in the general formula (I)-11, a plurality ("$2n_{11}+4$") of $R^{11}$s may be the same as or different from one another. Moreover, in the general formula (I)-21, a plurality (eight) of $R^{21}$s may be the same as or different from one another.

In the case where any one or more $R^{11}$s, $R^{12}$s, $R^{13}$s, $R^{21}$s, or $R^{22}$s represent an alkyl group, the positions and the number of these alkyl groups in the compounds (I) are not particularly limited.

It is preferable that $R^{11}$, $R^{12}$, $R^{13}$, $R^{21}$, and $R^{22}$ each independently represent a hydrogen atom or an alkyl group having 1 to 22 carbon atoms and more preferable that $R^{11}$, $R^{12}$, $R^{13}$, $R^{21}$, and $R^{22}$ each independently represent a hydrogen atom or an alkyl group having 6 to 18 carbon atoms.

In a case where the compound (I) includes one or more alkyl groups in a molecule as $R^1$, $R^{11}$, $R^{12}$, $R^{13}$, $R^{21}$, or $R^{22}$, the solubility in a solvent is improved by selecting an appropriate solvent. When the compounds (I) with high solubility in a solvent are used, a solar power generation device, described below, whose power generation amount is increased can be more easily obtained. In this case, even in a case where the compounds (I) without an alkyl group as $R^1$, $R^{11}$, $R^{12}$, $R^{13}$, $R^{21}$, or $R^{22}$ are used, it is possible to obtain a solar power generation device whose power generation amount is sufficiently high.

In the formulae, $n_{11}$, $n_{12}$, and $n_{13}$ each independently represent 1 or 2. For example, in the general formula (I)-11, when $n_{11}$ is 1, the group represented by the general formula (I)-11 is a group having a structure in which two benzene ring skeletons are condensed. Moreover, when $n_{11}$ is 2, the group represented by the general formula (I)-11 is a group having a structure in which three benzene ring skeletons are condensed.

A plurality of $n_{11}$s, $n_{12}$s, and $n_{13}$s may be the same as or different from one another.

For example, in the general formulae (IA) and (IB), when both Ar¹ and Ar² represent a group represented by the general formula (I)-11, $n_{11}$ in Ar¹ and $n_{11}$ in Ar² may be the same as or different from each other. The same applies to $n_{12}$ in the general formula (I)-12 and $n_{13}$ in the general formula (I)-13.

The light absorption peak wavelength of the compound (1) among the compounds (I) tends to be long when $n_{11}$, $n_{12}$, or $n_{13}$ is 2 rather than 1.

Further, it is preferable that $n_{11}$, $n_{12}$, or $n_{13}$ in Ar¹ and Ar² be the same as each other in terms of further facilitating production of the compounds (I) using a production method described below.

The light absorption peak wavelength of the compounds (I) is preferably 650 nm or greater and more preferably 660 nm or greater so that the absorption wavelength of light becomes sufficiently long. Particularly, since the effect of the compound (2) is higher, the light absorption peak wavelength can be set to be preferably 730 nm or greater and more preferably 750 nm or greater.

Strength of an oscillator tends to be great in particularly the compound (2) among the compounds (I) and the fluorescence quantum yield tends to be larger in such compounds (I).

A solar power generation device, described below, with a large power generation amount can be obtained using a compound (I) whose fluorescence quantum yield is large.

The light absorption peak wavelength of the compounds (I) can be acquired using quantum chemical calculation. At this time, a versatile quantum chemical calculation software can be used and Gaussian 09 (manufactured by Gaussian, Inc.) can be exemplified as the software. In addition, the peak wavelength of light can be acquired by level B3LYP/6-31G (d) of a non-empirical molecular orbital calculation method.

Among the compounds (I), compounds represented by the following general formulae (1A)-1 to (1A)-6, and (1B)-1 to (1B)-6 can be exemplified as the compounds (1).

[Chem. 14]

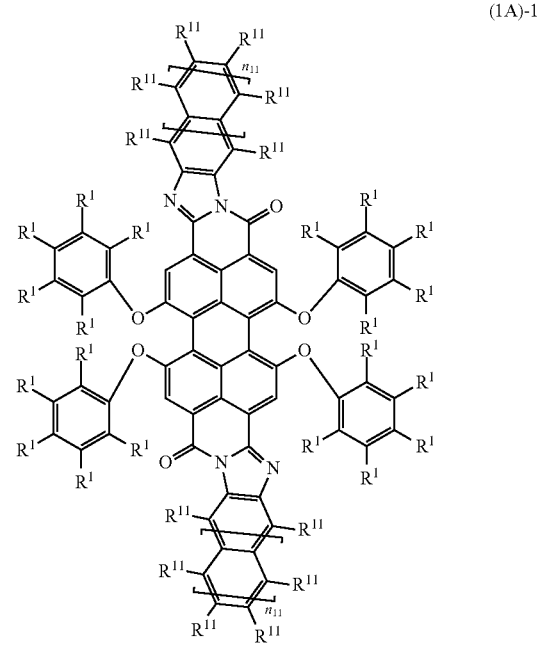

(1A)-1

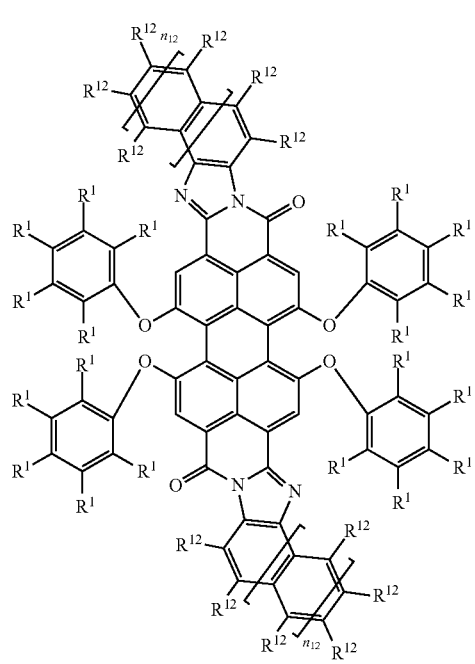
(IA)-2
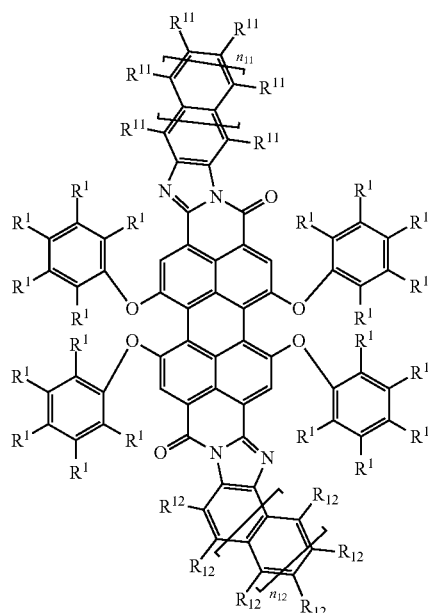
(IA)-4
(In the formulae, $R^1$, $R^{11}$, $R^{12}$, $R^{13}$, $n_{11}$, $n_{12}$, and $n_{13}$ are the same as those described above.)
[Chem. 15]
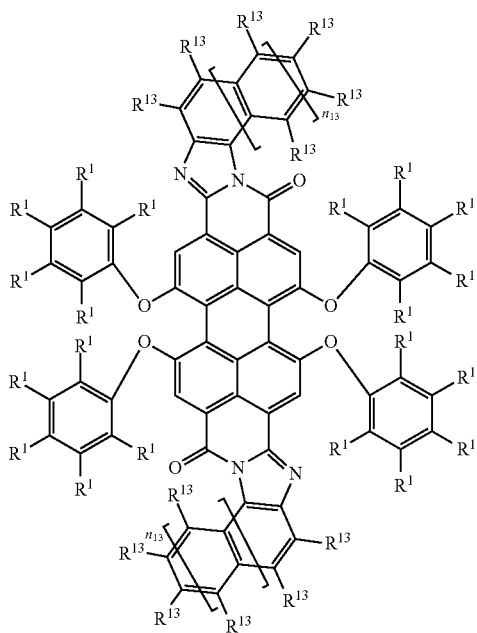
(1A)-3
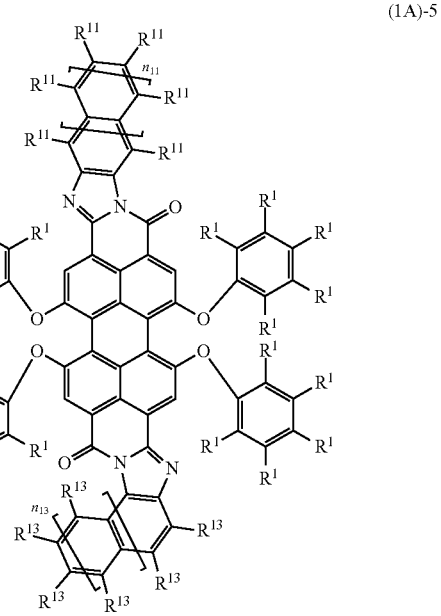
(1A)-5

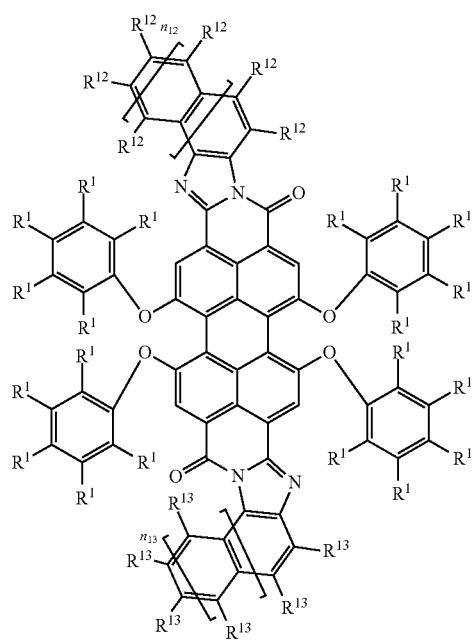
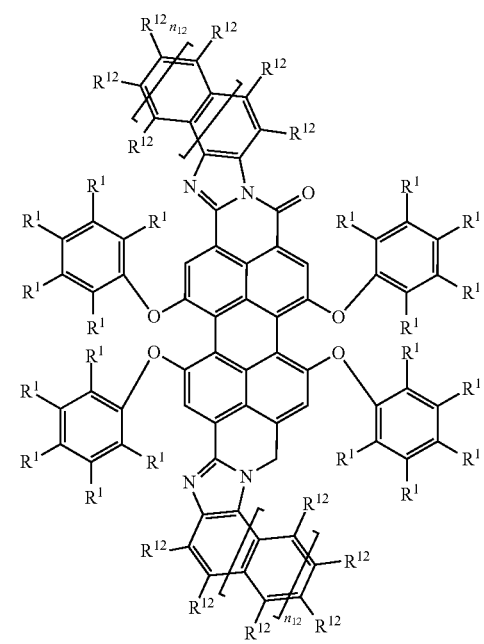
(In the formulae, $R^1$, $R^{11}$, $R^{12}$, $R^{13}$, $n_{11}$, $n_{12}$, and $n_{13}$ are the same as those described above.)
[Chem. 16]
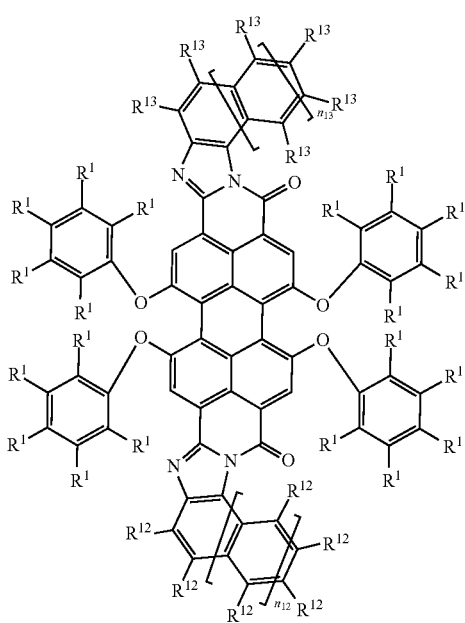

(1B)-4
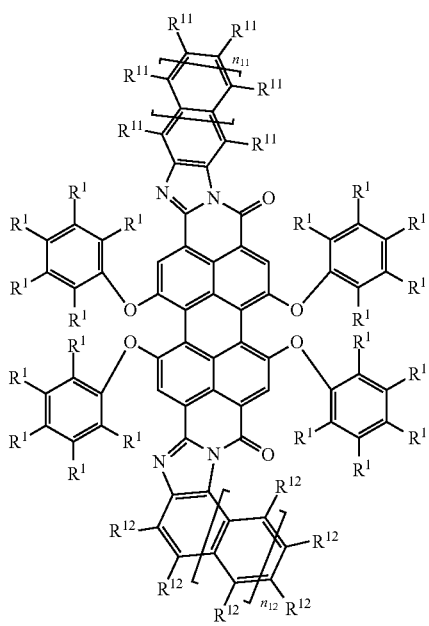
(In the formulae, $R^1$, $R^{11}$, $R^{12}$, $R^{13}$, $n_{11}$, $n_{12}$, and $n_{13}$ are the same as those described above.)
(1B)-6
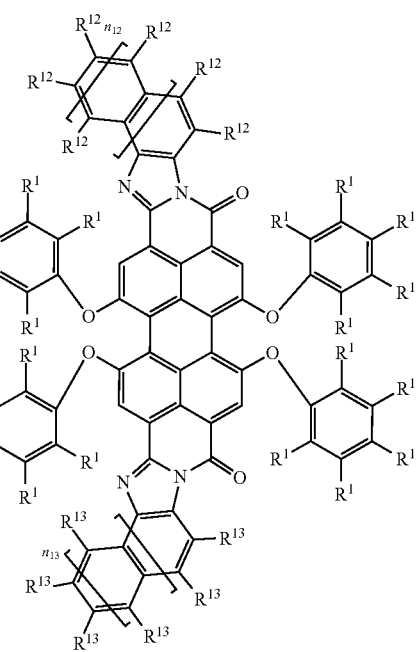
(In the formulae, $R^1$, $R^{11}$, $R^{12}$, $R^{13}$, $n_{11}$, $n_{12}$, and $n_{13}$ are the same as those described above.)
Among the compounds (I), compounds represented by the following general formulae (2A)-1 to (2A)-3, and (2B)-1 to (2B)-3 can be exemplified as the compounds (2).
[Chem. 17]
(1B)-5
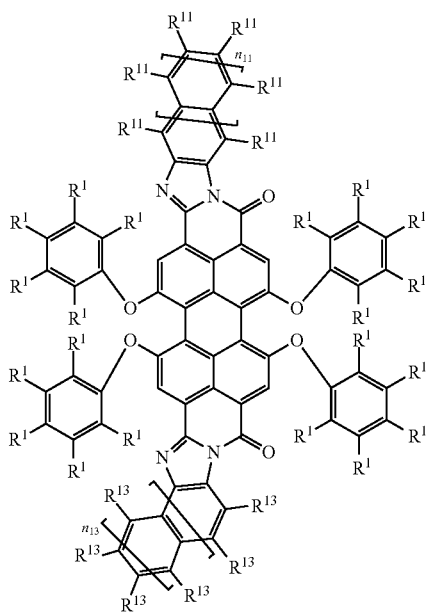
[Chem. 18]
(2A)-1
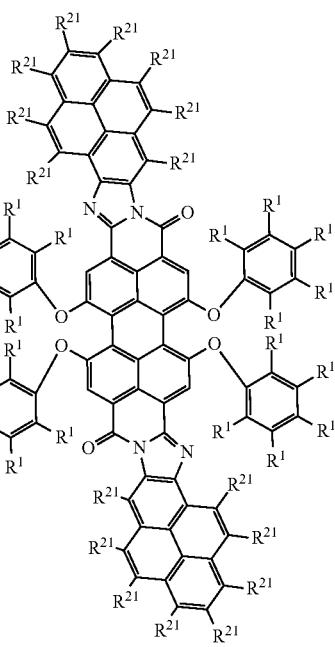

-continued
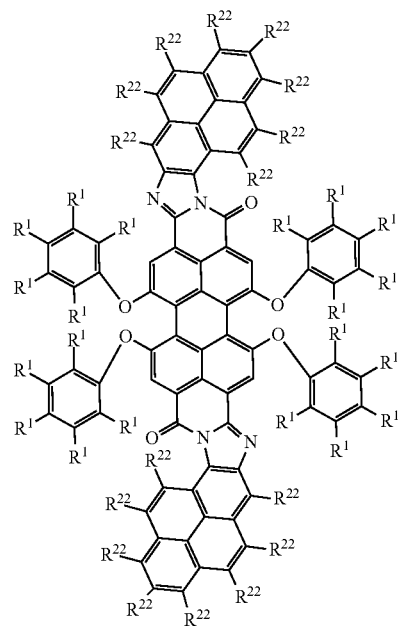
(2A)-2
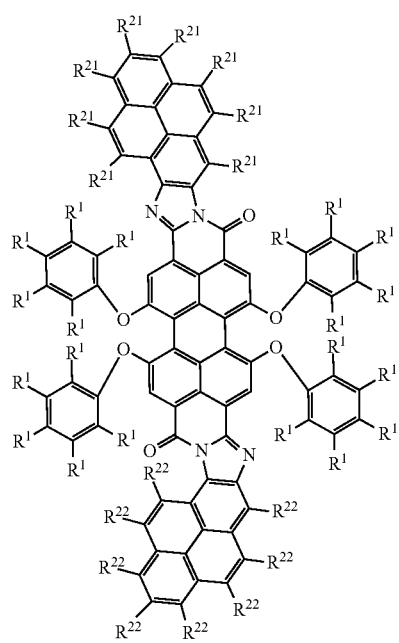
(2A)-3
[Chem. 19]
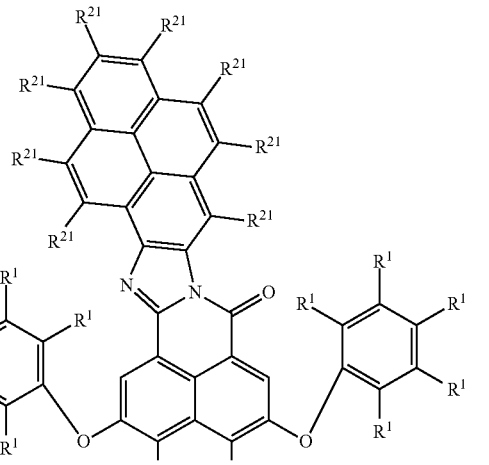
(2B)-1
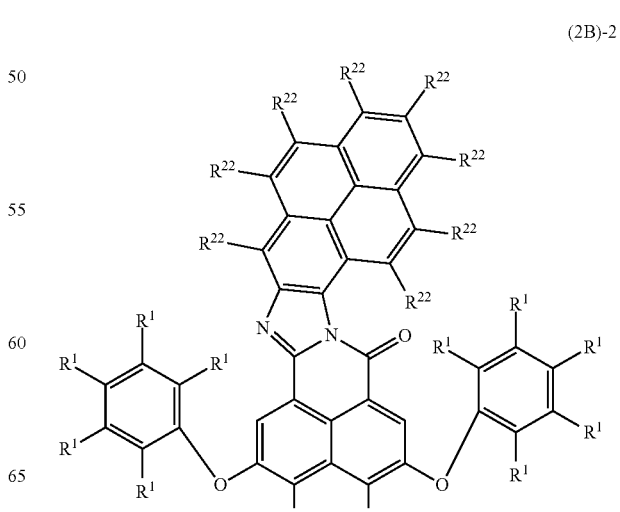
(2B)-2
(In the formulae, $R^1$, $R^{21}$, and $R^{22}$ are the same as those described above.)

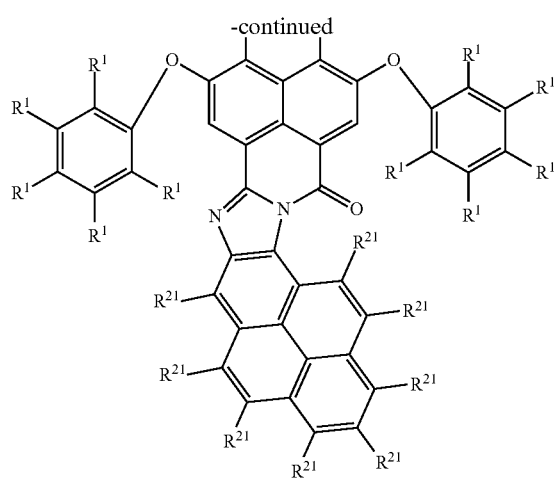

(2B)-3

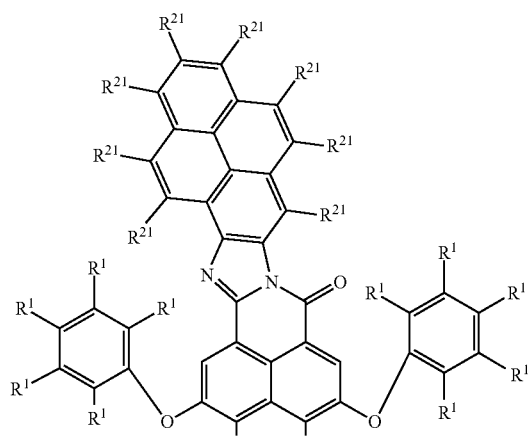

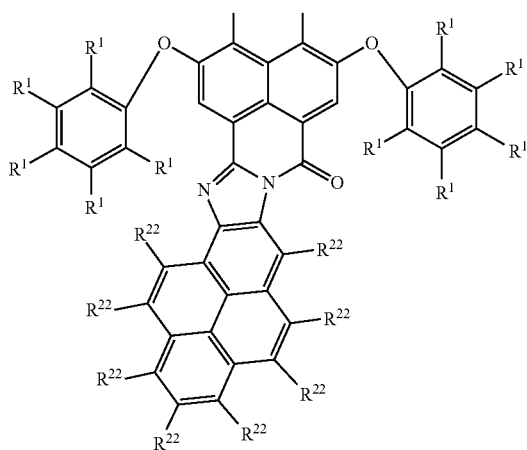

(In the formulae, $R^1$, $R^{21}$, and $R^{22}$ are the same as those described above.)

Further, here, the compounds (1) and (2) are exemplified as the compounds (I), but compounds in which the group represented by the general formula (I)-11, (I)-12, or (I)-13 and the group represented by the general formula (I)-21 or (I)-22 coexist as $Ar^1$ or $Ar^2$ after substitution of $Ar^1$ or $Ar^2$ in these compounds (1) and (2) can be exemplified as the compounds (I).

Since the compounds (I) can absorb light having a sufficiently long wavelength, such a solar power generation device has an excellent power generation amount by means of using the compounds (I) as a phosphor in the solar power generation device described below.

The compounds (I) can be produced by a production method including a process of producing compounds (Ib) and a process of producing compounds (I). The process of producing compounds (Ib) is a process of obtaining compounds (hereinafter, these compounds are also simply written as "compounds (Ib)" collectively) represented by the following general formulae (IAb) and/or (IBb) by reacting a compound (hereinafter, simply written as the "compound (Ie)") represented by the following general formula (Ie), a compound (hereinafter, simply written as the "compound (Id)") represented by the following general formula (Id), and a compound (hereinafter, simply written as the "compound (Ic)") represented by the following general formula (Ic). The process of producing compounds (I) is a process of obtaining compounds (I) by reacting a compound (Ib) and a compound (hereinafter, simply written as the "compound (Ia)") represented by the following general formula (Ia). However, the production method exemplified here is merely an example and the method of producing compounds (I) is not limited thereto.

Moreover, in the following reaction formulae, an example in which both compounds represented by the general formulae (IAb) and (IBb) are generated is exemplified as compounds (Ib), but only either of the compounds is generated in some cases as described above. In addition, a compound (I) represented by the general formula (IA) is generated from a compound (Ib) represented by the general formula (IAb) and a compound (I) represented by the general formula (IB) is generated from a compound (Ib) represented by the general formula (IBb).

[Chem. 20]

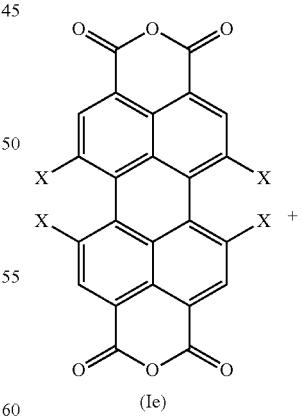

(Ie)

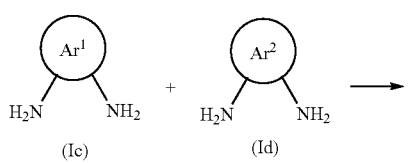

(Ic)    (Id)

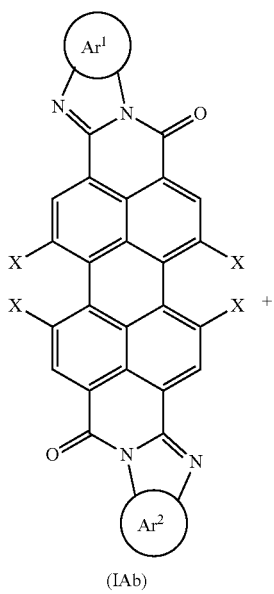

(IAb)

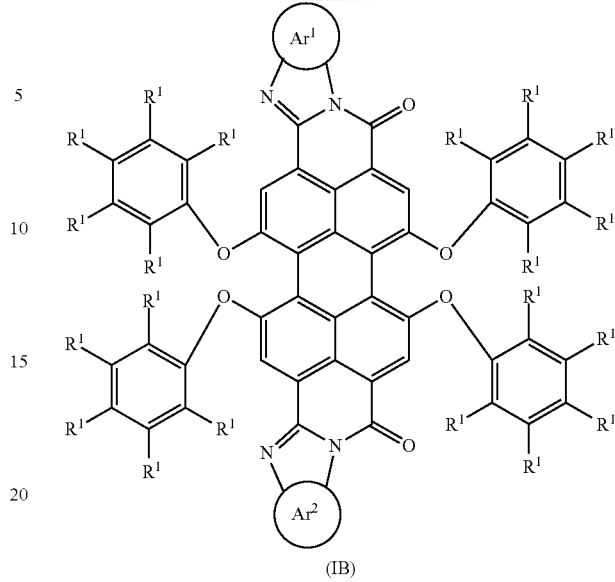

(IB)

(In the formulae, $R^1$, $Ar^1$, and $Ar^2$ are the same as those described above; and X represents a halogen atom.)

In the process of producing the compound (Ib), the compounds (Ic), (Id), and (Ie) are reacted. Such reaction is a dehydration condensation reaction.

In the compound (Ic), $Ar^1$ is the same as $Ar^1$ in the general formulae (IA) and (IB). Further, among two amino groups (—NH$_2$) bonded to $Ar^1$, a bond made by one amino group being bonded to $Ar^1$ is a bond marked with the symbol "*" in the general formulae (IA) and (IB) and another bond made by another amino group being bonded to $Ar^1$ is a bond marked with the symbol "**" in the general formulae (IA) and (IB).

In the compound (Id), $Ar^2$ is the same as $Ar^2$ in the general formulae (IA) and (IB). Further, among two amino groups (—NH$_2$) bonded to $Ar^2$, a bond made by one amino group being bonded to $Ar^2$ is a bond marked with the symbol "*" in the general formulae (IA) and (IB) and another bond made by another amino group being bonded to $Ar^2$ is a bond marked with the symbol "**" in the general formulae (IA) and (IB).

The compounds (Ic) and (Id) may be the same as or different from each other and may be appropriately selected according to the structures of target compounds (I).

In the compound (Ie), X represents a halogen atom, and preferably a chlorine atom, a bromine atom, or an iodine atom, and a plurality (four) of Xs may be the same as or different from one another, but it is preferable that all of Xs be the same as one another.

In the process of producing the compound (Ib), it is preferable to perform a reaction using a solvent. The solvent can be appropriately and arbitrarily selected from solvents not prohibiting the reaction in consideration of solubility and the reaction condition of a compound to be a raw material, and an aromatic compound such as toluene or phenol can be exemplified as a specific example of the solvent. In addition, an organic acid such as a propionic acid or the like may be used.

In the process of producing the compound (Ib), in a case where an organic acid such as a propionic acid or the like is not used as a solvent, it is preferable that the reaction be performed using a base such as pyridine or pyrazine.

In the process of producing the compound (Ib), the total amount of the compounds (Ic) and (Id) to be used is preferably 2 molar times or more and more preferably 4 molar times

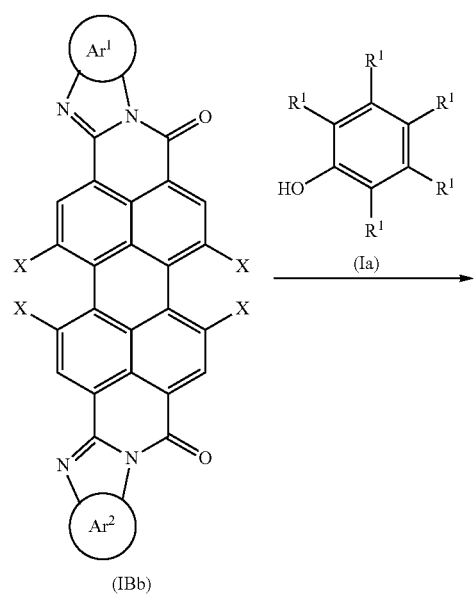

(IBb)

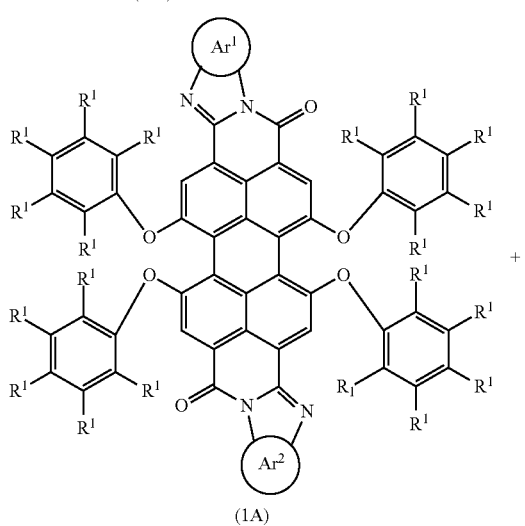

(1A)

to 5 molar times with respect to the compound (Ie). Further, the amount of the base to be used is preferably 1 molar time or more and more preferably 4 molar times to 5 molar times with respect to the compound (Ie).

In the process of producing the compound (Ib), in the case where the reaction is performed using a base such as pyridine or pyrazine, the reaction temperature is preferably in the range of 120° C. to 150° C. and the reaction time is preferably in the range of 6 hours to 36 hours. Meanwhile, in the case where the reaction is performed using an organic acid such as a propionic acid, the reaction temperature is preferably in the range of 130° C. to 150° C. and the reaction time is preferably in the range of 5 hours to 8 hours.

The reaction may be performed while removing water which is secondarily produced using azeotropic dehydration. At this time, a solvent may be appropriately added during the reaction.

In the process of producing the compound (Ib), in a case where the same compounds are used as compounds (Ic) and (Id), it becomes easy to obtain symmetric compounds (Ib) in $Ar^1$ and $Ar^2$. Symmetric compounds (I) in $Ar^1$ and $Ar^2$ can be obtained from the compounds (Ib) having such a symmetric structure.

In contrast, in a case where different compounds are used as the compounds (Ic) and (Id) or compounds in which $Ar^1$ and $Ar^2$ are groups other than the groups represented by the general formula (I)-11 are used as the compounds (Ic) and (Id), it becomes easy to obtain asymmetric compounds (Ib) in $Ar^1$ and $Ar^2$ and asymmetric compounds (I) in $Ar^1$ and $Ar^2$ can be obtained from the compounds (Ib) having such an asymmetric structure.

Further, even in a case of symmetric or asymmetric compounds in $Ar^1$ and $Ar^2$, it is possible to obtain both compounds represented by the general formulae (IAb) and (IBb) as compounds (Ib) according to the reaction site of the compounds (Ie) with the compounds (Ic) and (Id).

Meanwhile, in a case where compounds in which $Ar^1$ and $Ar^2$ are the same groups represented by the general formula (I)-11 are used as the compounds (Ic) and (Id) and only one kind of compound is used as the compound (Ie), respectively only one kind of compound represented by the general formula (IAb) or (IBb) is generated as the compounds (Ib).

In this manner, plural kinds of compounds can be generated as the compounds (Ib). In a case where some kinds of the compounds are used, a target compound may be separated by employing a purifying method described below. Further, the formation rate of the target compound may be improved by adjusting the reaction condition.

In the process of producing the compound (Id), after the reaction is terminated, the compound (Ib) may be extracted by performing a post-treatment according to the necessity using a known technique. That is, the compound (Ib) may be extracted through concentration, crystallization, reprecipitation, column chromatography, or the like by appropriately performing any one of post-treatment operations such as filtration, washing, extraction, pH adjustment, dehydration, concentration, and the like or a combination of two or more kinds thereof if necessary. In addition, the extracted compound (Ib) may be purified by performing any one of operations such as crystallization, reprecipitation, column chromatography, extraction, stirring and washing crystals using a solvent, and the like or a combination of two or more kinds thereof if necessary.

In the process of producing the compound (Ib), after the reaction is terminated and the post-treatment is performed if necessary, the process of producing the compound (I) may be continuously performed without extracting the compound (Ib).

In the process of producing the compound (I), the compounds (Ia) and (Ib) are reacted.

In the compound (Ia), $R^1$ is the same as $R^1$ in the general formulae (IA) and (IB). In a case where a product of the compound (Ib) is commercially available, the process of producing the compound (Ib) can be omitted by means of using the product of the compound (Ib).

In the process of producing the compound (I), it is preferable to perform a reaction using a solvent. The solvent can be appropriately and arbitrarily selected from solvents not prohibiting the reaction in consideration of solubility and the reaction condition of a compound to be a raw material, and specific examples thereof include an amide compound such as N-methylpyrrolidone, N,N-dimethylformamide, or N,N-dimethylacetamide.

Moreover, it is preferable to perform the reaction using a base such as potassium carbonate or sodium carbonate in the process of producing the compound (I).

In the process of producing the compound (I), the amount of the compound (Ia) to be used is preferably 4 molar times or more and more preferably 4 molar times to 8 molar times with respect to the compound (Ib). Further, the amount of the base to be used is preferably 1 molar time or more and more preferably 1 molar time to 6 molar times with respect to the compound (Ia).

The reaction temperature of the reaction in the process of producing the compound (I) is preferably in the range of 130° C. to 150° C. and the reaction time thereof is preferably in the range of 18 hours to 36 hours.

In the process of producing the compound (I), in a case where one kind of compound is used as the compound (Ia), one kind of compound (I) is generated from one kind of compound (Ib).

Meanwhile, in a case where plural kinds of compounds are used as the compound (Ia), plural kinds of compounds (I) are generated even from one kind of compound (Ib). Further, even when one kind of compound is used as the compound (Ia), plural kinds of compounds (I) are generated in a case where plural kinds of compounds (Ib) (mixture of compounds (Ib)) are used. In this manner, in a case where plural kinds of compounds are generated as the compounds (I) and some kinds of the compounds are used, a target compound may be separated using the same method as that of the case of the above-described compound (Ib) and the formation rate of the target compound may be improved by adjusting the reaction condition.

In the process of producing the compound (I), after the reaction is terminated, the compound (I) may be extracted and then the extracted compound (I) may be purified using the same method as that of the case of the process of producing the compound (Ib).

Structures of the compounds (I) and (Ib) can be verified using known techniques such as nuclear magnetic resonance (NMR) spectroscopy, mass spectrometry (MS), and infrared spectroscopy (IR).

Moreover, the compounds (I) may be synthesized through the chemical formulae (1-1) to (1-5).

[Chem. 21]
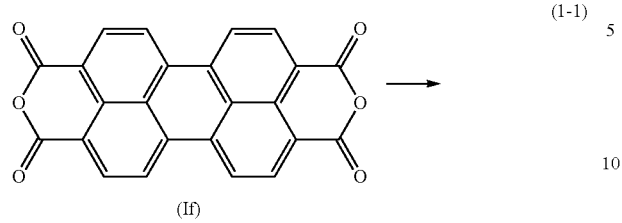
(1-1)
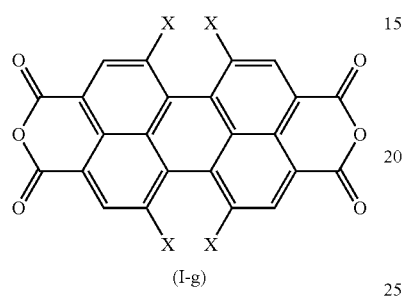
[Chem. 22]
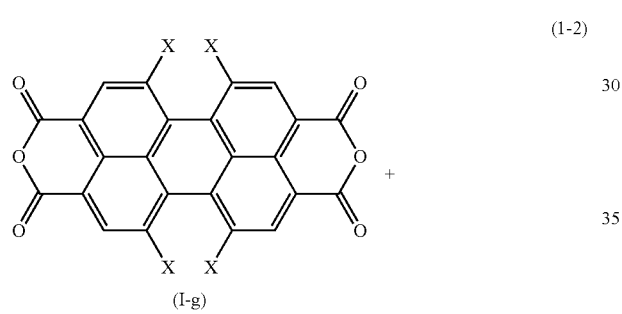
(1-2)
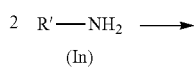
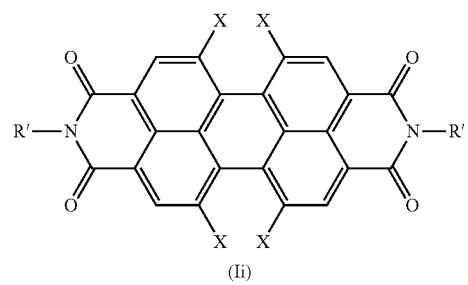
[Chem. 23]
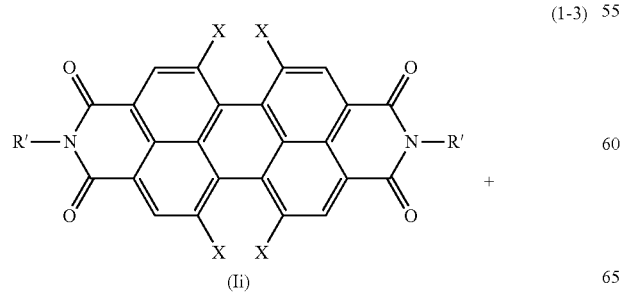
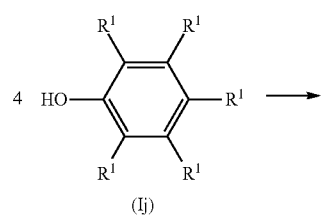
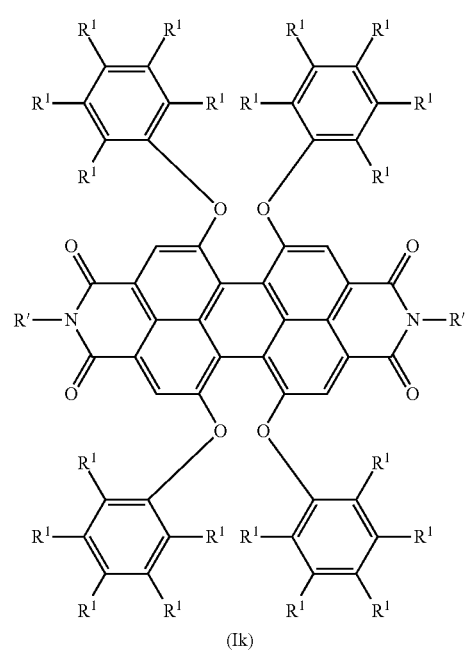
[Chem. 24]
(1-4)
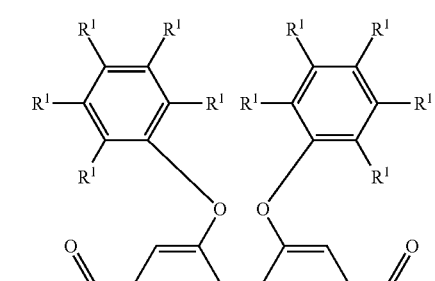
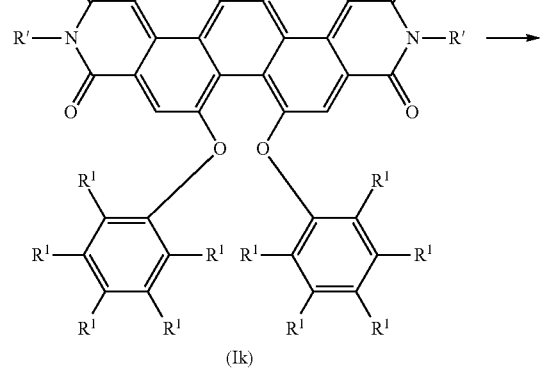

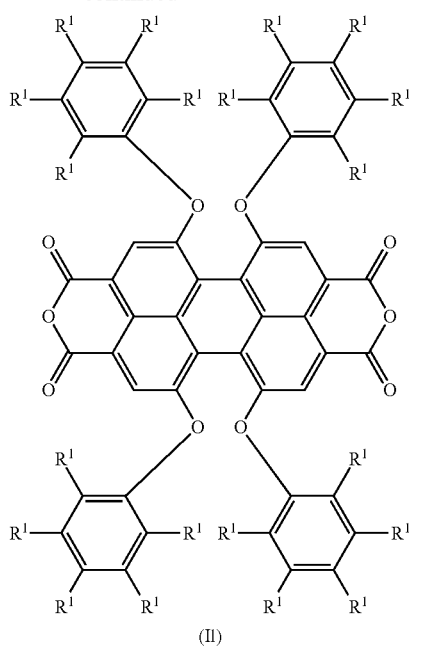

(II)

[Chem. 25]

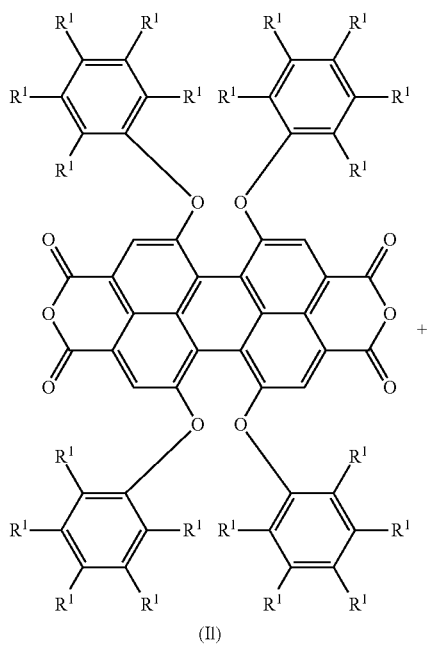

(II)

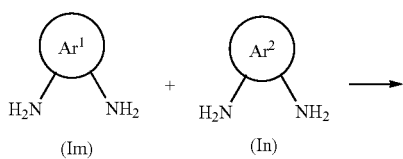

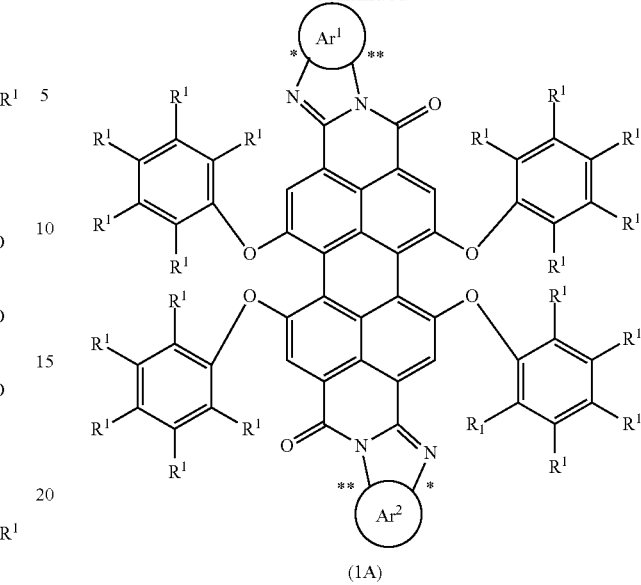

(1A)

+

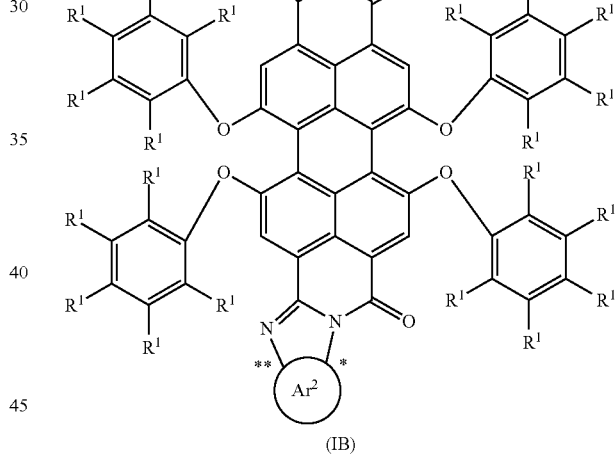

(IB)

In the compound (Ig), X preferably represents a halogen atom, a chlorine atom, a bromine atom, or an iodine atom, and a plurality (four) of Xs may be the same as or different from one another, but it is preferable that all of Xs be the same as one another.

In the compound (Ii), R' is a protecting group. Specific examples thereof include a linear alkyl group having 1 to 22 carbon atoms.

In the compounds (Ij), (Ik), and (II), $R^1$ is the same as $R^1$ in the general formulae (IA) and (IB).

In the compound (Im), $Ar^1$ is the same as $Ar^1$ in the general formulae (IA) and (IB). Further, among two amino groups (—$NH_2$) bonded to $Ar^1$, a bond made by one amino group being bonded to $Ar^1$ is a bond marked with the symbol "*" in the general formulae (IA) and (IB) and another bond made by another amino group being bonded to $Ar^1$ is a bond marked with the symbol "**" in the general formulae (IA) and (IB).

In the compound (In), $Ar^2$ is the same as $Ar^2$ in the general formulae (IA) and (IB). Further, among two amino groups (—NH$_2$) bonded to Ar$^2$, a bond made by one amino group being bonded to Ar$^2$ is a bond marked with the symbol "*" in the general formulae (IA) and (IB) and another bond made by another amino group being bonded to Ar$^2$ is a bond marked with the symbol "**" in the general formulae (IA) and (IB).

The compounds (Im) and (In) may be the same as or different from each other and may be appropriately selected according to the structures of target compounds (I).

In the reaction shown in the chemical formula (1-3), the compounds (Ii) and (Ij) are reacted.

In the reaction shown in the chemical formula (1-3), it is preferable to perform a reaction using a solvent. The solvent can be appropriately and arbitrarily selected from solvents not prohibiting the reaction in consideration of solubility and the reaction condition of a compound to be a raw material, and specific examples thereof include an amide compound such as N-methylpyrrolidone, N,N-dimethylformamide, or N,N-dimethylacetamide.

Moreover, it is preferable to perform the reaction using a base such as potassium carbonate or sodium carbonate in the reaction shown in the chemical formula (1-3).

In the reaction shown in the chemical formula (1-3), the amount of the compound (Ij) to be used is preferably 4 molar times or more and more preferably 4 molar times to 8 molar times with respect to the compound (Ii). Further, the amount of the base to be used is preferably 1 molar time or more and more preferably 1 molar time to 6 molar times with respect to the compound (Ij).

The reaction temperature in the reaction shown in the chemical formula (1-3) is preferably in the range of 130° C. to 150° C. and the reaction time thereof is preferably in the range of 18 hours to 36 hours.

In the reaction shown in the chemical formula (1-3), in a case where one kind of compound is used as the compound (Ij), one kind of compound (Ik) is generated from one kind of compound (Ii).

Meanwhile, in a case where plural kinds of compounds are used as the compound (Ij), plural kinds of compounds (Ik) are generated even from one kind of compound (Ii). Further, even when one kind of compound is used as the compound (Ij), plural kinds of compounds (Ik) are generated in a case where plural kinds of compounds (Ii) (mixture of compounds (Ii)) are used. In this manner, in a case where plural kinds of compounds are generated as the compounds (Ik) and some kinds of the compounds are used, a target compound (Ik) may be extracted through concentration, crystallization, reprecipitation, column chromatography, or the like by performing any one of post-treatment operations such as filtration, washing, extraction, pH adjustment, dehydration, concentration, and the like or a combination of two or more kinds thereof. In addition, the extracted compound (Ik) may be purified by performing any one of operations such as crystallization, reprecipitation, column chromatography, extraction, stirring and washing crystals using a solvent, and the like or a combination of two or more kinds thereof once or more times if necessary. Further, the formation rate of the target compound may be improved by adjusting the reaction condition.

It is preferable that the reaction shown in the chemical formula (1-5) be performed using a solvent. The solvent can be appropriately and arbitrarily selected from solvents not prohibiting the reaction in consideration of solubility and the reaction condition of a compound to be a raw material, and an aromatic compound such as toluene or phenol can be exemplified as a specific example of the solvent. In addition, an organic acid such as a propionic acid or the like may be used.

In a case where an organic acid such as a propionic acid or the like is not used as a solvent, it is preferable that the reaction shown in the chemical formula (1-5) be performed using a base such as pyridine or pyrazine.

In the chemical formula (1-5), the total amount of the compounds (Im) and (In) to be used is preferably 2 molar times or more and more preferably 4 molar times to 5 molar times with respect to the compound (Il). Further, the amount of the base to be used is preferably 1 molar time or more and more preferably 4 molar times to 5 molar times with respect to the compound (Il).

In the reaction shown in the chemical formula (1-5), in the case where the reaction is performed using a base such as pyridine or pyrazine, the reaction temperature is preferably in the range of 120° C. to 150° C. and the reaction time is preferably in the range of 6 hours to 36 hours. Meanwhile, in the case where the reaction is performed using an organic acid such as a propionic acid, the reaction temperature is preferably in the range of 130° C. to 150° C. and the reaction time is preferably in the range of 5 hours to 8 hours.

The reaction may be performed while removing water which is secondarily produced using azeotropic dehydration. At this time, a solvent may be appropriately added during the reaction.

In the reaction shown in the chemical formula (1-5), in a case where the same compounds are used as compounds (Im) and (In), it becomes easy to obtain symmetric compounds as the compounds (IA) and (IB) in Ar$^1$ and Ar$^2$.

In contrast, in a case where different compounds are used as the compounds (Im) and (In) or compounds in which Ar$^1$ and Ar$^2$ are groups other than the groups represented by the general formula (I)-11 are used as the compounds (Im) and (In), it becomes easy to obtain asymmetric compounds as the compounds (IA) and (IB) in Ar$^1$ and Ar$^2$.

Further, even in a case of symmetric or asymmetric compounds in Ar$^1$ and Ar$^2$, it is possible to obtain both compounds represented by the general formulae (IA) and (IB) according to the reaction site of the compounds (Il) with the compounds (In) and (Im).

Meanwhile, in a case where compounds in which Ar$^1$ and Ar$^2$ are the same groups represented by the general formulae (I)-11 are used as the compounds (Im) and (In) and only one kind of compound is used as the compound (Il), respectively only one kind of compound represented by the general formula (IA) or (IB) is generated.

In this manner, plural kinds of compounds can be generated as the compounds represented by the general formulae (IA) and (IB). In a case where some kinds of the compounds are used, a target compound may be separated by employing a purifying method described below. Further, the formation rate of the target compound may be improved by adjusting the reaction condition.

In the reaction shown in the chemical formula (1-5), after the reaction is terminated, the general formulae (IA) and (IB) may be extracted by performing a post-treatment using a known technique if necessary. That is, a target compound may be appropriately separated using the same method as that of the case of the compound (Ik) described above if necessary and the formation rate of the target compound may be improved by adjusting the reaction condition.

Structures of the compounds (Ig), (Ii), (Ik), (Il), (IA), and (TB) can be verified using known techniques such as nuclear magnetic resonance (NMR) spectroscopy, mass spectrometry (MS), and infrared spectroscopy (IR).

<Compound 2>

A compound according to the present embodiment is represented by the following general formula (IIA) or (IIB) (hereinafter, these compounds are also simply written as compounds (II) collectively in some cases). Since the compounds (II) are novel fluorescent compounds and have a high absorption coefficient with respect to light having a long wavelength, such light can be sufficiently absorbed by the compounds. Among the compounds (II), the compound represented by the following general formula (IIA) is a syn body and the compound represented by the following general formula (IIB) is an antibody.

[Chem. 26]

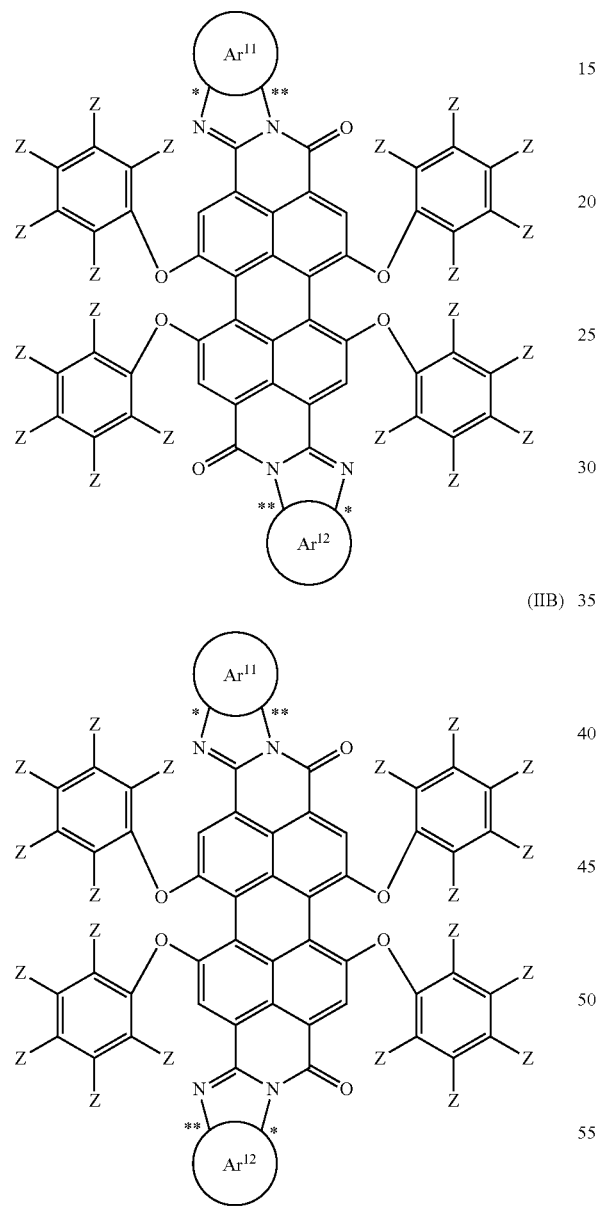

(In the formulae, Z represents a hydrogen atom, an alkyl group, an alkenyl group, an alkynyl group, an aryl group, an alkyl carbonyl amino group, or a group represented by the following general formula (z)-1 or (z)-2, and a plurality of Zs may be the same as or different from one another, but at least one Z represents an alkenyl group, an alkynyl group, an aryl group, an alkyl carbonyl amino group or a group represented by the general formula (z)-1 or (z)-2; $Ar^{11}$ and $Ar^{12}$ each independently represent a group represented by the following general formula (II)-11, (II)-12, or (II)-13; and a bond marked with a symbol "*" is attached to a carbon atom marked with the symbol "*" of the group, and a bond marked with a symbol "" is attached to a carbon atom marked with the symbol "" of the group.)

[Chem. 27]

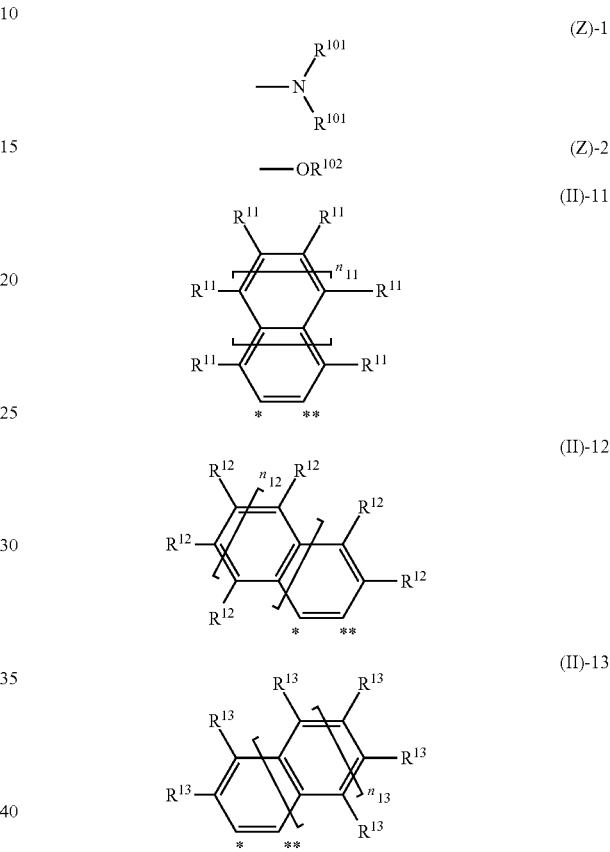

(In the formulae, $R^{101}$ represents a hydrogen atom, an alkyl group, or an aryl group, and two $R^{101}$s may be the same as or different from each other; $R^{102}$ represents a hydrogen atom or an alkyl group; $R^{11}$, $R^{12}$, and $R^{13}$ each independently represent a hydrogen atom or an alkyl group, and a plurality of $R^{11}$s, $R^{12}$s, and $R^{13}$s may be the same as or different from one another; and $n_{11}$ is an integer of 0 to 2, $n_{12}$ and $n_{13}$ are each independently 1 or 2, and a plurality of $n_{11}$s, $n_{12}$s, and $n_{13}$s may be the same as or different from one another.)

In the formulae, Z represents a hydrogen atom, an alkyl group, an alkenyl group, an alkynyl group, an aryl group, an alkyl carbonyl amino group, or a group represented by the general formula (z)-1 or (z)-2. However, at least one Z represents an alkenyl group, an alkynyl group, an aryl group, an alkyl carbonyl amino group, or a group represented by the general formula (z)-1 or (z)-2, and accordingly, all Zs cannot represent a hydrogen atom or an alkyl group. When the compounds (II) include an alkenyl group, an alkynyl group, an aryl group, an alkyl carbonyl amino group, or a group represented by the general formula (z)-1 or (z)-2, light having a sufficiently long wavelength can be absorbed.

In the formulae, $R^{101}$ represents a hydrogen atom, an alkyl group, or an aryl group, and two $R^{101}$s may be the same as or different from each other. That is, the group represented by the general formula (z)-1 is an amino group, a monoalkyl amino group, a dialkyl amino group, a monoaryl amino group, a diaryl amino group, or an alkyl aryl amino group.

The alkyl group in $R^{101}$ may be linear, branched, or cyclic, and the alkyl group may be monocyclic or polycyclic when the alkyl group is cyclic. In addition, the number of carbon atoms of the alkyl group is preferably in the range of 1 to 20 and more preferably in the range of 1 to 10.

The number of carbon atoms of the linear or branched alkyl group is preferably in the range of 1 to 20, and examples of the alkyl group include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, a 1-methylbutyl group, an n-hexyl group, a 2-methylpentyl group, a 3-methylpentyl group, a 2,2-dimethylbutyl group, a 2,3-dimethylbutyl group, an n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, an n-octyl group, an isooctyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an icosyl group.

Among these, the number of carbon atoms of the linear or branched alkyl group is more preferably in the range of 1 to 10.

The number of carbon atoms of the cyclic alkyl group is preferably in the range of 3 to 20 and more preferably in the range of 3 to 10, and examples of the alkyl group include a cyclopropyl group, a cyclobutyl group, a cyclopentyl group, a cyclohexyl group, a cycloheptyl group, a cyclooctyl group, a cyclononyl group, a cyclodecyl group, a norbornyl group, an isobornyl group, a 1-adamantyl group, a 2-adamantyl group, and a tricyclodecyl group.

The aryl group in $R^{101}$ may be monocyclic or polycyclic and the number of carbon atoms thereof is preferably in the range of 6 to 12, and examples thereof include a phenyl group, a 1-naphthyl group, a 2-naphthyl group, an o-toluyl group, an m-toluyl group, a p-toluyl group, and a xylyl group (dimethylphenyl group). Further, one or more hydrogen atoms of these aryl groups may be substituted with an alkyl group. Here, as the alkyl group with which hydrogen atoms are substituted, groups which are the same as the above-described alkyl groups in $R^{101}$ can be exemplified.

The aryl group in $R^{101}$ is preferably monocyclic and more preferably a phenyl group.

It is preferable that $R^{101}$ represent a hydrogen atom, an alkyl group having 1 to 10 carbon atoms, or an aryl group having 6 to 12 carbon atoms.

In the formulae, $R^{102}$ represents a hydrogen atom or an alkyl group. That is, the group represented by the general formula (z)-2 is a hydroxyl group or an alkoxy group.

As the alkyl group in $R^{102}$, groups which are the same as the alkyl groups in $R^{101}$ can be exemplified, and the alkyl group in $R^{102}$ may be the same as or different from the alkyl group in $R^{101}$ in the same molecule.

It is preferable that $R^{102}$ represent an alkyl group having 1 to 10 carbon atoms.

The alkyl group in Z may be linear, branched, or cyclic, and the alkyl group may be monocyclic or polycyclic when the alkyl group is cyclic. Further, the number of carbon atoms of the alkyl group in Z is preferably in the range of 1 to 22, and more preferably in the range of 6 to 18 in terms of improving solubility in a solvent described below.

The number of carbon atoms of the linear or branched alkyl group in Z is preferably in the range of 1 to 22, and examples of the alkyl group include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, a 1-methylbutyl group, an n-hexyl group, a 2-methylpentyl group, a 3-methylpentyl group, a 2,2-dimethylbutyl group, a 2,3-dimethylbutyl group, an n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, an n-octyl group, an isooctyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a henicosyl group, and a docosyl group.

Among these, the number of carbon atoms of the linear or branched alkyl group is more preferably in the range of 6 to 18.

The number of carbon atoms of the cyclic alkyl group in Z is preferably in the range of 3 to 22, and examples of the alkyl group include a cyclopropyl group, a cyclobutyl group, a cyclopentyl group, a cyclohexyl group, a cycloheptyl group, a cyclooctyl group, a cyclononyl group, a cyclodecyl group, a norbornyl group, an isobornyl group, a 1-adamantyl group, a 2-adamantyl group, and a tricyclodecyl group. Further, groups in which one or more hydrogen atoms of these cyclic alkyl groups are substituted with a linear, branched, or cyclic alkyl group can be exemplified. Here, as the linear, branched, or cyclic alkyl group with which hydrogen atoms are substituted, groups which are the same as the above-described alkyl groups in Z can be exemplified.

Among these, the number of carbon atoms of the cyclic alkyl group is more preferably in the range of 6 to 18.

In a case where compounds (II) include an alkyl group as Z, the solubility in a solvent is improved by selecting an appropriate solvent for the compounds (II) in the same manner as the case in which $R^{11}$, $R^{12}$, or $R^{13}$ described below represents an alkyl group. When the compounds (II) with high solubility in a solvent are used, a solar power generation device, described below, whose power generation amount is increased can be more easily obtained. In this case, in a case where the compounds (II) without an alkyl group as Z are used, it is possible to obtain a solar power generation device whose power generation amount is sufficiently high.

The alkenyl group in Z may be linear, branched, or cyclic, and a group in which any one single bond (C—C) between carbon atoms is substituted with a double bond (C═C) can be exemplified as the alkyl group having 2 or more carbon atoms in Z. Preferred examples of the alkenyl group include a vinyl group (ethenyl group, —CH═CH$_2$), an allyl group (2-propenyl group, —CH$_2$—CH═CH$_2$), a 1-propenyl group (—CH═CH—CH$_3$), an isopropenyl group (—C(CH$_3$)═CH$_2$), a 1-butenyl group (—CH═CH—CH$_2$—CH$_3$), a 2-butenyl group (—CH$_2$—CH═CH—CH$_3$), a 3-butenyl group (—CH$_2$—CH$_2$—CH═CH$_2$), a cyclohexenyl group, and a cyclopentenyl group.

The alkynyl group in Z may be linear, branched, or cyclic, and a group in which any one single bond (C—C) between carbon atoms is substituted with a triple bond (C≡C) can be exemplified as the alkyl group having 2 or more carbon atoms in Z. Preferred examples of the alkenyl group include an ethynyl group (—CH≡CH) and a propargyl group (—CH$_2$—C≡CH).

As the aryl group in Z, groups which are the same as the above-described aryl groups in $R^{101}$ can be exemplified.

A group in which one hydrogen atom of an amino group ($-NH_2$) is substituted with an alkyl carbonyl group can be exemplified as the alkyl carbonyl amino group in Z. Further, a monovalent group in which the alkyl group in Z is bonded to a carbon atom of a carbonyl group ($-C(=O)-$) can be exemplified as the alkyl carbonyl group.

As a preferred example of the alkyl carbonyl amino group in Z, a methyl carbonyl amino group ($-NH-C(=O)-CH_3$) or the like can be exemplified.

A plurality (twenty) of Zs may be the same as or different from one another. That is, all Zs may be the same as or different from one another, or some of Zs may be different from one another. In this case, a case where all Zs represent a hydrogen atom or an alkyl group is excluded.

In the case where Z represents an alkenyl group, an alkynyl group, an aryl group, an alkyl carbonyl amino group, or a group represented by the general formula (z)-1 or (z)-2, positions and the number of these Zs in the compounds (I) are not particularly limited. Moreover, in the compounds (II), it is preferable that four benzene ring skeletons to which Z and an oxygen atom are bonded respectively include one or more alkenyl groups, alkynyl groups, aryl groups, alkyl carbonyl amino groups, or groups represented by the general formula (z)-1 or (z)-2 as Z.

In addition, in the compounds (II), when Z is a relatively bulky group, a benzene ring skeleton to which Z is bonded is difficult to rotate using a bond between adjacent oxygen atoms as an axis because of large steric hindrance. For example, a case where a benzene ring skeleton does not rotate while focusing on the benzene ring skeleton in the same position in regard to compounds (II) of two molecules is considered. A group other than a hydrogen atom as Z is bonded to a carbon atom on the second position of the benzene ring skeleton in one compound (II) and all hydrogen atoms as Z are bonded to other carbon atoms. In contrast, a group other than a hydrogen atom as Z is bonded to a carbon atom on the sixth position of the benzene ring skeleton in another compound (II) and all hydrogen atoms as Z are bonded to other carbon atoms. These compounds (II) are differentiated from each other as a stereoisomer even when the groups other than a hydrogen atom are the same as each other. Similarly, a compound (II) in which a group other than a hydrogen atom as Z is bonded to a carbon atom on the third position of the benzene ring skeleton and all hydrogen atoms as Z are bonded to other carbon atoms is differentiated from a compound (II) in which a group other than a hydrogen atom as Z is bonded to a carbon atom on the fifth position of the benzene ring skeleton and all hydrogen atoms as Z are bonded to other carbon atoms as a stereoisomer even when the above-described groups other than a hydrogen atom are the same as each other. In addition, the example described herein is merely an example and the stereoisomer is not limited thereto.

In the formulae, $Ar^{11}$ and $Ar^{12}$ each independently represent a group represented by the general formula (II)-11, (II)-12, or (II)-13.

When $Ar^{11}$ and $Ar^{12}$ each independently represent a group represented by the general formula (II)-11, (II)-12, or (II)-13, the light absorption peak wavelength of the compounds (II) becomes long. Further, the fluorescence quantum yield becomes large.

In the general formulae (IIA) and (IIB), bonds marked with the symbol "*" are attached to carbon atoms marked with the symbol "*" of the group represented by the general formula (II)-11, (II)-12, or (II)-13. That is, when it is described using the general formula (IIA) as an example, the bond stretched from N (nitrogen atom) of "$-C(=N)-$" toward $Ar^{11}$ is attached to the carbon atom marked with the symbol "*" of any one of the above-described groups as $Ar^1$, and the bond stretched from N (nitrogen atom) of "$-C(=N)-$" toward $Ar^{12}$ is attached to the carbon atom marked with the symbol "*" of any one of the above-described groups as $Ar^{12}$.

Similarly, in the general formulae (IIA) and (IIB), bonds marked with the symbol "" are attached to carbon atoms marked with the symbol "" of the group represented by the general formula (II)-11, (II)-12, or (II)-13. That is, when it is described using the general formula (IIA) as an example, the bond stretched from N (nitrogen atom) of "$-C-N-C(=O)-$" toward $Ar^{11}$ is attached to the carbon atom marked with the symbol "" of any one of the above-described groups as $Ar^{11}$, and the bond stretched from N (nitrogen atom) of "$-C-N-C(=O)-$" toward $Ar^{12}$ is attached to the carbon atom marked with the symbol "" of any one of the above-described groups as $Ar^{12}$.

In the formulae, $R^{11}$, $R^{12}$, and $R^{13}$ each independently represent a hydrogen atom or an alkyl group.

As the alkyl groups in $R^{11}$, $R^{12}$, and $R^{13}$, groups which are the same as the alkyl groups as Z can be exemplified, and the alkyl groups in $R^{11}$, $R^{12}$, and $R^{13}$ may be the same as or different from the alkyl groups in Z in the same molecule.

A plurality of $R^{11}$s, $R^{12}$s, and $R^{13}$s may be the same as or different from one another. For example, in the general formula (II)-11, a plurality ("$2n_{11}+4$") of $R^{11}$s may be the same as or different from one another.

In the case where any one or more $R^{11}$s, $R^{12}$s, or $R^{13}$s, represent an alkyl group, the positions and the number of these alkyl groups in the compounds (II) are not particularly limited.

It is preferable that $R^{11}$, $R^{12}$, and $R^{13}$ each independently represent a hydrogen atom or an alkyl group having 1 to 22 carbon atoms and more preferable that $R^{11}$, $R^{12}$, and $R^{13}$ each independently represent a hydrogen atom or an alkyl group having 6 to 18 carbon atoms.

In a case where the compounds (II) include one or more alkyl groups in a molecule as $R^{11}$, $R^{12}$, or $R^{13}$, the solubility in a solvent is improved by selecting an appropriate solvent. When the compounds (II) with high solubility in a solvent are used, a solar power generation device, described below, whose power generation amount is increased can be more easily obtained. In this case, in a case where the compounds (II) without an alkyl group are used as $R^{11}$, $R^{12}$, or $R^{13}$ are used, it is possible to obtain a solar power generation device whose power generation amount is sufficiently high.

In the formulae, $n_{11}$ represents an integer of 0 to 2, and $n_{12}$ and $n_{13}$ each independently represent 1 or 2. For example, in the general formula (II)-11, when $n_{11}$ is 2, the group represented by the general formula (11)-11 is a group having a structure in which three benzene ring skeletons are condensed. Moreover, when $n_{11}$ is 0, the group represented by the general formula (II)-11 is a group having one benzene ring skeleton.

A plurality of $n_{11}$s, $n_{12}$s, and $n_{13}$s may be the same as or different from one another.

For example, in the general formulae (IIA) and (IIB), when both $Ar^{11}$ and $Ar^{12}$ represent a group represented by the general formula (II)-11, $n_{11}$ in $Ar^{11}$ and $n_{11}$ in $Ar^{12}$ may be the same as or different from each other. The same applies to $n_{12}$ in the general formula (II)-12 and $n_{13}$ in the general formula (II)-13.

The light absorption peak wavelength of the compound (II) tends to be long as $n_{11}$, $n_{12}$, or $n_{13}$ is larger.

Further, it is preferable that $n_{11}$, $n_{12}$, or $n_{13}$ in $Ar^{11}$ and $Ar^{12}$ be the same as each other in terms of facilitating production of the compounds (II) using a production method described below.

The peak wavelength of absorbable light of the compounds (II) is preferably 640 nm or greater, and the absorption wavelength of light becomes sufficiently long by selecting an appropriate structure of the compounds (II) so that the peak wavelength of absorbable light becomes 700 nm or greater.

The peak wavelength of absorbable light of the compounds (II) can be acquired using quantum chemical calculation. At this time, a versatile quantum chemical calculation software can be used and Gaussian 09 (manufactured by Gaussian, Inc.) can be exemplified as the software. In addition, the peak wavelength of light can be acquired by level B3LYP/6-31G of a non-empirical molecular orbital calculation method.

Hereinafter, compounds represented by the following general formulae (3A)-1 to (3A)-6 and (3B)-1 to (3B)-6 as the compounds (II) can be exemplified.

[Chem. 28]

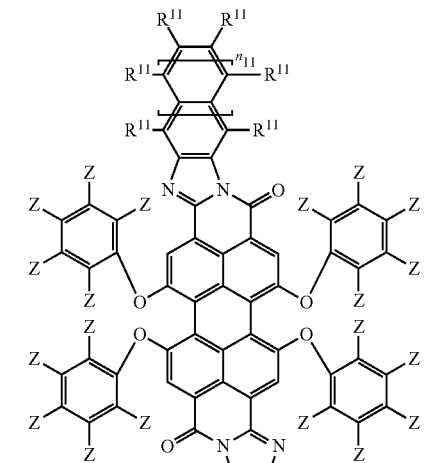

(3A)-1

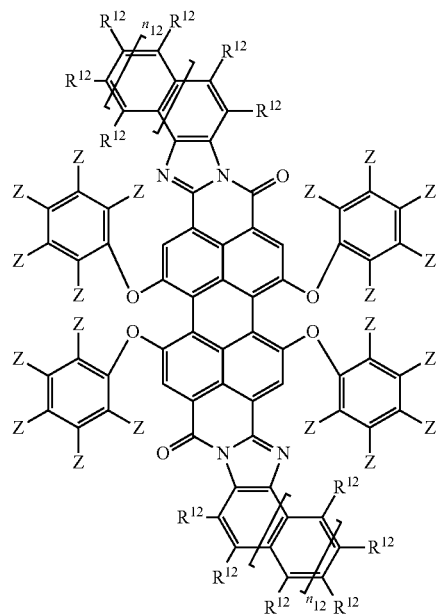

(3A)-2

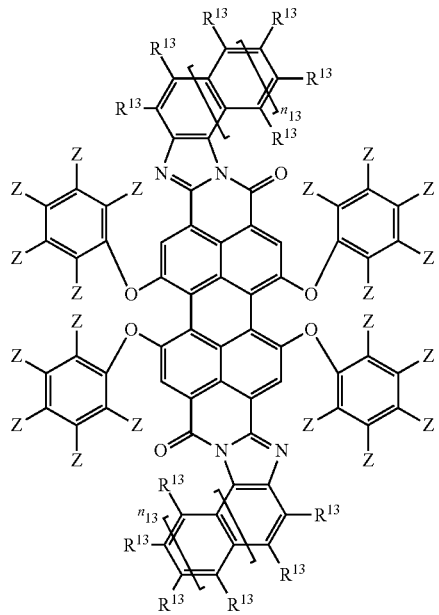

(3A)-3

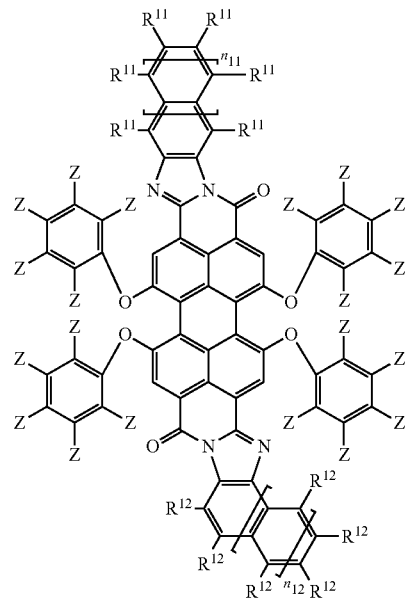

(3A)-4

(In the formulae, Z, $R^{11}$, $R^{12}$, $R^{13}$, $n_{11}$, $n_{12}$, and $n_{13}$ are the same as those described above.)

[Chem. 29]
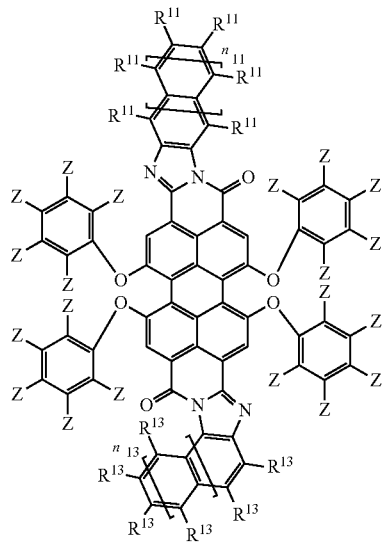
(3A)-5
[Chem. 30]
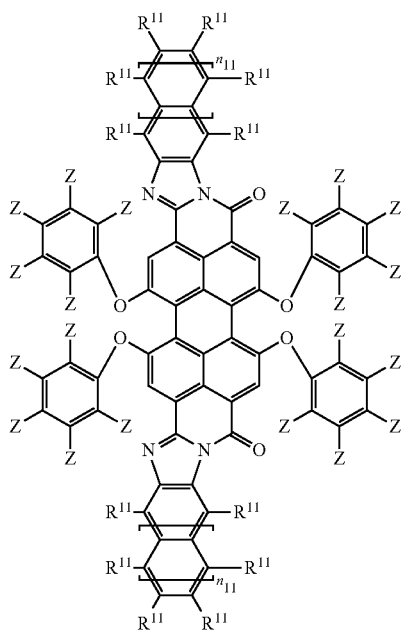
(3B)-1
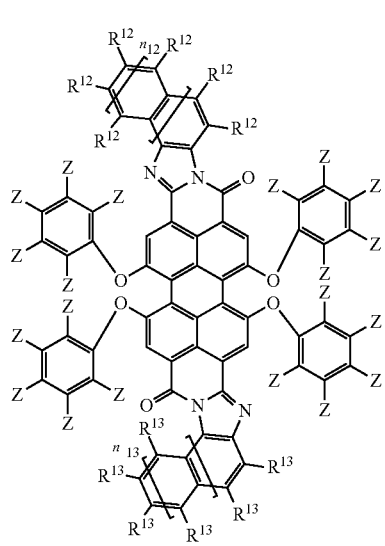
(3A)-6
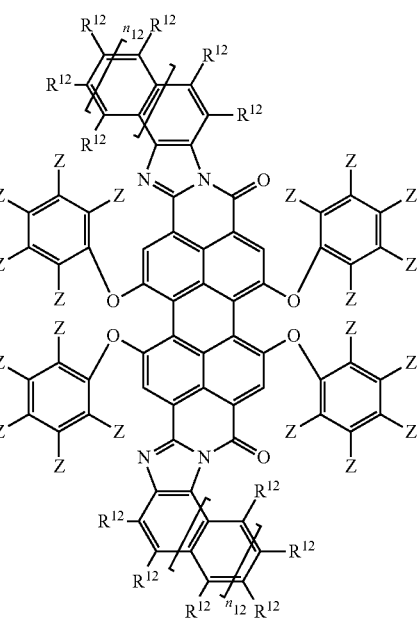
(3B)-2
(In the formulae, Z, $R^{11}$, $R^{12}$, $R^{13}$, $n_{11}$, $n_{12}$, and $n_{13}$ are the same as those described above.)

(3B)-3

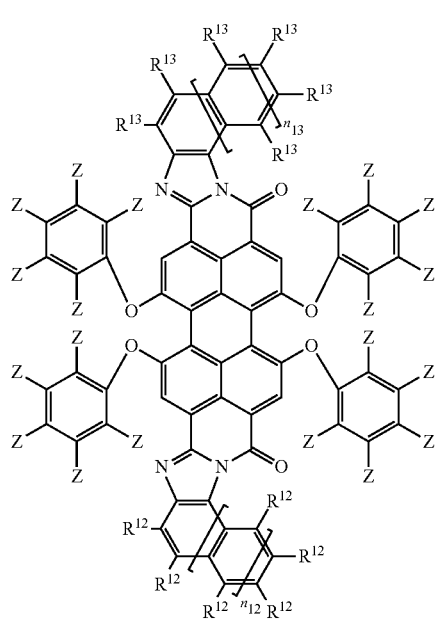

(In the formulae, Z, $R^{11}$, $R^{12}$, $R^{13}$, $n_{11}$, $n_{12}$, and $n_{13}$ are the same as those described above.)

(3B)-4

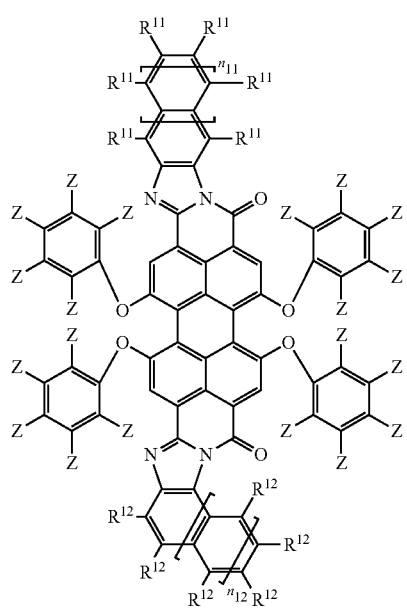

(In the formulae, Z, $R^{11}$, $R^{12}$, $R^{13}$, $n_{11}$, $n_{12}$, and $n_{13}$ are the same as those described above.)

[Chem. 31]

(3B)-5

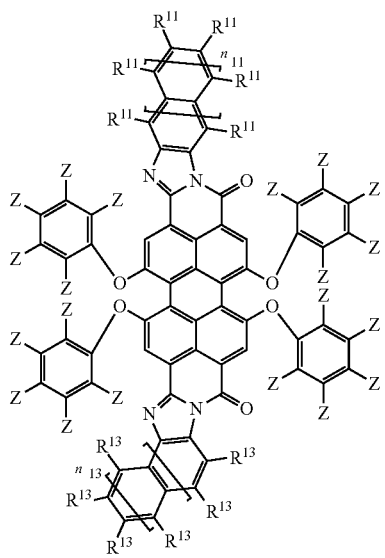

(3B)-6

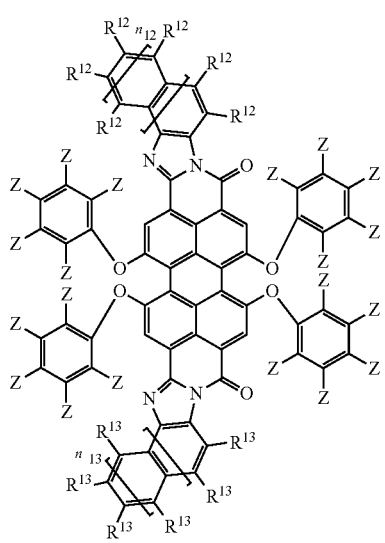

(In the formulae, Z, $R^{11}$, $R^{12}$, $R^{13}$, $n_{11}$, $n_{12}$, and $n_{13}$ are the same as those described above.)

Since the compounds (II) can absorb light having a sufficiently long wavelength, such a solar power generation device has an excellent power generation amount by means of using the compounds (II) as a phosphor in the solar power generation device described below.

The compounds (II) can be produced by a production method including a process of producing compounds (IIb) and a process of producing compounds (II). The process of producing compounds (IIb) is a process of obtaining compounds (hereinafter, these compounds are also simply written as "compounds (IIb)" collectively) represented by the following general formulae (IIAb) and/or (IIBb) by reacting a compound (hereinafter, simply written as the "compound (IIe)") represented by the following general formula (IIe), a compound (hereinafter, simply written as the "compound (IId)") represented by the following general formula (IId), and a compound (hereinafter, simply written as the "compound (IIc)") represented by the following general formula (IIc). The process of producing compounds (II) is a production method including a process of obtaining compounds (II) (hereinafter, simply written as a "process of producing compounds (II)") by reacting a compound (IIb) and a compound (hereinafter, simply written as the "compound (IIa)") represented by the following general formula (IIa). However, the production method exemplified here is merely an example and the method of producing compounds (II) is not limited thereto.

Moreover, in the following reaction formulae, an example in which both compounds represented by the general formulae (IIAb) and (IIBb) are generated is exemplified as compounds (IIb), but only either of the compounds is generated in some cases as described above. In addition, a compound (II) represented by the general formula (IIA) is generated from a compound (IIb) represented by the general formula (IIAb) and a compound (II) represented by the general formula (IIB) is generated from a compound (IIb) represented by the general formula (IIBb).

[Chem. 32]

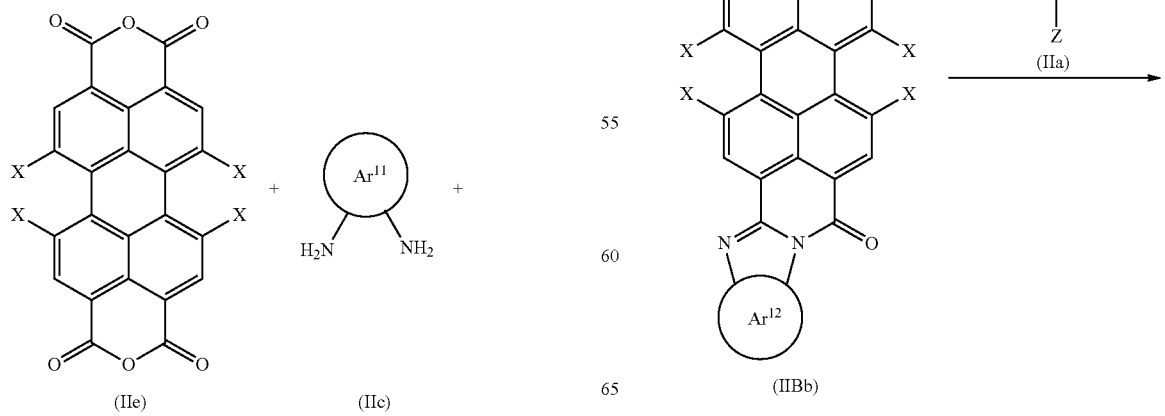

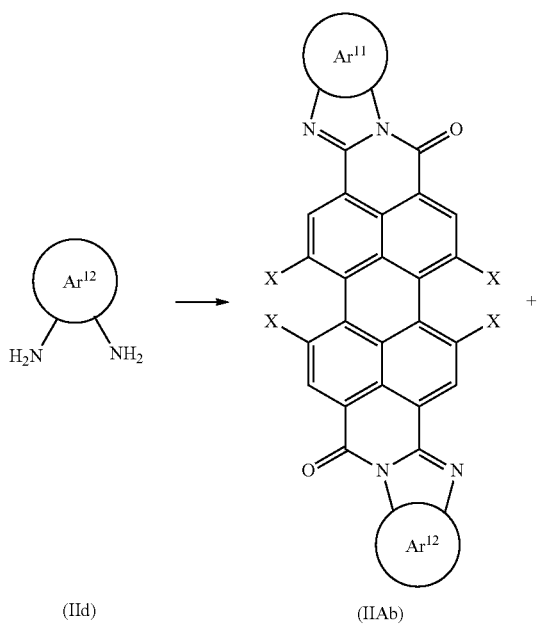

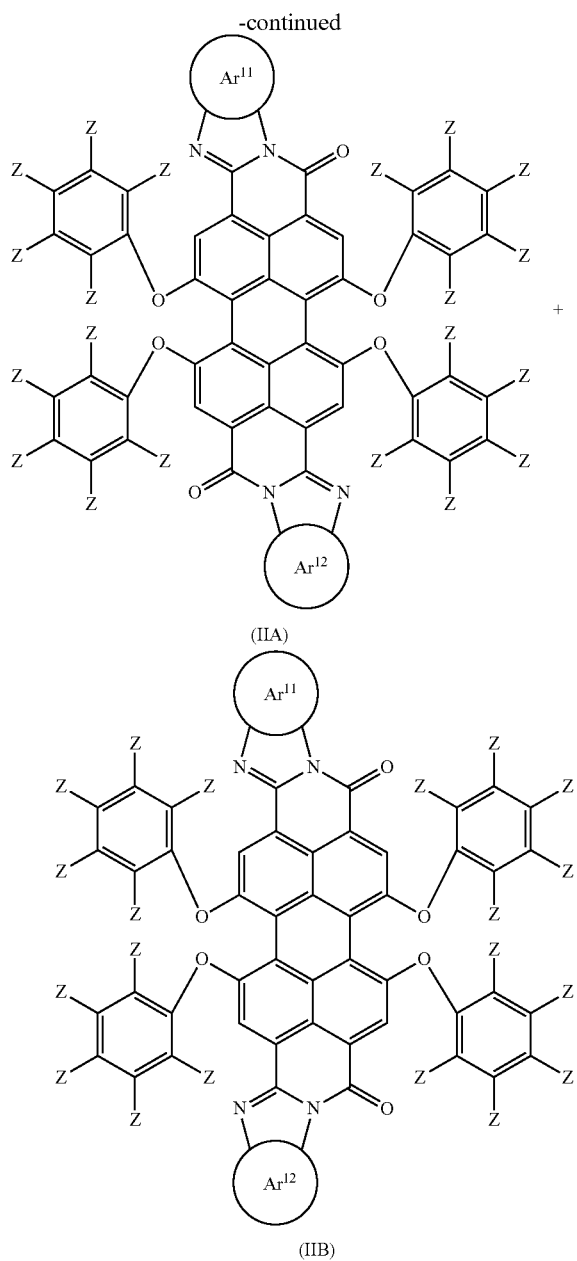

(IIA)

(IIB)

(In the formulae, Z, $Ar^{11}$, and $Ar^{12}$ are the same as those described above; and X represents a halogen atom.)

In the process of producing the compound (IIb), the compounds (IIc), (IId), and (IIe) are reacted. Such reaction is a dehydration condensation reaction.

In the compound (IIc), $Ar^{11}$ is the same as $Ar^{11}$ in the general formulae (IIA) and (IIB). Further, among two amino groups (—NH$_2$) bonded to $Ar^{11}$, a bond made by one amino group being bonded to $Ar^{11}$ is a bond marked with the symbol "*" in the general formulae (IIA) and (IIB) and another bond made by another amino group being bonded to $Ar^{11}$ is a bond marked with the symbol "**" in the general formulae (IIA) and (IIB).

In the compound (IId), $Ar^{12}$ is the same as $Ar^{12}$ in the general formulae (IIA) and (IIB). Further, among two amino groups (—NH$_2$) bonded to $Ar^{12}$, a bond made by one amino group being bonded to $Ar^{12}$ is a bond marked with the symbol "*" in the general formulae (IIA) and (IIB) and another bond made by another amino group being bonded to $Ar^{12}$ is a bond marked with the symbol "**" in the general formulae (IIA) and (IIB).

The compounds (IIc) and (IId) may be the same as or different from each other and may be appropriately selected according to the structures of target compounds (II).

In the compound (IIe), X represents a halogen atom, and preferably a chlorine atom, a bromine atom, or an iodine atom, and a plurality (four) of Xs may be the same as or different from one another, but it is preferable that all of Xs be the same as one another.

In the process of producing the compound (IIb), it is preferable to perform a reaction using a solvent. The solvent can be appropriately and arbitrarily selected from solvents not prohibiting the reaction in consideration of solubility and the reaction condition of a compound to be a raw material, and an aromatic compound such as toluene or phenol can be exemplified as a specific example of the solvent. In addition, an organic acid such as a propionic acid or the like may be used.

In the process of producing the compound (IIb), in a case where an organic acid such as a propionic acid or the like is not used as a solvent, it is preferable that the reaction be performed using a base such as pyridine or pyrazine.

In the process of producing the compound (IIb), the total amount of the compounds (IIc) and (IId) to be used is preferably 2 molar times or more and more preferably 4 molar times to 5 molar times with respect to the compound (IIe). Further, the amount of the base to be used is preferably 1 molar time or more and more preferably 4 molar times to 5 molar times with respect to the compound (IIe).

In the process of producing the compound (IIb), in the case where the reaction is performed using a base such as pyridine or pyrazine, the reaction temperature is preferably in the range of 120° C. to 150° C. and the reaction time is preferably in the range of 6 hours to 36 hours. Meanwhile, in the case where the reaction is performed using an organic acid such as a propionic acid, the reaction temperature is preferably in the range of 130° C. to 150° C. and the reaction time is preferably in the range of 5 hours to 8 hours.

The reaction may be performed while removing water which is secondarily produced using azeotropic dehydration. At this time, a solvent may be appropriately added during the reaction.

In the process of producing the compound (IIb), in a case where the same compounds are used as compounds (IIc) and (IId), it becomes easy to obtain symmetric compounds (IIb) in $Ar^{11}$ and $Ar^{12}$. Symmetric compounds (II) in $Ar^{11}$ and $Ar^{12}$ can be obtained from the compounds (IIb) having such a symmetric structure.

In contrast, in a case where different compounds are used as the compounds (IIc) and (IId) or compounds in which $Ar^{11}$ and $Ar^{12}$ are groups other than the groups represented by the general formula (II)-11 are used as the compounds (IIc) and (IId), it becomes easy to obtain asymmetric compounds (IIb) in $Ar^{11}$ and $Ar^{12}$ and asymmetric compounds (II) in $Ar^{11}$ and $Ar^{12}$ can be obtained from the compounds (IIb) having such an asymmetric structure.

Further, even in a case of symmetric or asymmetric compounds in $Ar^{11}$ and $Ar^{12}$, it is possible to obtain both compounds represented by the general formulae (IIAb) and (IIBb) as compounds (IIb) according to the reaction site of the compounds (IIe) with the compounds (IIc) and (IId).

Meanwhile, in a case where compounds in which $Ar^{11}$ and $Ar^{12}$ are the same groups represented by the general formula (II)-11 are used as the compounds (IIc) and (IId) and only one kind of compound is used as the compound (IIe), respectively only one kind of compound represented by the general formula (IIAb) or (IIBb) is generated as the compounds (IIb).

In this manner, plural kinds of compounds can be generated as the compounds (IIb). In a case where some kinds of the compounds are used, a target compound may be separated by employing a purifying method described below. Further, the formation rate of the target compound may be improved by adjusting the reaction condition.

In the process of producing the compound (IIb), after the reaction is terminated, the compound (IIb) may be extracted by performing a post-treatment according to the necessity using a known technique. That is, the compound (IIb) may be extracted through concentration, crystallization, reprecipitation, column chromatography, or the like by appropriately performing any one of post-treatment operations such as filtration, washing, extraction, pH adjustment, dehydration, concentration, and the like or a combination of two or more kinds thereof if necessary. In addition, the extracted compound (IIb) may be purified by performing any one of operations such as crystallization, reprecipitation, column chromatography, extraction, stirring and washing crystals using a solvent, and the like or a combination of two or more kinds thereof once or more times if necessary.

In the process of producing the compound (IIb), after the reaction is terminated and the post-treatment is performed if necessary, the process of producing the compound (II) may be continuously performed without extracting the compound (IIb).

In the process of producing the compound (II), the compounds (IIa) and (IIb) are reacted.

In the compound (IIa), Z is the same as Z in the general formulae (IIA) and (IIB). In a case where a product of the compound (IIb) is commercially available, the process of producing the compound (IIb) can be omitted by means of using the product of the compound (IIb).

In the process of producing the compound (II), it is preferable to perform a reaction using a solvent. The solvent can be appropriately and arbitrarily selected from solvents not prohibiting the reaction in consideration of solubility and the reaction condition of a compound to be a raw material, and specific examples thereof include an amide compound such as N-methylpyrrolidone, N,N-dimethylformamide, or N,N-dimethylacetamide.

Moreover, it is preferable to perform the reaction using a base such as potassium carbonate or sodium carbonate in the process of producing the compound (II).

In the process of producing the compound (II), the amount of the compound (IIa) to be used is preferably 4 molar times or more and more preferably 4 molar times to 8 molar times with respect to the compound (IIb). Further, the amount of the base to be used is preferably 1 molar time or more and more preferably 1 molar time to 6 molar times with respect to the compound (IIa).

The reaction temperature of the reaction in the process of producing the compound (II) is preferably in the range of 130° C. to 150° C. and the reaction time thereof is preferably in the range of 18 hours to 36 hours.

In the process of producing the compound (II), in a case where one kind of compound is used as the compound (IIa), one kind of compound (II) is generated from one kind of compound (IIb).

Meanwhile, in a case where plural kinds of compounds are used as the compound (IIa), plural kinds of compounds (II) are generated even from one kind of compound (Ib). Further, even when one kind of compound is used as the compound (IIa), plural kinds of compounds (II) are generated in a case where plural kinds of compounds (IIb) (mixture of compounds (IIb)) are used. In this manner, in a case where plural kinds of compounds are generated as the compounds (II) and some kinds of the compounds are used, a target compound may be separated using the same method as that of the case of the above-described compound (IIb) and the formation rate of the target compound may be improved by adjusting the reaction condition.

In the process of producing the compound (II), after the reaction is terminated, the compound (II) may be extracted and then the extracted compound (II) may be purified using the same method as that of the case of the process of producing the compound (IIb).

Structures of the compounds (II) and (IIb) can be verified using known techniques such as nuclear magnetic resonance (NMR) spectroscopy, mass spectrometry (MS), and infrared spectroscopy (IR).

<Solar Cell Module>

A solar cell module according to the present invention uses the compound (I) or the compound (II) described above. A configuration in which solar light is absorbed by the compound (I) or the compound (II), radiation light generated from the compounds (I) or the compound (II) is collected, and the collected light is introduced to a solar cell element can be exemplified.

As such a solar cell module, a solar cell module including a light guide which includes a light incident surface and a light emitting surface whose area is smaller than that of the light incident surface; and a solar cell element which receives light emitted from the light emitting surface and generates power can be exemplified. The light guide further contains the compounds (I) and radiation light from the compound (I) or the compound (II), which is generated by incident light on the light incident surface being absorbed by the compound (I) or the compound (II), is referred to as the emitted light.

The solar cell module according to the present embodiment has an excellent power generation amount by using the compound (I) or the compound (II).

Hereinafter, the solar cell module according to the present embodiment will be described in detail with reference to the accompanying drawings. Further, in the drawings below, in order for each constituent element to have recognizable size, the scale of each constituent element is appropriately changed.

Figure 2:
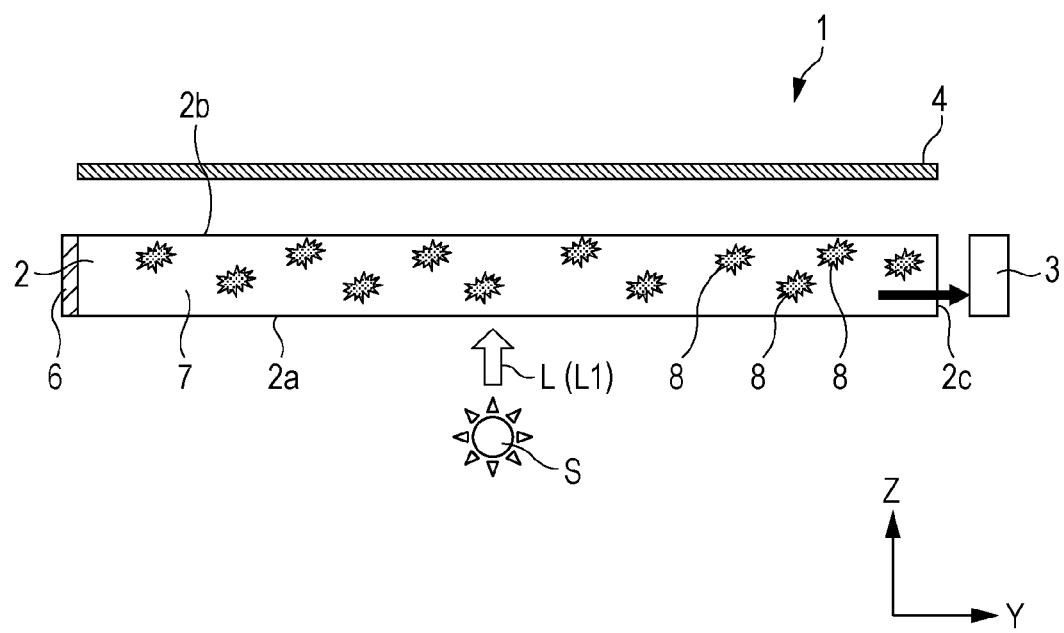
FIG. 2 is a cross-sectional view of the solar cell module according to the present invention.

FIG. 1 is a view schematically illustrating a configuration of an embodiment of a solar cell module according to the present embodiment and FIG. 2 is a cross-sectional view of such a solar cell module.

A solar cell module 1 illustrated in FIG. 1 includes a light collector 2 having a rectangular planar shape, a solar cell element 3, a reflector 4, and a frame 5. The light collector 2 is provided so as to face a sun S. The solar cell element 3 is provided on the end surface of the light collector 2. The reflector 4 is provided on the rear surface side of the light collector 2.

The light collector 2 is a light guide introducing emitted light to the solar cell element 3. In addition, the solar cell element 3 receives light emitted from a first end surface 2c of the light collector 2. The frame 5 holds the light collector 2 and the solar cell element 3 integrally.

The light collector 2 includes a main surface 2a, a rear surface 2b, the first end surface 2c, and other end surfaces as illustrated in FIGS. 1 and 2. The main surface 2a is a light incident surface. The rear surface 2b is positioned on the opposite side to the main surface 2a. The first end surface 2c is a light emitting surface. In the present embodiment, a reflective layer 6 is provided on the end surfaces other than the first end surface 2c.

In the light collector 2, the first end surface 2c has an area smaller than that of the main surface 2a. In this manner, light collection efficiency for the solar cell element 3 is improved and the power generation amount of the solar cell module 1 is further increased.

As illustrated in FIG. 2, the light collector 2 is configured such that a phosphor 8 is dispersed in a transparent base material 7.

The transparent base material 7 includes an acrylic resin such as polymethylmethacrylate (PMMA); an organic material with high transparency such as polycarbonate; and an inorganic material having high transparency such as glass.

As the transparent base material 7, a base material having a transmittance of preferably 90% or higher and more preferably 93% or higher with respect to light having a wavelength region of 360 nm to 800 nm so that external light can be effectively captured can be exemplified. Moreover, preferred examples of the transparent base material 7 include a substrate formed of an acrylic resin such as PMMA, a silicon resin substrate, and a quartz substrate in terms that the transmittance of light having a wide wavelength region is high.

In the present embodiment, the compound (I) or the compound (II) is used as the phosphor 8.

The phosphor 8 is substantially uniformly dispersed in the transparent base material 7.

The compounds (I) and (II) can be used singly or in combination of two or more kinds thereof.

As the phosphor 8, known phosphors other than the compounds (I) and (II) may be used in combination.

As the phosphors other than the compounds (I) and (II), light functional materials that absorb UV light or visible light, emits visible light or infrared light, and performs radiation can be exemplified. Moreover, the visible light indicates light having a wavelength region of 380 nm to 750 nm, the UV light indicates light having a wavelength region of less than 380 nm, and infrared light indicates light having a wavelength region greater than 750 nm.

The phosphors other than the compounds (I) and (II) may be either of inorganic phosphors or organic phosphors.

Examples of the organic phosphors include a coumarin-based dye, a perylene-based dye, a phthalocyanine-based dye, a stilbene-based dye, a cyanine-based dye, a polyphenylene-based dye, a xanthene-based dye, a pyridine-based dye, an oxazine-based dye, a chrysene-based dye, a thioflavin-based dye, a pyrene-based dye, an anthracene-based dye, an acridone-based dye, an acridine-based dye, a fluorene-based dye, a terphenyl-based dye, an ethene-based dye, a butadiene-based dye, a hexatriene-based dye, an oxazole-based dye, a diphenylmethane-based dye, a triphenylmethane-based dye, a thiazole-based dye, a thiazine-based dye, a naphthalimide-based dye, and an anthraquinone-based dye.

Specific examples of the organic phosphors include coumarin-based dyes such as 3-(2'-benzothiazolyl)-7-diethylaminocoumarin (Coumarin 6), 3-(2'-benzoimidazolyl)-7-N,N-diethylaminocoumarin (Coumarin 7), 3-(2'-N-methylbenzoimidazolyl)-7-N,N-dimethylaminocoumarin (Coumarin 30), and 2,3,5,6-1H,4H-tetrahydro-8-trifluoromethylquinolizine(9,9a,1-gh)coumarin (Coumarin 153); Basic Yellow 51 which is a coumarin-based dye; naphthalimide-based dyes such as Solvent Yellow 11 and Solvent Yellow 116; rodamine-based dyes such as Rodamine B, Rodamine 6G, Rodamine 3B, Rodamine 101, Rodamine 110, sulforodamine, Basic Violet 11, and Basic Red 2; pyridine-based dyes such as 1-ethyl-2-[4-(p-dimethylaminophenyl)-1,3-butadienyl]pyridinium-perchlorate (Pyridine 1); cyanine-based dyes; and oxazine-based dyes.

Further, in addition to these described above, substances having fluorescence using various dyes such as direct dyes, acidic dyes, basic dyes, and disperse dyes can be used.

Examples of the inorganic phosphors include red light emitting phosphors such as $GdBO_3$:Eu, $Gd_2O_3$:Eu, $Gd_2O_2S$:Eu, $Gd_3Al_5O_{12}$: Eu, $Gd_3Ga_5O_{12}$: Eu, $GdVO_4$: Eu, $Gd_3Ga_5O_{12}$: Ce, Cr, $Y_2O_3$: Eu, $Y_2O_2S$:Eu, $La_2O_3$:Eu, $La_2O_2S$:Eu, $InBO_3$:Eu, and $(Y,In)BO_3$:Eu; green light emitting phosphors such as $Gd_2O_3$:Tb, $Gd_2O_2S$:Tb, $Gd_2O_2S$:Pr, $Gd_3Al_5O_{12}$:Tb, $Gd_3Ga_5O_{12}$: Tb, $Y_2O_3$: Tb, $Y_2O_2S$: Tb, $Y_2O_2S$:Tb, Dy, $La_2O_2S$:Tb, ZnS:Cu, ZnS:Cu, Au, $Zn_2SiO_4$:Mn, $InBO_3$:Tb, and $MgGa_2O_4$:Mn; and blue light emitting phosphors such as $YAlO_3$:Ce, $Y_2SiO_5$:Ce, $Gd_2SiO_5$:Ce, $YTaO_4$:Nb, BaFCl:Eu, ZnS:Ag, $CaWO_4$, $CdWO_4$, $ZnWO_4$, $MgWO_4$, $Sr_5(PO_4)_3Cl$:Eu, and $YPO_4$:Cl.

The phosphors other than the compounds (I) and (II) may be used singly or in combination of two or more kinds thereof.

In a case where two or more kinds of phosphors 8 are used in combination, a configuration in which light obtained by allowing energy to be moved among these phosphors 8 due to Foerster mechanism and by being radiated from the phosphor 8 whose peak wavelength of the emission spectrum is maximum is set as emitted light to the solar cell element 3 may be employed. In this case, the compounds (I) and (II) can be used as one or more kinds of phosphors 8 among plural kinds of combined phosphors 8, and phosphors 8 to be combined can be arbitrarily selected from the compounds (I) and (II).

The Foerster mechanism is a mechanism in which excitation energy is directly moved between adjacent two phosphors due to electron resonance without processes of generating and absorbing light. Since the energy movement between phosphors due to the Foerster mechanism occurs without the processes of generating and absorbing light, the energy movement efficiency can be substantially 100% under the optimum conditions and energy loss is small. Accordingly, this contributes to improvement of power generation efficiency for the solar cell module. In order to efficiently perform power generation by suppressing energy loss, the density of phosphors 8 to be combined in the transparent base material 7 may be increased.

In addition, energy movement due to the Foerster mechanism is excited by light emitting materials such as a phosphor and by external light, but energy movement occurs in a non-light emitting body that deactivates without generating light. Therefore, such a non-light emitting body may be dispersed in the transparent base material 7 as a light functional material in addition to the phosphor 8.

Since the light collecting efficiency for the solar cell element 3 is improved and the power generation amount of the solar cell module 1 is further increased, the ratio of the compounds (I) or (II) occupied in the total amount of the phosphor 8 in the transparent base material 7 is preferably 5% by mass or more. It is preferable that the ratio of the compounds (I) or (II) occupied in the total amount of the phosphor 8 in the transparent base material 7 be appropriately adjusted according to the number of other phosphors to be combined with the compounds (I) or (II) or the light absorption peak wavelength.

The light collector 2 formed by the phosphor 8 being dispersed in the transparent base material 7 can be obtained using the following method. A resin composition containing a raw material monomer constituting the transparent base material 7 and a phosphor 8 is prepared, and the resin composition is cured in a state in which the phosphor 8 is dispersed. The method of curing the resin composition may be selected according to the kind of raw material monomer.

In the light collector 2, the content of the phosphor 8 is preferably in the range of 0.001% by mass to 0.04% by mass with respect to the transparent base material 7. When the content thereof is more than or equal to the lower limit, the absorption amount of solar light in the light collector 2 is improved and the power generation amount of the solar cell module 1 is further increased. In addition, when the content thereof is less than or equal to the upper limit, the light collecting efficiency for the solar cell element 3 is improved and the power generation amount of the solar cell module 1 is further increased.

The main surface 2a and the rear surface 2b of the light collector 2 are parallel to each other and flat. The reflective layer 6 that reflects light (light radiated from the phosphor 8), which travels toward the outside from the inside of the light collector 2, toward the inside of the light collector 2 is provided on all end surfaces other than the first end surface 2c of the light collector 2 in a contact manner indirectly with an air layer or directly without an air layer.

As the reflective layer 6, a reflective layer formed of a film of a metal such as silver or aluminum or a reflective layer formed of a dielectric multilayer film such as Enhanced Specular Reflector (ESR) reflective film (manufactured by 3M Company) can be exemplified. Further, the reflective layer may be a mirror reflective layer that mirror-reflects incident light or a scattering reflective layer that scatters and reflects incident light. In a case where a scattering reflective layer is used for the reflective layer, since the light amount of light directly travelling toward the direction of the solar cell element 3 is increased, the light collecting efficiency for the solar cell element 3 is improved and the power generation amount of the solar cell module 1 is further increased. Further, since reflected light is scattered, a change in the power generation amount according to the time or the season is averaged. In addition, as the scattering reflective layer, a layer formed of micro-foamed PET (polyethylene terephthalate, manufactured by Furukawa Electric Co., Ltd.) can be exemplified.

The reflector 4 can be set to be the same as the reflective layer 6 except that the shapes thereof are different from each other.

Further, the reflector 4 can be set to be a plate that reflects some of incident light L1 incident on the light collector 2, among light (solar light L) from the sun S as reflected light in a predetermined direction of the incident light L1 (solar light L) on an incident light path side with respect to the normal line on the main surface 2a of the light collector 2.

When the reflector 4 is provided, the light collecting efficiency for the solar cell element 3 is improved and the power generation amount of the solar cell module 1 is further increased.

As the reflector 4 that reflects some of the incident light L1 as reflected light in the predetermined direction, a retro-reflector or an off-axis reflector can be exemplified.

As the retro-reflector, a plate having a prism layer (corner cube array) having multiple shapes of a prism on which three planes are formed through an air layer on the surface of a base material formed of a resin can be exemplified. As commercially available products of the retro-reflective plat, a high intensity grade HIP high luminance reflective sheet, a diamond grade DG ultrahigh luminance reflective sheet (both manufactured by 3M Company), and a prism type ultrahigh luminance retro-reflective sheet (manufactured by Nippon Carbide Industries Co., Ltd.) can be exemplified.

Further, as the retro-reflector, a plate configured such that incident light is refracted by glass beads, reflected on the reflective layer on the backside, and returns to the incident direction again can be exemplified. In addition, examples of the commercially available products thereof include an engineer grade EGP normal reflective sheet (manufactured by 3M Company), a sealed lens type retro-reflective sheet, and a capsule lens type retro-reflective sheet (both manufactured by Nippon Carbide Industries Co., Ltd.).

As the off-axis reflector, a plate in which one surface of a substrate such as an acrylic plate has a prism shape, a reflective material such as aluminum or silver is deposited on the prism surface to form a reflection surface, and the surface is coated with a transparent protective layer can be exemplified. Further, a plate formed of a dielectric multilayer film obtained by alternately laminating a high refractive index layer and a low refractive index layer to form a multilayer film of a dielectric for each of optical film thickness of a ¼ wavelength and slicing (cutting out) the multilayer film at a predetermined angle can be exemplified. A plate in which reflector-like particles are aligned toward a predetermined direction in a transparent base material can be exemplified.

In the solar cell element 3, a light receiving surface is arranged so as to face the first end surface 2c of the light collector 2 and is preferably optically bonded to the first end surface 2c.

The solar cell element 3 may be a known element and examples of the solar cell element include a silicon-based solar cell, a compound-based solar cell, a quantum dot solar cell, and an organic solar cell. Among these, it is preferable that a compound-based solar cell using a compound semiconductor or a quantum dot solar cell be used for the solar cell element 3 in terms of power generation with higher efficiency.

Examples of the compound-based solar cell include solar cells using InGaP, GaAs, InGaAs, AlGaAs, $Cu(In,Ga)Se_2$, $Cu(In,Ga)(Se,S)_2$, $CuInS_2$, CdTe, CdS, and the like.

Examples of the quantum solar cell include solar cells using Si, InGaAs, and the like.

However, depending on the cost and usage, other kinds of solar cells such as a silicon-based solar cell and an organic solar cell is preferably used in some cases.

Further, in FIGS. 1 and 2, an example in which the solar cell element 3 is provided on only one first end surface 2c of the light collector 2 is illustrated, but the solar cell element 3 may be provided on plural end surfaces of the light collector 2. In a case where the solar cell element 3 is provided on some end surfaces (one side, two sides, or three sides) of the light collector 2, it is preferable to provide the reflective layer 6 on end surfaces on which the solar cell element 3 is not provided.

In the frame 5 illustrated in FIG. 2, the main surface 2a of the light collector 2 faces outside, four peripheries of the light collector 2 are held in such a state, and the solar cell element 3 is held together with the light collector 2. The frame 5 may be a frame made of aluminum or the like. A transparent member such as glass may be fitted into an opening portion 5a with the main surface 2a of the light collector 2 facing the outside. With such a configuration, in the light collector 2, the main surface 2a facing the outside from the frame 5 is a light incident surface and the first end surface 2c of the light collector 2 is a light emitting surface. Moreover, some of the external light (solar light) incident from the main surface 2a is incident on the reflector 4 by transmitting through the rear surface 2b.

The solar cell module 1 is provided by allowing the main surface 2a of the light collector 2 to face the sun S as illustrated in FIGS. 1 and 2. Further, in the solar cell module 1, some of light (solar light L) from the sun S is received on the main surface 2a of the light collector 2 as the incident light L1, the incident light L1 is absorbed by the phosphor 8 in the light collector 2, and the phosphor 8 emits light. The radiation light generated at this time from the phosphor 8 propagates through the transparent base material 7 of the light collector 2, is emitted from the first end surface 2c, and introduced to the solar cell element 3. In this manner, the solar cell element 3 generates power by receiving the emitted light.

In addition, in the present embodiment, an example in which the phosphor 8 is dispersed in the transparent base material 7 is described as the light collector 2, but the light collector is not limited to such a configuration. For example, a configuration illustrated in FIG. 3A or 3B may be employed.

Figure 3A:
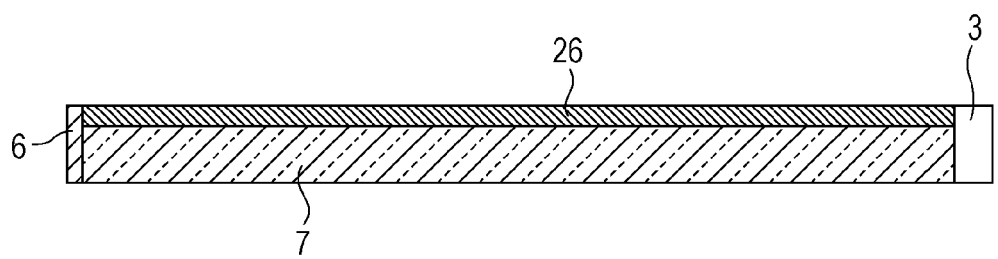
FIG. 3A is a cross-sectional side view illustrating a modification example of a light collector of the solar cell module according to the present invention.

In the light collector illustrated in FIG. 3A, a phosphor layer 26 is formed by coating the surface of a plate-like transparent base material 7 with a coating material to which a phosphor (not illustrated) is dispersed. The transparent base material 7 may be an acrylic plate or the like. The coating material contains a phosphor and a transparent resin to which the phosphor is dispersed. That is, the transparent resin in the coating material becomes a transparent base material that uniformly disperses a phosphor.

Figure 3B:
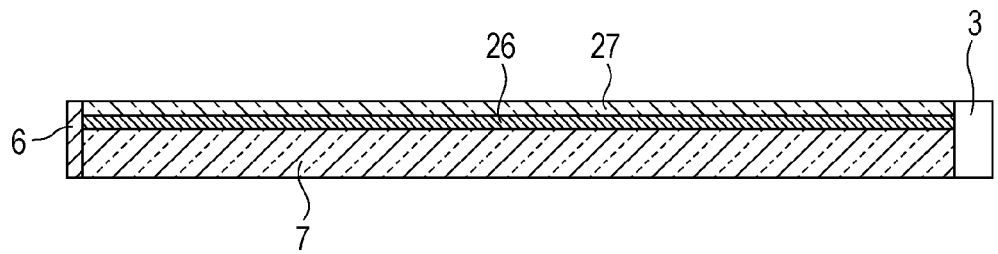
FIG. 3B is a cross-sectional side view illustrating a modification example of the light collector of the solar cell module according to the present invention.

The light collector illustrated in FIG. 3B is further provided with a transparent protective layer (transparent layer) 27 on the surface of the phosphor layer 26 (surface on the opposite side of the transparent base material 7).

Various transparent resins can be exemplified as the materials of the transparent protective layer 27. For example, the transparent protective layer 27 is formed by laminating a transparent resin film formed of polyethylene terephthalate (PET), polyethylene (PE), polyvinylidene chloride, or polyamide on the phosphor layer 26. Further, the transparent protective layer 27 can be also formed by preparing a coating liquid in which a cellulose derivative such as cellulose acetate, ethyl cellulose, or cellulose acetate butyrate, and a transparent resin such as polyvinyl chloride, polyvinyl acetate, a vinyl chloride-vinyl acetate copolymer, polycarbonate, polyvinyl butyral, polymethyl methacrylate, polyvinyl formal, or polyurethane are dissolved, coating the phosphor layer 26 with the coating liquid, and drying the layer.

Figure 4A:
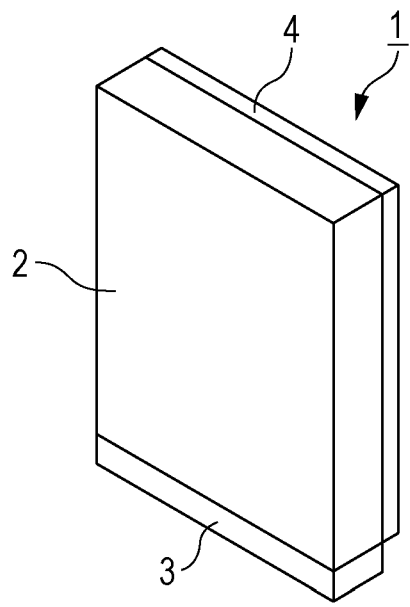
FIG. 4A is a perspective view illustrating a modification example of the solar cell module according to the present invention.

Further, in the solar cell module 1 of the present embodiment, the entire solar cell module is formed to be flat using the flat light collector 2 and the flat reflector 4 illustrated in FIG. 4A as a plate to be provided on a side wall surface formed of a flat surface of a building. However, the entire shape of the solar cell module may be adjusted according to the shape of a surface to be provided.

Figure 4B:
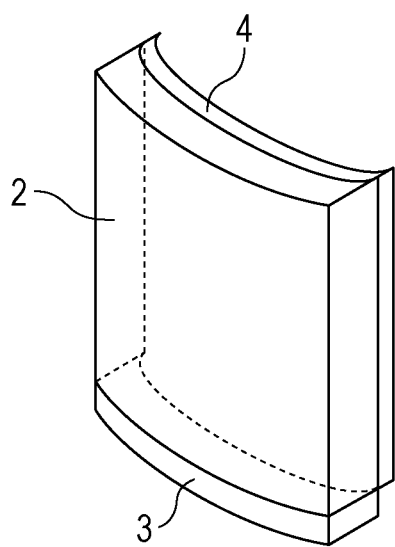
FIG. 4B is a perspective view illustrating a modification example of the solar cell module according to the present invention.

As solar cell modules other than the flat solar cell module, a curved plate-like solar cell module whose entire body is bent as illustrated in FIG. 4B can be exemplified in correspondence with a side surface of a building whose surface has a curved surface shape.

In this case, a plate obtained by coating the surface of a transparent base material with a coating material to which a phosphor is dispersed to form a phosphor layer as illustrated in FIGS. 3A and 3B is preferable as the light collector 2. By forming the transparent base material to have a desired bent shape (curved plate shape), a phosphor layer having a desired bent shape can be formed on the surface. In addition, as the reflector, a plate in which a substrate is formed to have a desired bent shape (curved plate shape) and a retro-reflective sheet is attached onto the surface thereof can be exemplified.

Moreover, the curved plate-like light collector may be provided on a flat side wall of a building. The reflector in this case may have a curved plate shape in the same manner as that described above or may be flat.

Further, the solar cell module can be provided on a roof or a pillar of a building, a telegraph pole, and the like. For example, in a case where the solar cell module is provided on a roof, the entire solar cell module may be formed to have a tile shape or a wave shape by forming the light collector or the reflector to have a tile shape or a wave shape using a technique similar to the technique of forming the curve plate-like solar cell module illustrated in FIG. 4B.

Figure 4C:
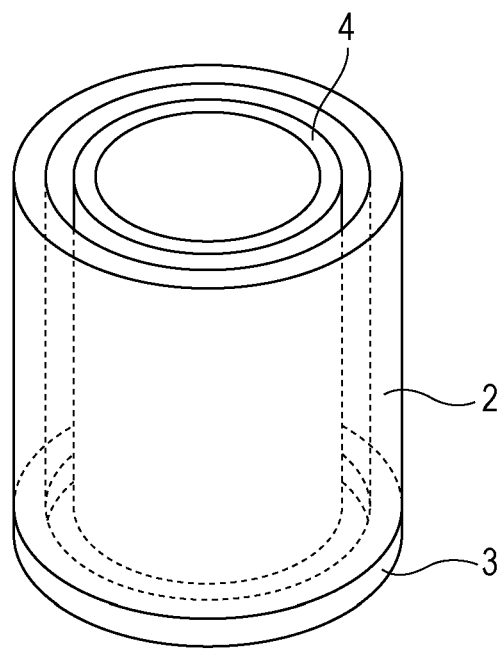
FIG. 4C is a perspective view illustrating a modification example of the solar cell module according to the present invention.

In addition, in a case where the solar cell module is provided on a pillar of a telegraph pole, the solar cell module may have a configuration described below. The solar cell module includes a hollow columnar (cylindrical) light collector 2 illustrated in FIG. 4C; a hollow columnar (cylindrical) reflector 4 arranged on the inner peripheral surface side of the light collector; a hollow columnar (cylindrical) or ring-shaped solar cell element 3 arranged on the end surface of the light collector 2. The entire shape of the solar cell module is a hollow columnar (cylindrical) shape. A solar cell module which is provided by being externally fitted to a pillar is preferable as the solar cell module. In addition, as the shape of a hollow portion, here, an example in which the shape in a direction orthogonal to the shaft is circular is described, but the shape thereof may be appropriately adjusted according to the shape of an object to be externally fitted and is not limited to a circular shape.

Figure 4D:
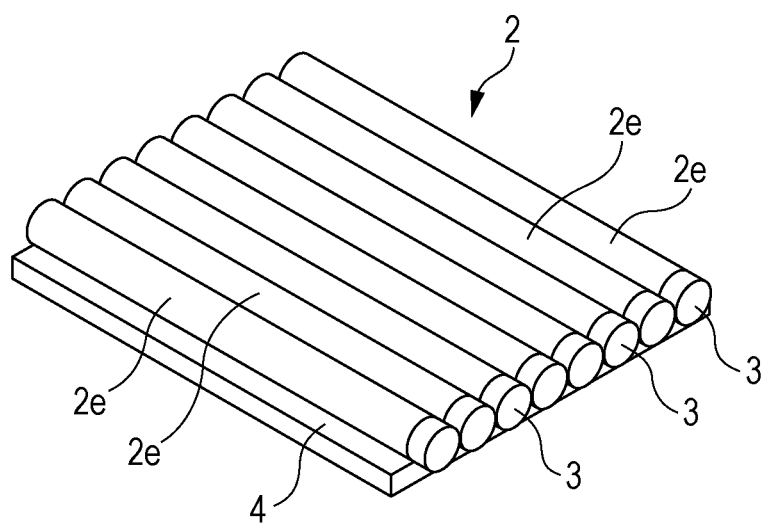
FIG. 4D is a perspective view illustrating a modification example of the solar cell module according to the present invention.

Moreover, columnar light collecting members 2e may be provided by being arranged to make a flat surface as an top plate-like body, that is, a light collector 2 as illustrated in FIG. 4D. The solar cell element 3 is arranged on one end surface (end portion) of the light collecting member 2e. Further, the light collector may be provided by freely changing the surface shape into a curved surface instead of a flat surface through flexible connection of the light collecting members 2e to one another. Further, by forming the shape thereof into a bamboo-blind, adjustment, for example, collecting light by expanding the light collector when needed or accommodating the light collecting member by rolling the light collector when not needed becomes possible.

Figure 5A:
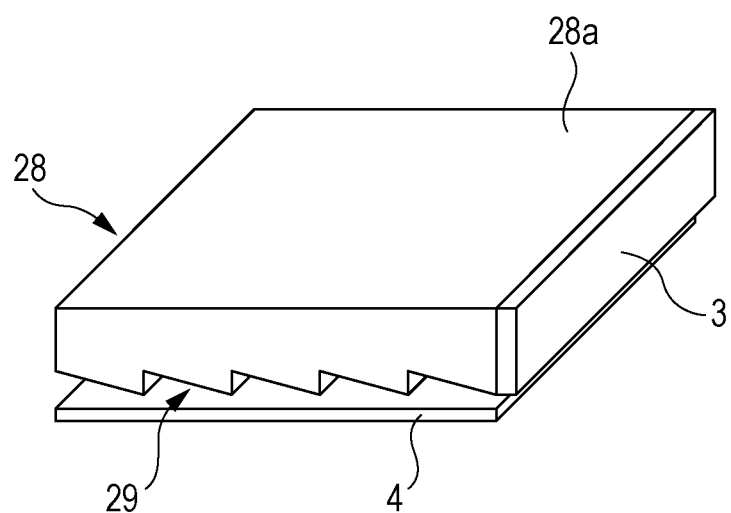
FIG. 5A is a perspective view illustrating a modification example of the solar cell module according to the present invention.
Figure 5B:
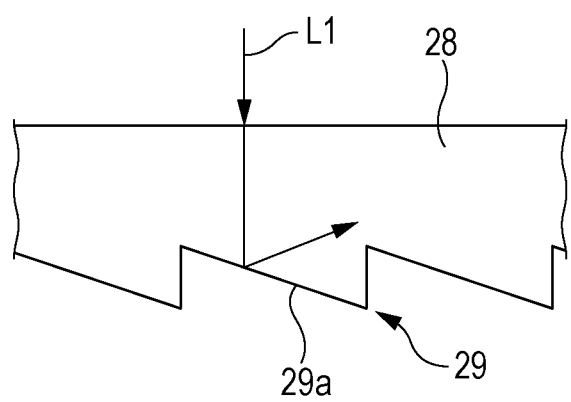
FIG. 5B is an enlarged view illustrating a main portion of the solar cell module in FIG. 5A.

In addition, a prism-like light collector 28 illustrated in FIG. 5A may be used as the light collector of the present embodiment. The light collector 28 includes a prism surface 29 facing a main surface 28a serving as a light incident surface. Multiple slope surfaces 29a inclined toward one end surface are formed on the prism surface 29 as illustrated in FIG. 5B. The light collector 28 has a configuration in which incident light L1 is refracted on the slope surface 29a to be emitted to the solar cell element 3 arranged on one end surface side as illustrated in FIG. 5A. In addition, light radiated from the phosphor 8, which propagates in the same manner as the light L1, is similarly emitted to the solar cell element 3.

Figure 5C:
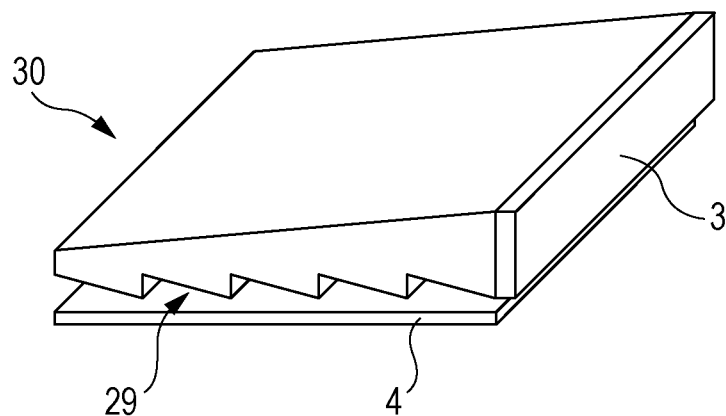
FIG. 5C is a perspective view illustrating a modification example of the solar cell module according to the present invention.

Further, as the light collector of the present embodiment, a wedge-like light collector 30 that includes a prism surface 29 and is formed such that the thickness thereof becomes gradually thinner as the light collector is separated from the solar cell element 3 as illustrated in FIG. 5C may be used. When the light collector 30 is formed in this manner, the number of total reflection of incident light L1 and radiation light from the phosphor 8 on the inside thereof is reduced and light loss generated by light being refracted on the slope surface 29a is reduced. Accordingly, extraction efficiency of light becomes increased.

Figure 5D:
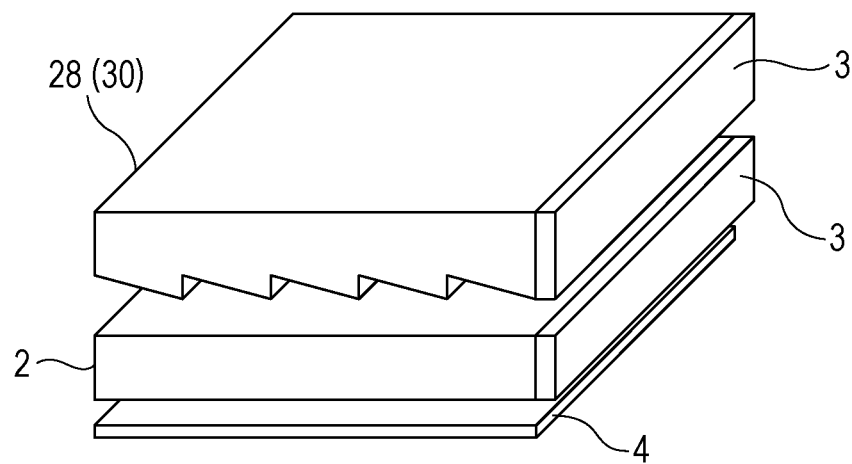
FIG. 5D is a perspective view illustrating a modification example of the solar cell module according to the present invention.

Further, as the light collector of the present embodiment, a light collector having a tandem structure, as illustrated in FIG. 5D, in which the light collector 2 is laminated on a light collector 28 (30) having a prism shape can be exemplified. In this case, the light collector 28 (30) having a prism shape may or may not contain the compounds (I) or (II).

<Solar Power Generation Device>

A solar power generation device according to the present embodiment includes the above-described solar cell module according to the present invention.

FIG. 6 is a view schematically illustrating a configuration of a solar power generation device according to the present embodiment.

A solar power generation device 1000 illustrated in the figure includes a solar cell module 1001, an inverter (DC-AC converter) 1004, and a storage battery 1005. The solar cell module 1001 converts the energy of solar light from the sun S into power. The inverter 1004 converts DC power output from the solar cell module 1001 into AC power. The storage battery 1005 stores the DC power output from the solar cell module 1001.

The solar cell module 1001 is the above-described solar cell module according to the present embodiment. The solar cell module 1001 includes a light collecting member (light collector) 1002 that collects solar light and a solar cell element 1003 that performs power generation using solar light collected by the light collecting member 1002.

The solar power generation device 1000 supplies power to an external electronic device 1006. Power is supplied to the electronic device 1006 from an auxiliary power source 1007 if necessary.

Since the solar power generation device 1000 having such a configuration includes the above-described solar cell module according to the present embodiment, the power generation amount thereof is excellent.

EXAMPLES

Hereinafter, aspects of the present invention will be described in detail with reference to specific examples. However, the aspects of the present invention are not limited to the examples described below.

Production of Compounds (I)

Example 1

Process of Producing Compound (Ib)

Compounds represented by the following formulae (1A)-101 and (1B)-101 (hereinafter, simply written as a "compound (1A)-101" and a "compound (1B)-101" respectively) are produced as compounds (I) by following the procedures described below. The compounds (1A)-101 and (1B)-101 are compounds (1) in which four benzene ring skeletons bonded to a carbon atom on the fourth position are dodecyl groups and others are all hydrogen atoms in $R^1$s, all $R^{11}$s represent a hydrogen atom, and $n_{11}$ is 1. In addition, the same compounds are used herein as the compounds (Ic) and (Id).

A compound (1,6,7,12-tetrachloroperylene-3,4,9,10-tetracarboxylic acid dianhydride, hereinafter, simply written as a "compound (1)-101e") represented by the following formula (1)-101e as a compound (Ie), a compound (2,3-diaminonaphthalene, hereinafter, simply written as a "compound (1)-101c") represented by the following formula (1)-101c as compounds (Ic) and (Id), and pyrazine are mixed with a mixed solvent of toluene and phenol.

The amounts of the compound (1)-101c and pyrazine to be used are respectively set to 4 molar times with respect to the compound (1)-101e. The total amount of toluene and phenol to be used is set to 40 mass times with respect to the compound (1)-101e.

The temperature of the mixed reaction liquid is increased, water which is secondarily produced is azeotropically dehydrated using toluene, and phenol is added thereto to be reacted at 145° C. for 24 hours.

Subsequently, the temperature of the reaction liquid is cooled to room temperature (25° C.), methanol is added thereto, crystals are deposited, and the deposited crystals are filtered to be washed with 10% by mass of a sodium hydroxide aqueous solution. Moreover, a mixture of compounds represented by the following formulae (1A)-101b and (1B)-101b (hereinafter, simply written as a "compound (1A)-101b" and a "compound (1B)-101b" respectively) is obtained as the compound (Ib) by slurry washing the obtained crystals with warm water, filtering the crystals to be washed with methanol, and then drying the resultant.

(Process of Producing Compounds (I))

A mixture having the total amount of the compounds (1A)-101b and (1B)-101b, a compound represented by the following formula (1)-101a (4-dodecylphenol, hereinafter, simply written as a "compound (1)-101a") as the compound (Ia), and potassium carbonate are mixed with N-methylpyrrolidone. The amounts of the compound (1)-101a and potassium carbonate to be used are respectively set to 6 molar times with respect to the total amount of the compounds (1A)-101b and (1B)-101b. The amount of N-methylpyrrolidone to be used is set to 20 mass times with respect to the compound (1)-101e.

The temperature of the mixed reaction liquid is increased to be reacted at 140° C. for 24 hours. Through this reaction, compounds (1A)-101 and (1B)-101 are obtained as the compounds (I).

Next, the temperature of the reaction liquid is cooled to room temperature (25° C.) to be added to 5% by volume of a hydrochloric acid aqueous solution, crystals are deposited, and the deposited crystals are filtered. The obtained crystals are slurry-washed with water and further slurry-washed with methanol, and filtered crystals are extracted, dissolved in methylene chloride, filtered, and then concentrated. Obtained concentrated residues are subjected to silica gel column chromatography using a mixed solvent of methylene chloride/n-hexane (6/4, volume ratio) as a moving phase, a fraction containing the compound (1A)-101 is separated, an operation of separating a target is performed, the obtained fraction is dissolved in methylene chloride, activated carbon is added thereto, and the resultant is stirred to be filtered. The contained solvent is concentrated while being substituted with n-hexane by concentrating the obtained filtrate, adding n-hexane thereto, and further performing a concentration operation. Further, a compound (1A)-101 is obtained by drying the obtained concentrated material under reduced pressure. Furthermore, a compound (1B)-101 is obtained by performing the same operation described above.

The compound (1A)-101 has a light absorption peak wavelength of 680 nm and is capable of absorbing light having a long wavelength.

Further, the peak wavelength of absorbable light is a value acquired by B3LYP/6-31G(d) using Gaussian09 (manufactured by Gaussian, Inc.). The same applies to the examples below.

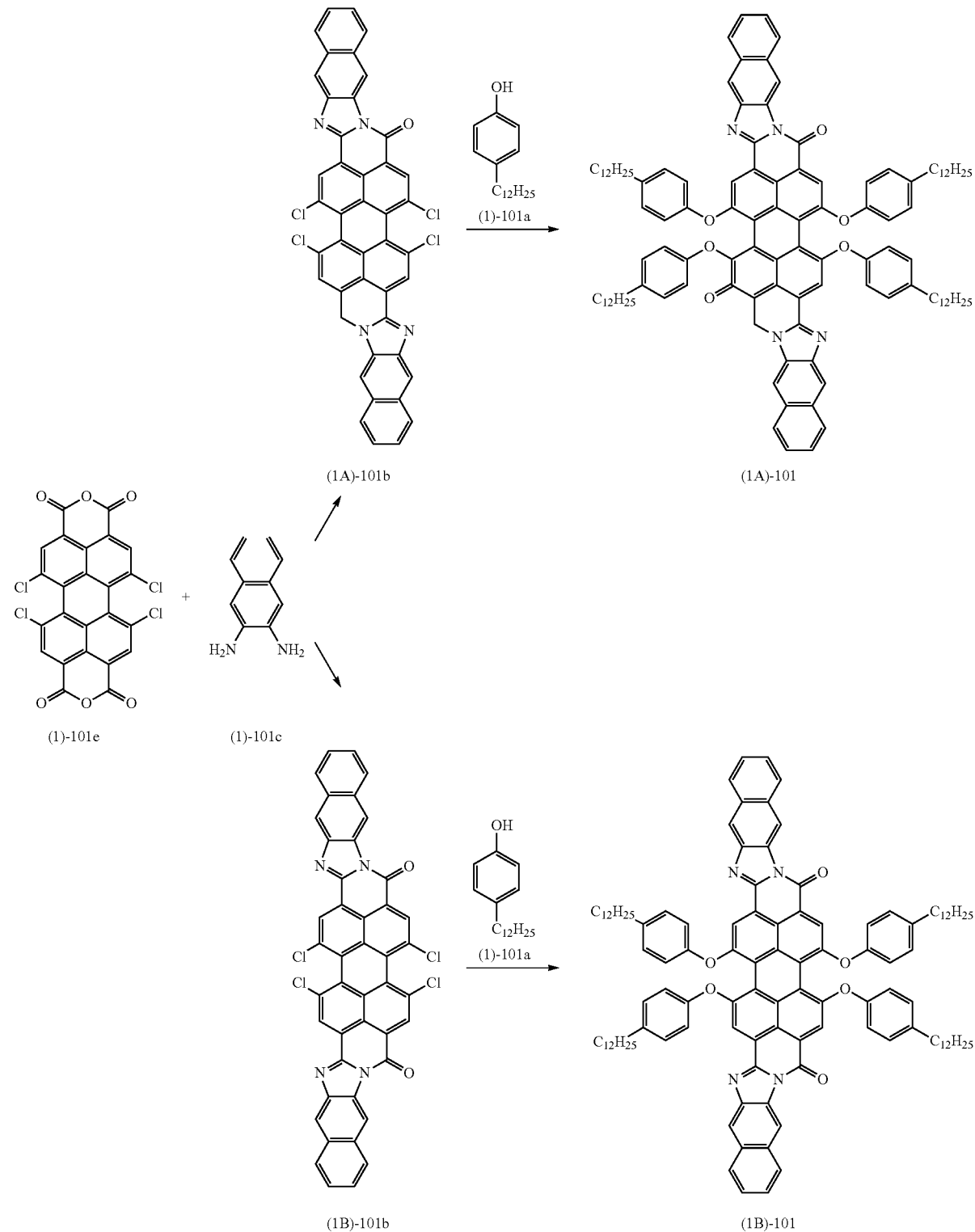
Example 2
Compounds represented by the following formulae (1A)-102 and (1B)-102 (hereinafter, simply written as a "compound (1A)-102" and a "compound (1B)-102" respectively) are produced as the compounds (I) in the same method as that described in Example 1 except that a compound represented by the following formula (1)-102c is used instead of the compound (1)-101c as compounds (Ic) and (Id).

The compound (Ib) is produced through compounds represented by the following formulae (1A)-102b and (1B)-102b. The compounds (1A)-102 and (1B)-102 are compounds (1) in which four benzene ring skeletons bonded to a carbon atom on the fourth position are dodecyl groups and others are all hydrogen atoms in $R^1$s, all $R^{11}$s represent a hydrogen atom, and $n_{11}$ is 2.

The compound (1A)-102 can absorb light having a peak wavelength of 770 nm.

[Chem. 34]

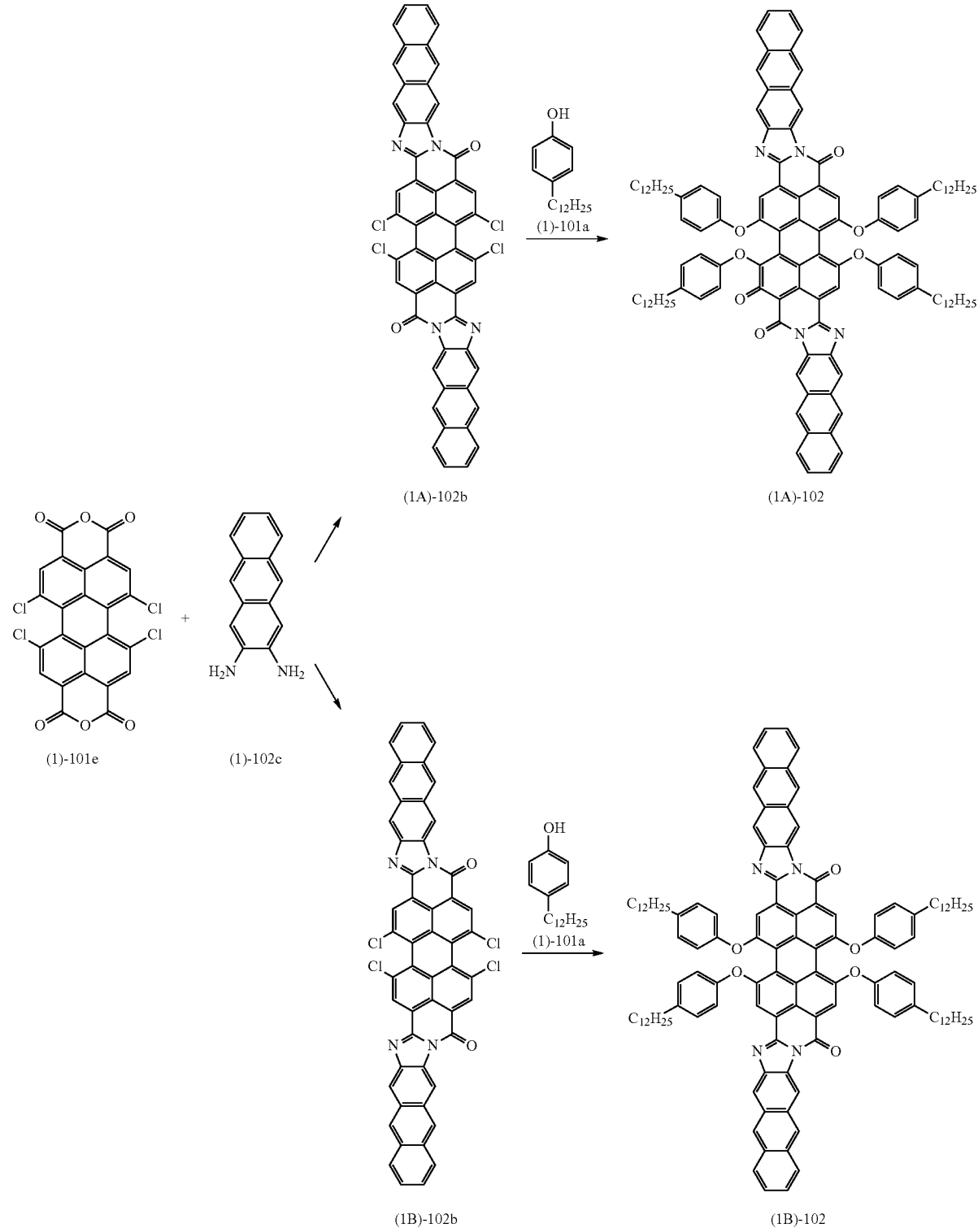

Example 3

Compounds represented by the following formulae (1A)-201, (1B)-201, and (1A)-301 (hereinafter, simply written as a "compound (1A)-201," a "compound (1B)-201," and a "compound (1A)-301" respectively) are produced as the compounds (I) in the same method as that described in Example 1 except that a compound represented by the following formula (1)-201c is used instead of the compound (1)-101c as compounds (Ic) and (Id). The compound (Ib) is produced through compounds represented by the following formulae (1A)-201b, (1B)-201b, and (1A)-301b. The compounds (1A)-201 and (1B)-201 are compounds (1) in which four benzene ring skeletons bonded to a carbon atom on the fourth position are dodecyl groups and others are all hydrogen atoms in $R^1$s, all $R^{12}$s represent a hydrogen atom, and $n_{12}$ is 1. The compound (1A)-301 is a compound (1) in which four benzene ring skeletons bonded to a carbon atom on the fourth position are dodecyl groups and others are all hydrogen atoms in $R^1$s, all $R^{13}$s represent a hydrogen atom, and $n_{13}$ is 1.

The compound (1A)-201 can absorb light having a peak wavelength of 695 nm.

The compound (1A)-301 can absorb light having a peak wavelength of 675 nm.

[Chem. 35]

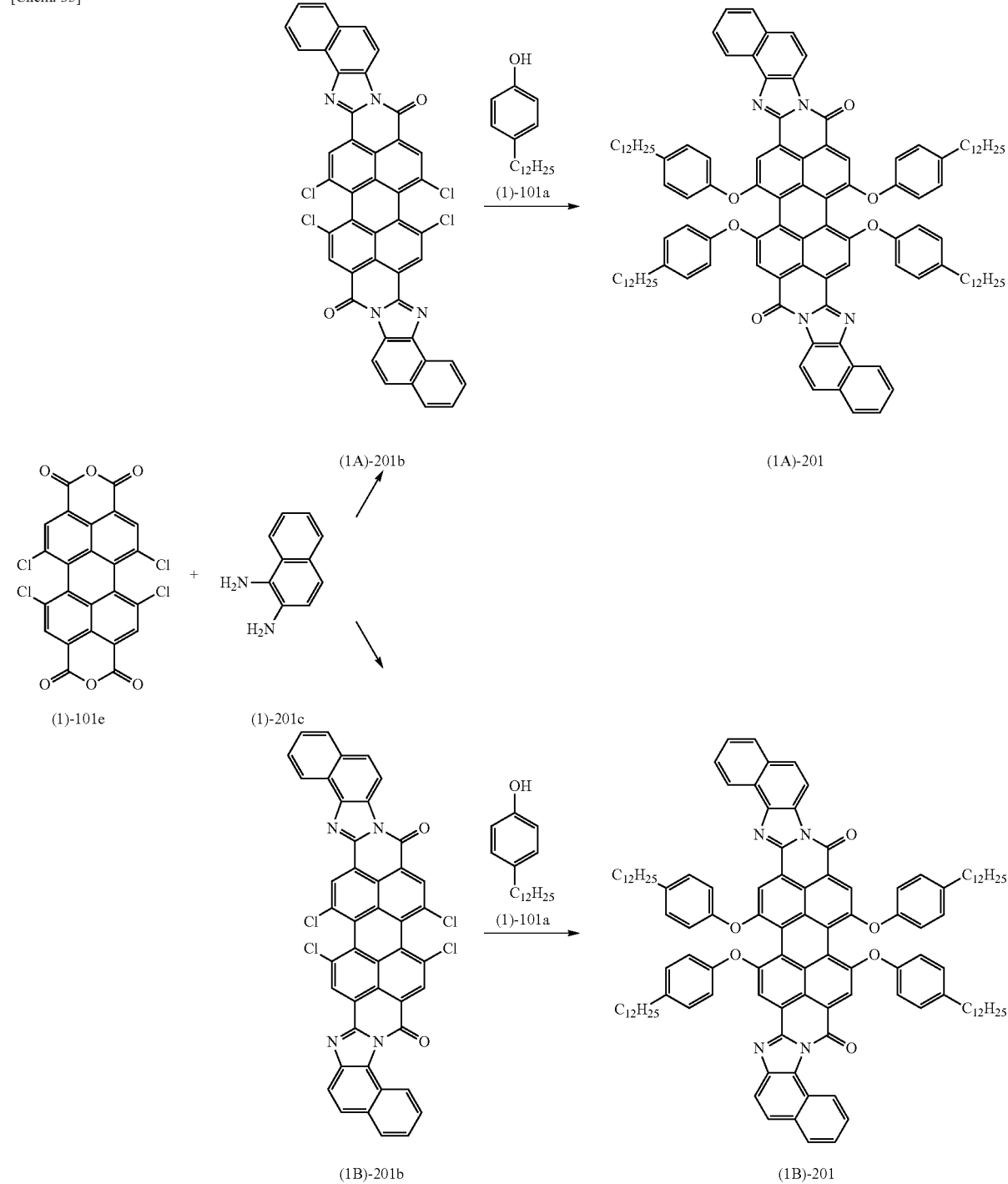

[Chem. 36]

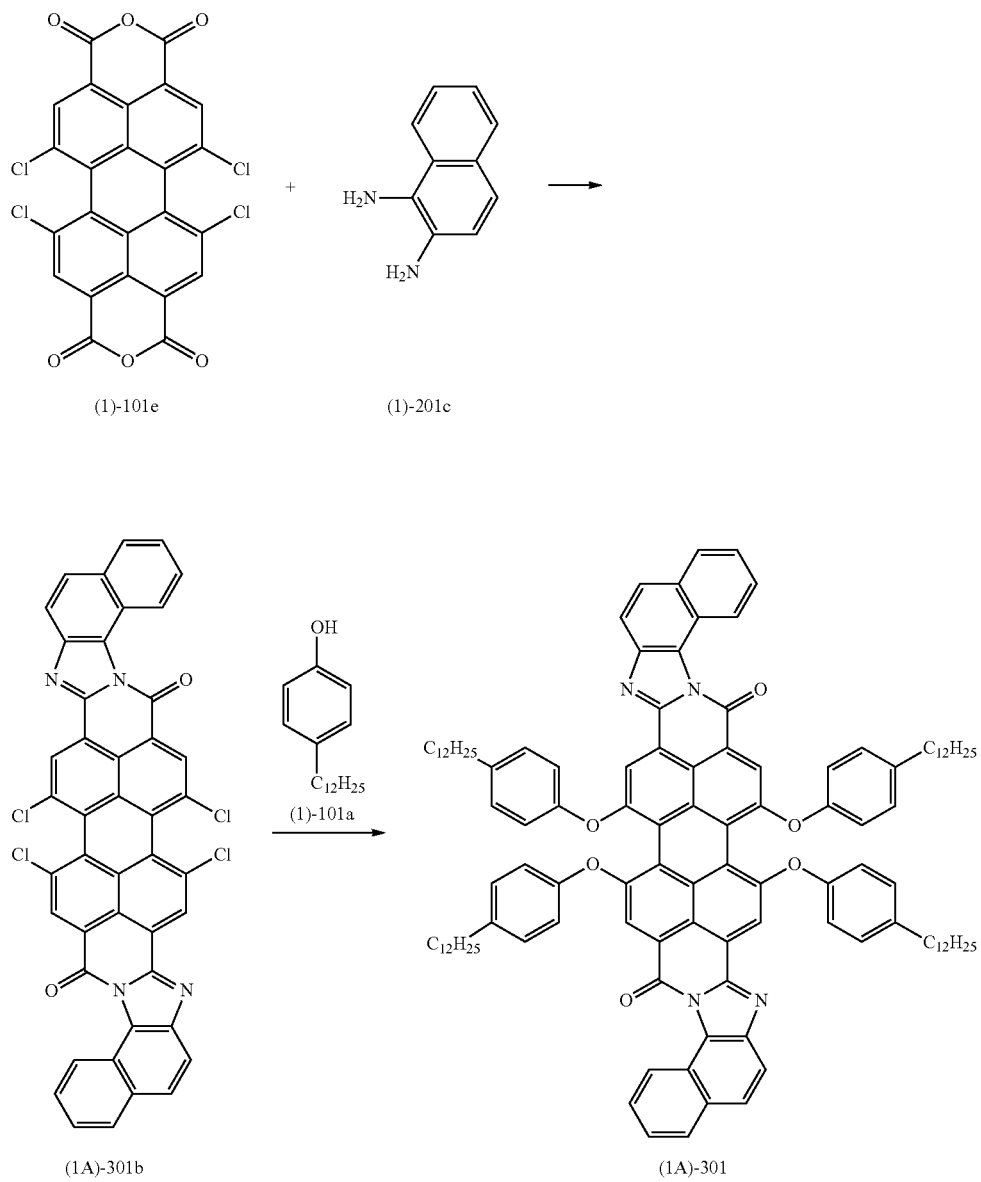

Example 4

Compounds represented by the following formulae (1A)-202, (1B)-202, and (1A)-302 (hereinafter, simply written as a "compound (1A)-202," a "compound (1B)-202," and a "compound (1A)-302" respectively) are produced as the compounds (I) in the same method as that described in Example 1 except that a compound represented by the following formula (1)-202c is used instead of the compound (1)-101c as compounds (Ic) and (Id). The compound (Ib) is produced through compounds represented by the following formulae (1A)-202b, (1B)-202b, and (1A)-302b. The compounds (1A)-202 and (1B)-202 are compounds (1) in which four benzene ring skeletons bonded to a carbon atom on the fourth position are dodecyl groups and others are all hydrogen atoms in $R^1$s, all $R^{12}$s represent a hydrogen atom, and $n_{12}$ is 2. The compound (1A)-302 is a compound (1) in which four benzene ring skeletons bonded to a carbon atom on the fourth position are dodecyl groups and others are all hydrogen atoms in $R^1$s, all $R^{13}$s represent a hydrogen atom, and $n_{13}$ is 2.

The compound (1A)-202 can absorb light having a peak wavelength of 780 nm.

The compound (1A)-302 can absorb light having a peak wavelength of 772 nm.

[Chem. 37]
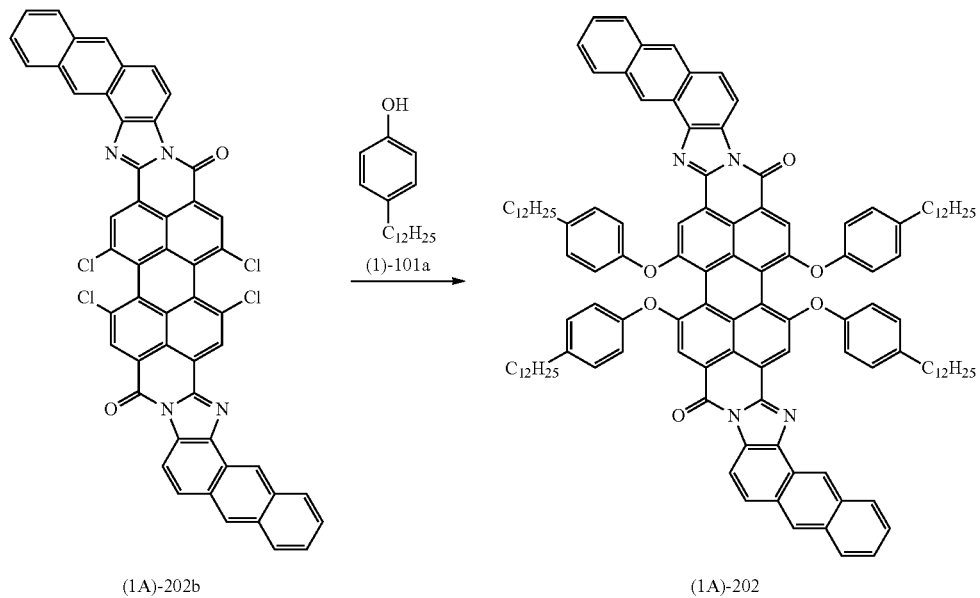
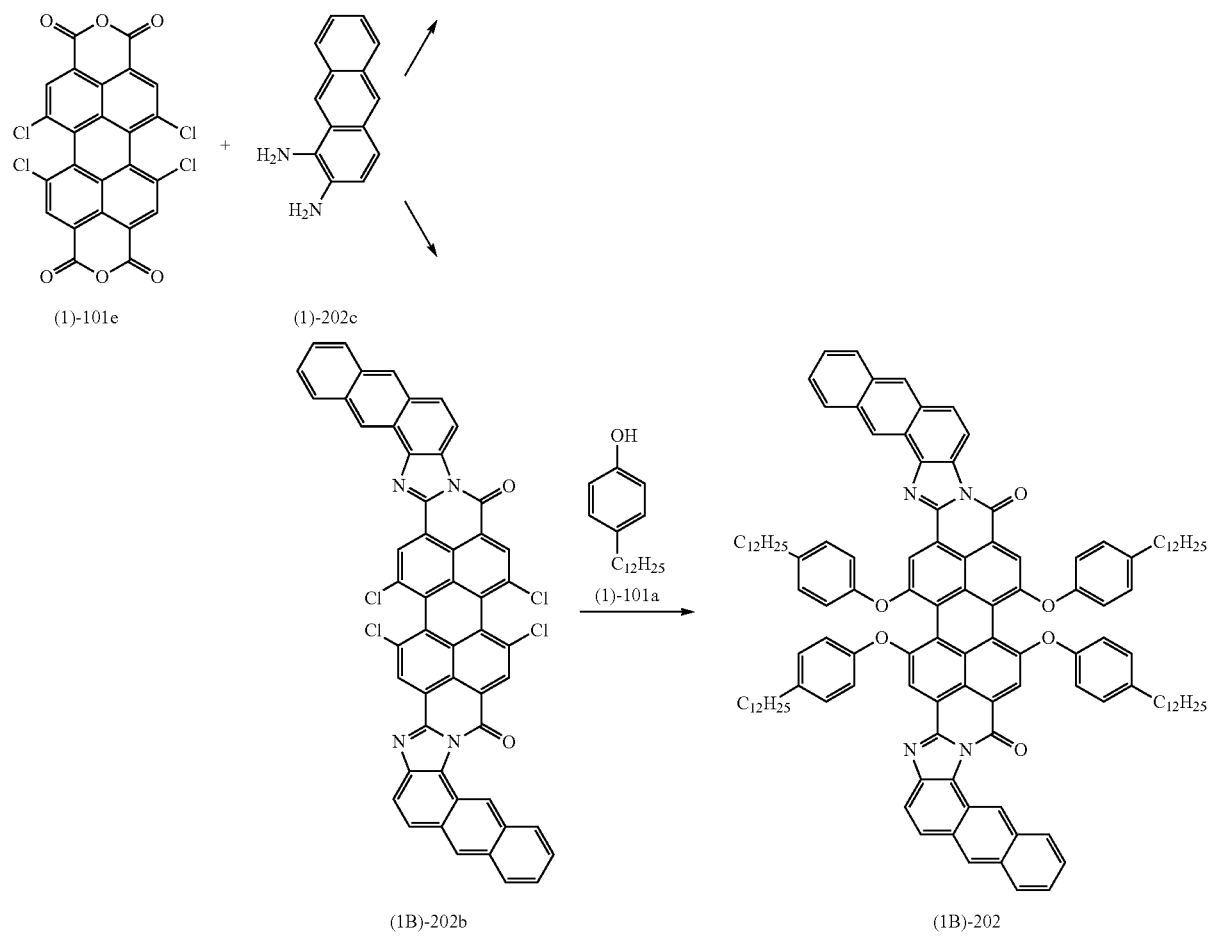

[Chem. 38]

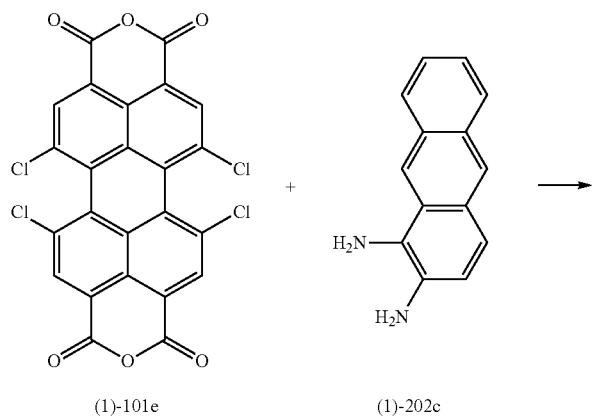

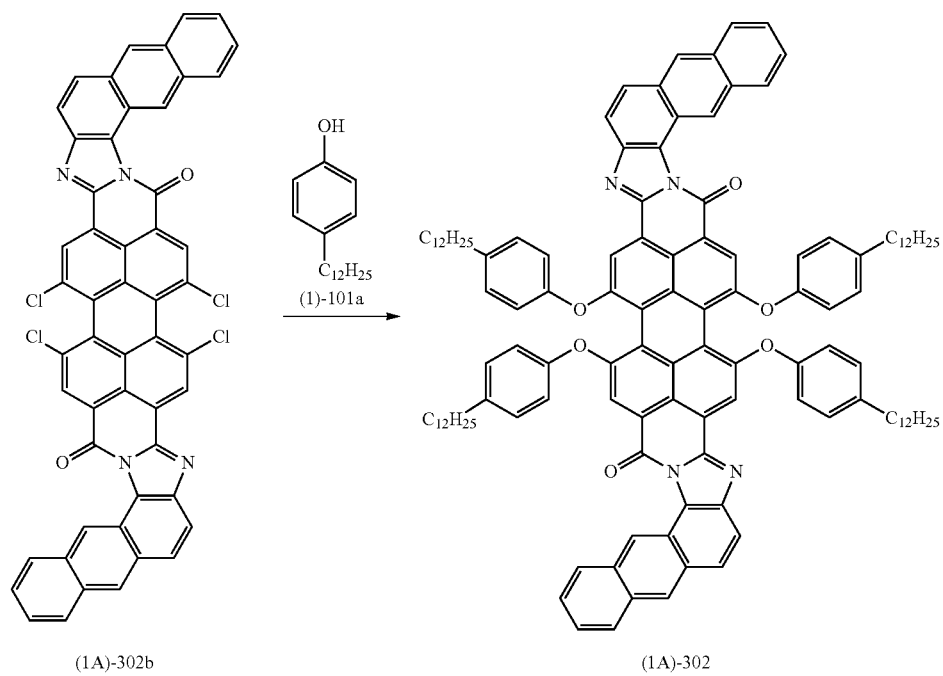

Example 5

Compounds represented by the following formulae (1A)-103 and (1B)-103 (hereinafter, simply written as a "compound (1A)-103" and a "compound (1B)-103" respectively) are produced as the compounds (I) in the same method as that described in Example 1 except that a compound represented by the following formula (1)-102c is used in addition to the compound (1)-101c as compounds (Ic) and (Id). The compound (Ib) is produced through compounds represented by the following formulae (1A)-103b and (1B)-103b. The compounds (1A)-103 and (1B)-103 are compounds (1) in which four benzene ring skeletons bonded to a carbon atom on the fourth position are dodecyl groups and others are all hydrogen atoms in $R^1$s, all $R^{11}$s represent a hydrogen atom and $n_{11}$ is 1 in $Ar^1$, and all $R^{11}$s represent a hydrogen atom and $n_u$ is 2 in $Ar^2$.

The compound (1A)-103 can absorb light having a peak wavelength of 752 nm.

[Chem. 39]
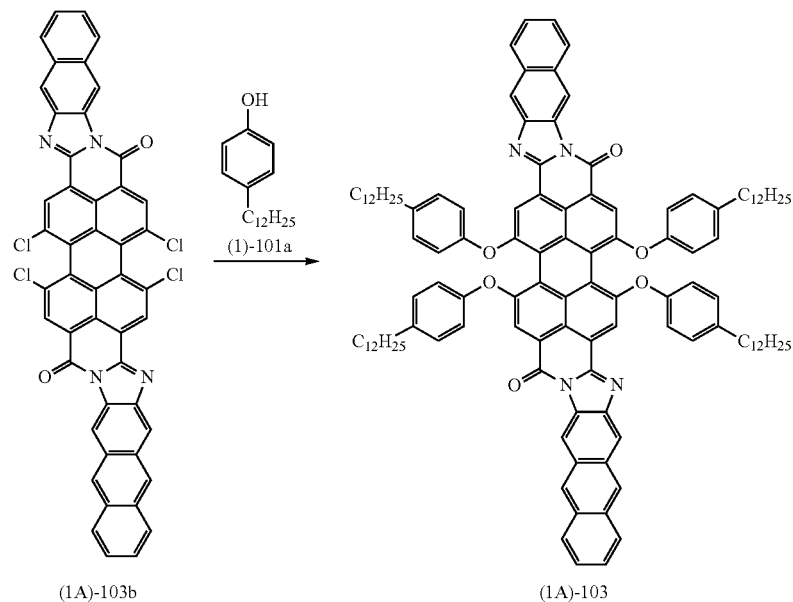
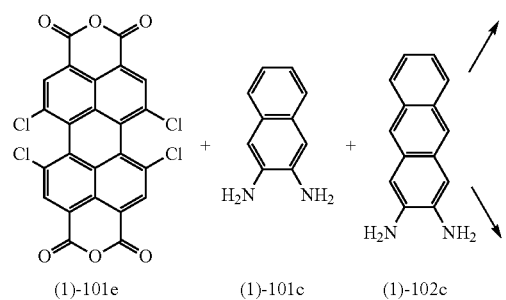
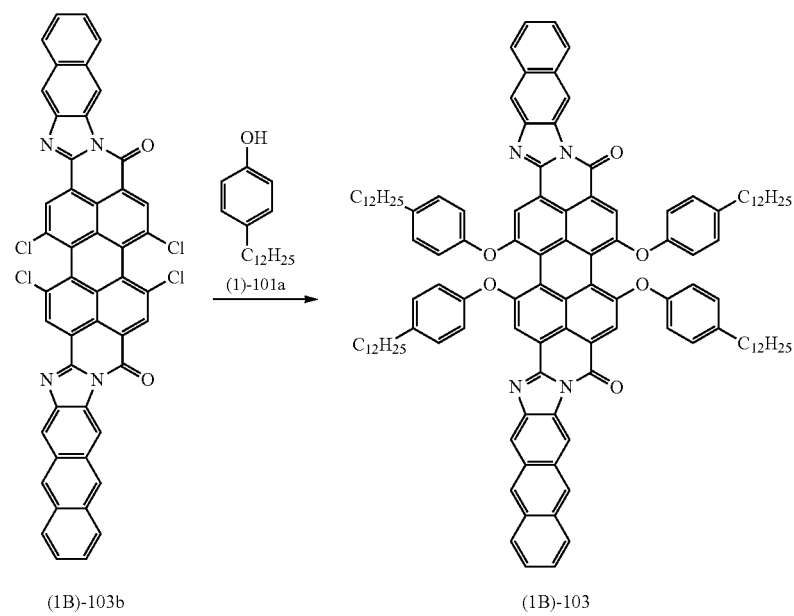

Example 6

Compounds represented by the following formulae (2A)-101, (2B)-101, and (2A)-201 (hereinafter, simply written as a "compound (2A)-101," a "compound (2B)-101," and a "compound (2A)-201" respectively) are produced as the compounds (I) in the same method as that described in Example 1 except that a compound represented by the following formula (2)-101c is used instead of the compound (1)-101c as compounds (Ic) and (Id). The compound (Ib) is produced through compounds represented by the following formulae (2A)-101b, (2B)-101b, and (2A)-201b. The compounds (2A)-101 and (2B)-101 are compounds (2) in which four benzene ring skeletons bonded to a carbon atom on the fourth position are dodecyl groups and others are all hydrogen atoms in $R^1$s, and all $R^{21}$s represent a hydrogen atom. The compound (2A)-201 is a compound (2) in which four benzene ring skeletons bonded to a carbon atom on the fourth position are dodecyl groups and others are all hydrogen atoms in $R^1$s, and all $R^{22}$s represent a hydrogen atom.

The compound (2A)-101 can absorb light having a peak wavelength of 768 nm.

The compound (2B)-101 can absorb light having a peak wavelength of 660 nm.

[Chem. 40]

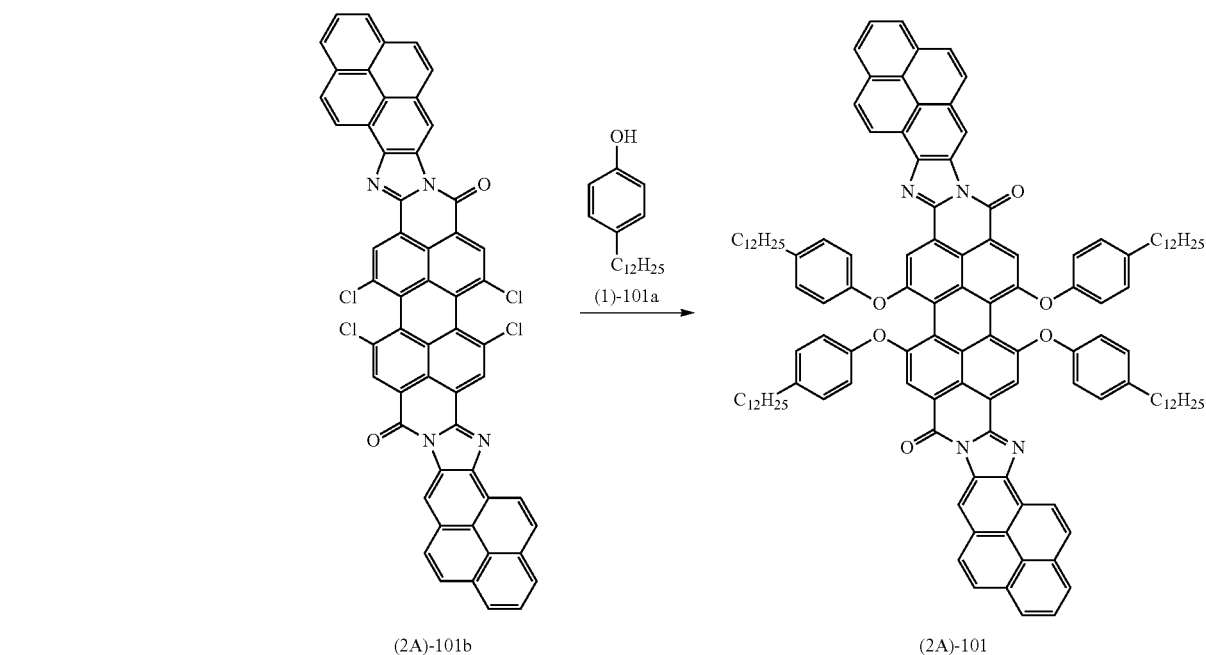

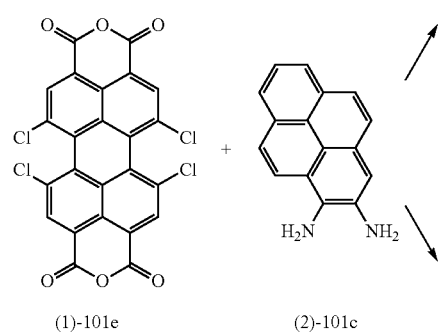

-continued
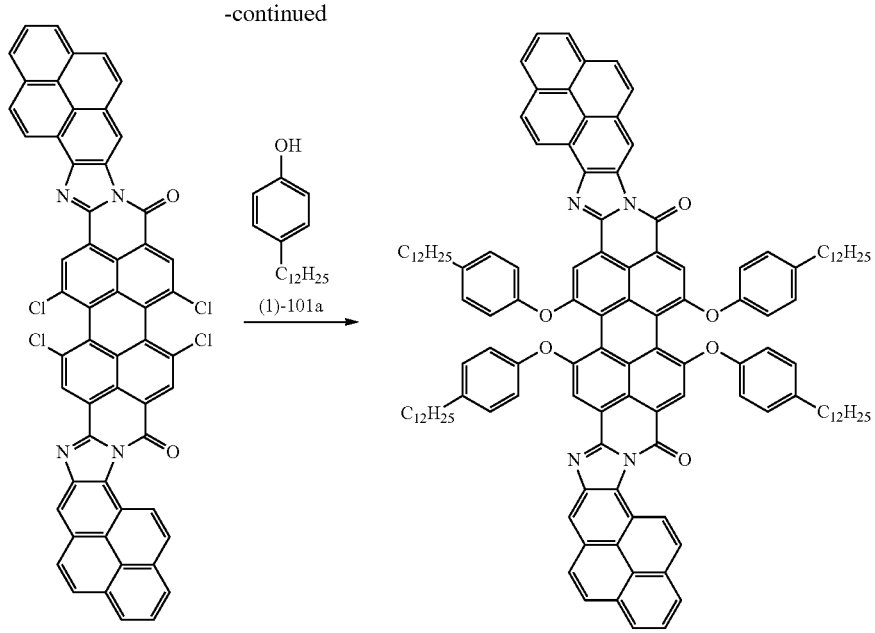
(2B)-101b → (2B)-101
[Chem. 41]
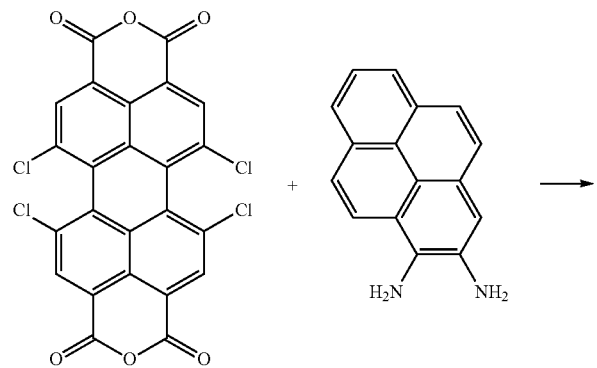
(1)-101e + (2)-101c →
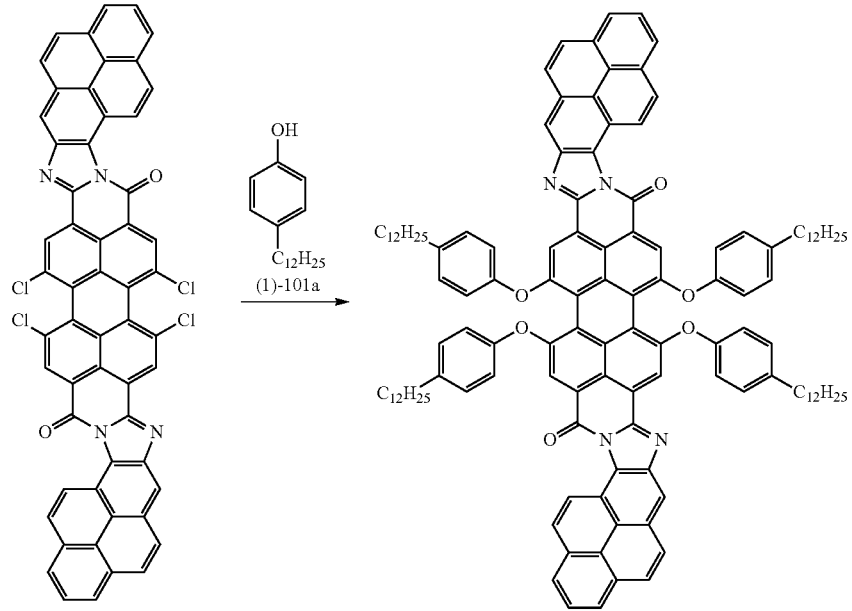
(2A)-201b → (2A)-201

Example 7

Compounds (1A)-101 and (1B)-101 were synthesized as the compounds (I) by following the procedures described below.

(Reaction Process 1)

First, a reaction represented by the reaction formula (1-11) was performed as a reaction process 1.

500 g of chlorosulfuric acid (4.29 mol) was added to 1000 mL of a three-necked flask through argon gas, and 50 g (0.127 mol) of 3,4,9,10-perylenetetracarboxylic acid dianhydride was added thereto at room temperature for 20 minutes. Next, 8.5 g (0.024 mol) of iodine was added thereto. The temperature of the obtained reaction liquid was increased to 70° C., and the reaction liquid was reacted by stirring for 6 hours. After the reaction was terminated, the temperature of the reaction liquid was cooled to the room temperature, 2000 mL of ice water was added thereto, and then the reaction liquid was quenched. The color of the reaction liquid was changed from dark brown into vermilion and crystals were deposited. The crystals were collected by filtration to be slurry-washed using 1000 mL of water for three times. Subsequently, slurry washing was further performed using 500 mL of acetonitrile for three times. The collected crystals by filtration were dried. The wet weight of an obtained product was 102 g, the dry weight thereof was 50.1 g, and the yield thereof was 74.4%.

Figure 8:
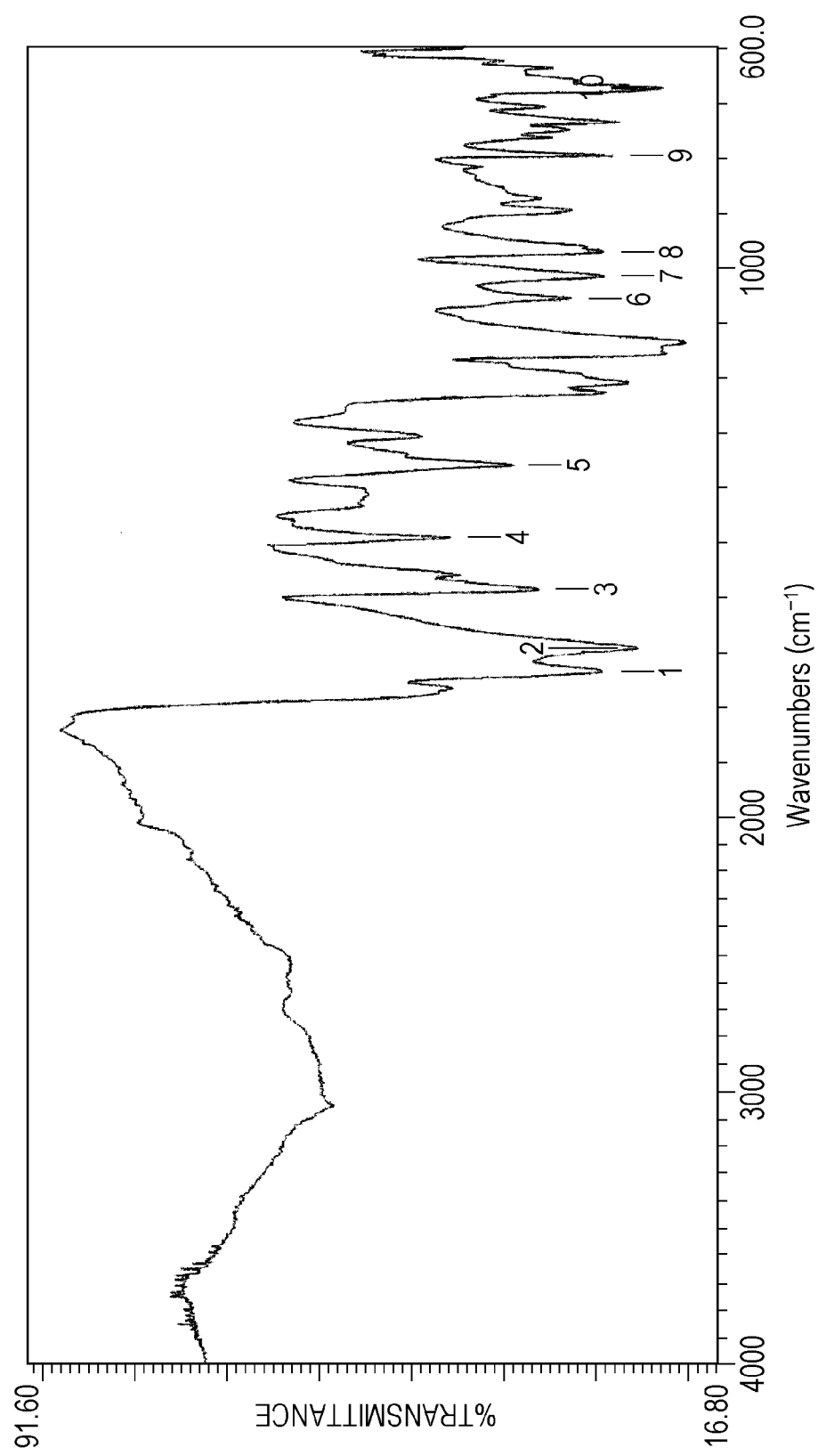
FIG. 8 is a diagram illustrating an IR spectrum of the product of the reaction formula (1-11) of Example 7.

Results of mass analysis of the obtained crystals are shown in FIG. 7 and the IR spectrum is shown in FIG. 8. It was confirmed that a molecular ion peak m/z was 530 using an MS spectrum in FIG. 7. Further, it was also confirmed that m/z was 564, which was considered as a pentachloro body.

The chlorine content of the obtained crystals was measured using an oxygen combustion method and ion chromatography. The Cl$^-$ content was 25.1% (theoretical value: 26.8%).

[Chem. 42]

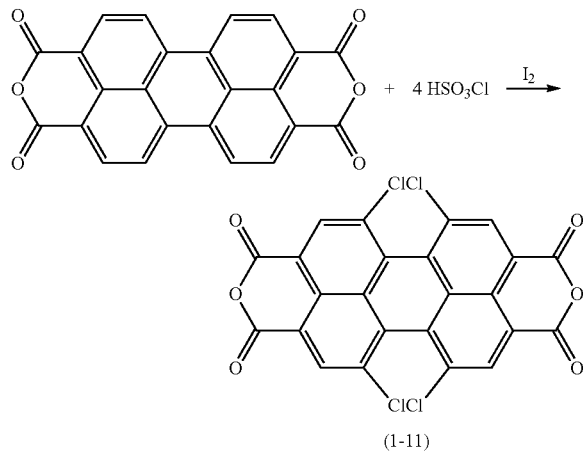

(1-11)

(Reaction Process 2)

A reaction represented by the reaction formula (1-12) was performed as a reaction process 2 using the compound obtained by the reaction process 1.

20 g (37.7 mmol) of 1,6,7,12-tetrachloroperylene-3,4,9,10-tetracarboxylic acid dianhydride, 13.1 g (150.8 mmol) of n-pentylamine, and 225 g of propionic acid were added to 300 mL of a three-necked flask. The temperature of the mixed solution was increased to 140° C. and the mixed solution was reacted by stirring for 24 hours. After the reaction was terminated, the temperature of the reaction liquid was cooled to room temperature, and crystals were deposited. The crystals were collected by filtration to be slurry-washed using 400 mL of a 10% sodium hydrogen carbonate aqueous solution. Next, the crystals were slurry-washed using 200 mL of water, collected by filtration, and then washed over using methanol. The collected crystals by filtration were dried. The wet weight of an obtained product was 25.1 g, the dry weight thereof was 21.7 g, and the yield thereof was 86.1%.

[Chem. 43]

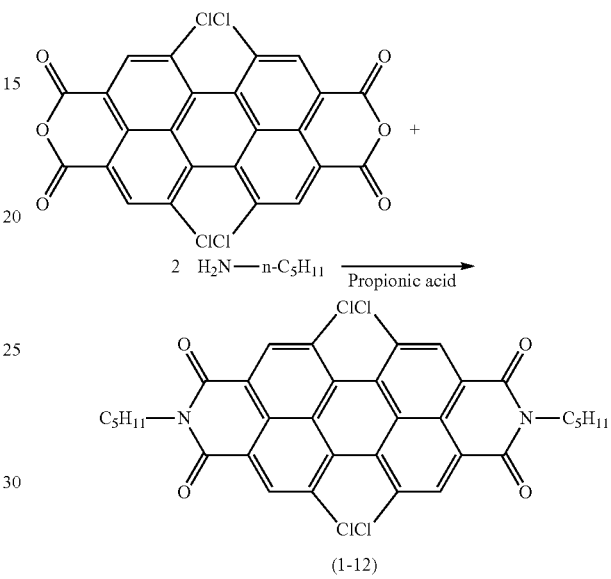

(1-12)

Figure 9:
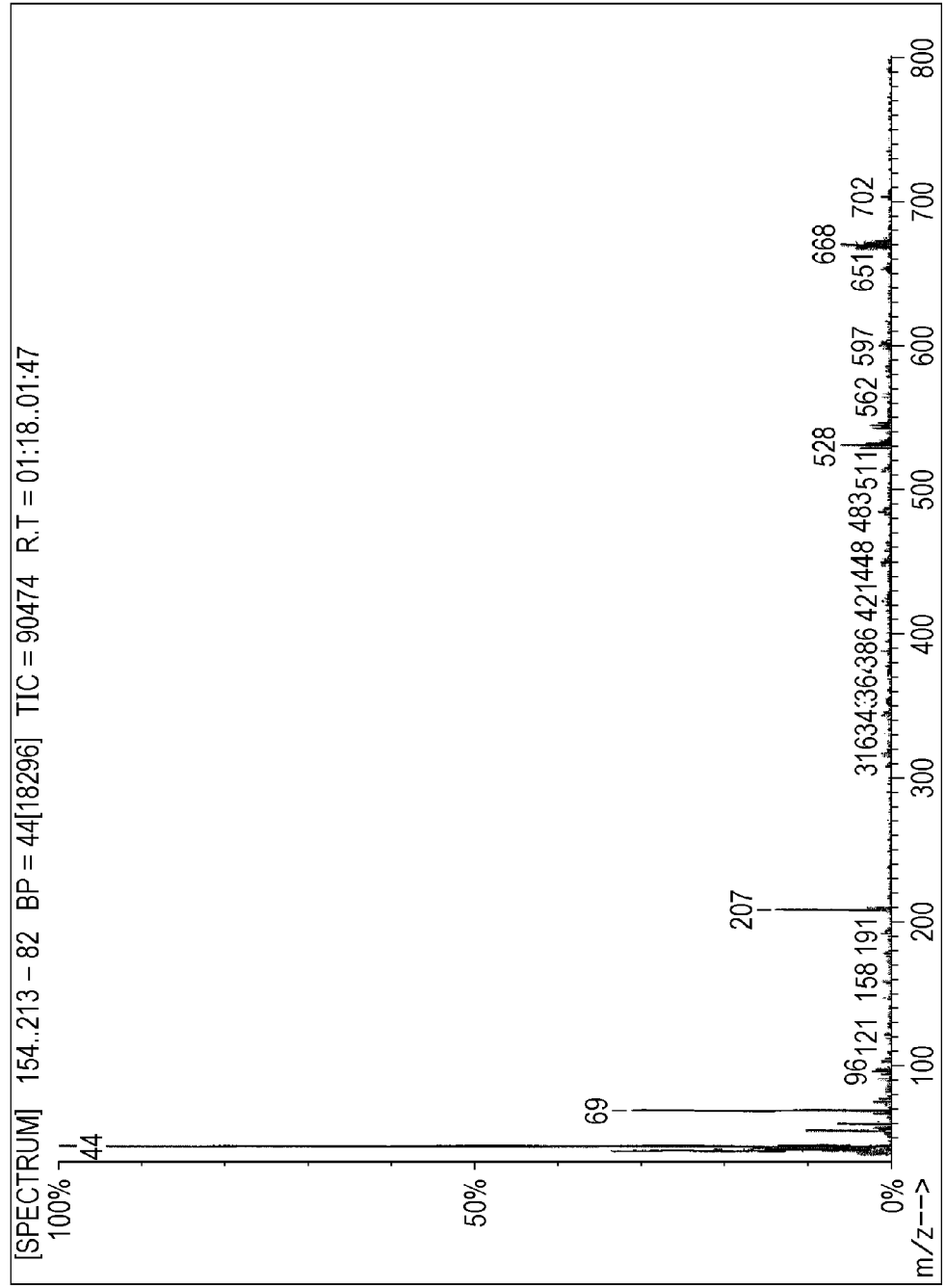
FIG. 9 is a diagram illustrating results of mass analysis of the product of a reaction formula (1-12) of Example 7.
Figure 10:
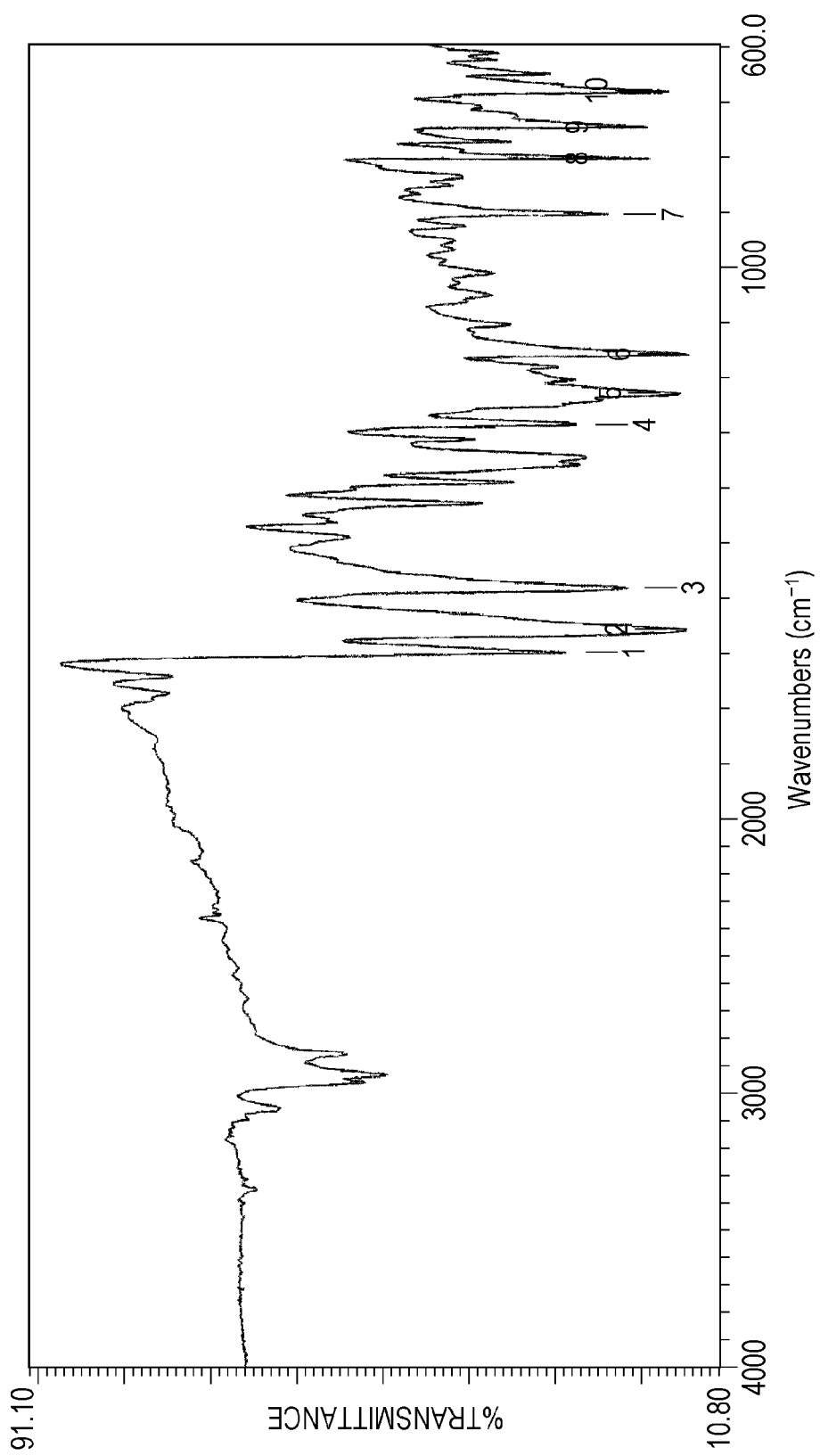
FIG. 10 is a diagram illustrating an IR spectrum of the product of the reaction formula (1-12) of Example 7.
Figure 11:
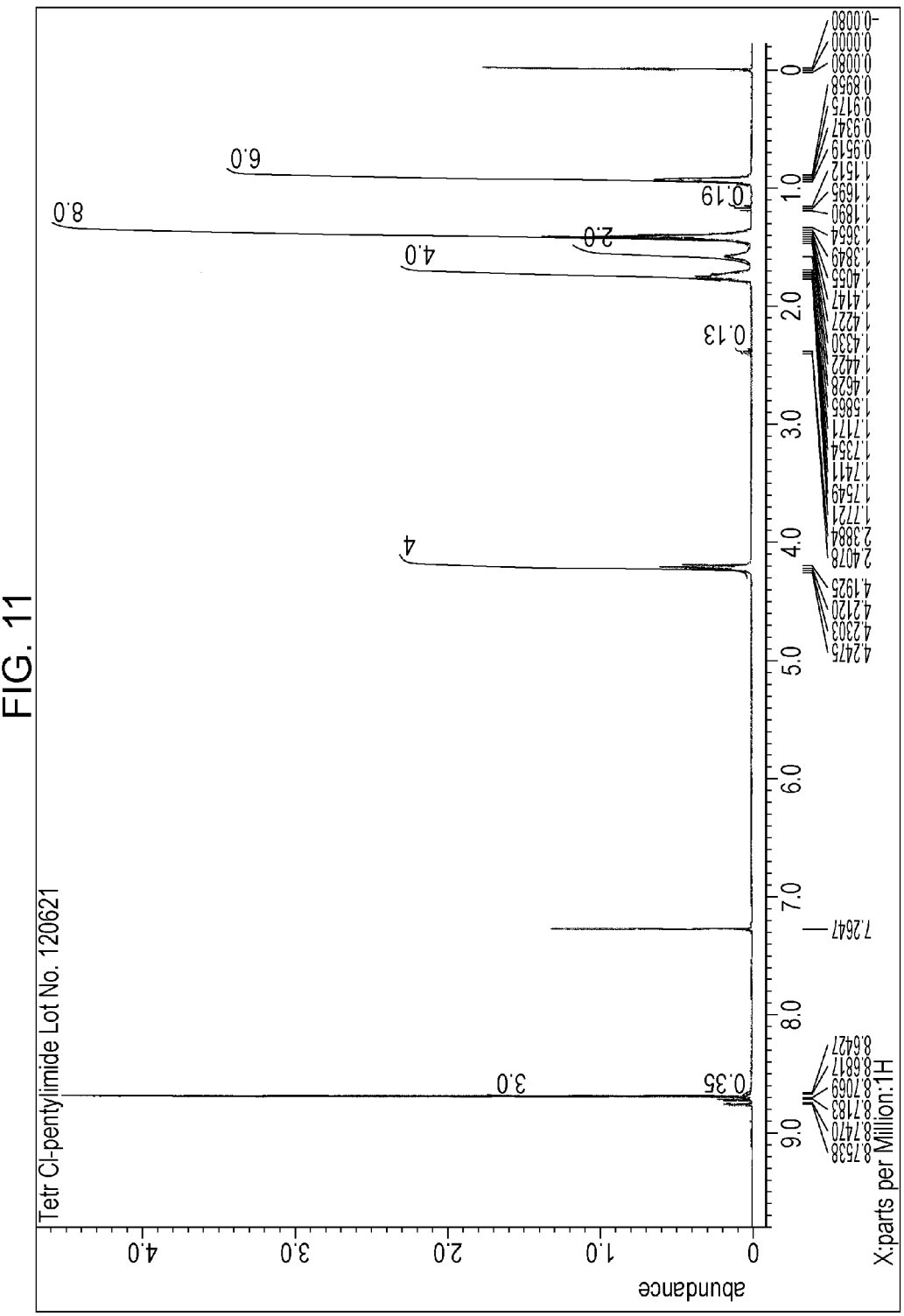
FIG. 11 is a diagram illustrating results of $^1$H-NMR of the product of the reaction formula (1-12) of Example 7.

Results of mass analysis of the obtained crystals are shown in FIG. 9 and a result of the IR spectrum is shown in FIG. 10, and results of 1H-NMR are shown in FIG. 11. It was confirmed that a parent ion peak m/z was 668 using an MS spectrum in FIG. 9. Further, an n-pentyl group was confirmed using an NMR method (nuclear magnetic resonance spectroscopy).

(Reaction Process 3)

A reaction represented by the reaction formula (1-13) was performed as a reaction process 3 using the compound obtained by the reaction process 2.

20 g (0.03 mmol) of 3,4,9,10-bis(n-pentylimide)-1,6,7,12-tetrachloroperylene, 47.2 g (0.18 mol) of dodecylphenol, 24.8 g (0.18 mol) of potassium carbonate, and 600 mL of N-methylpyrrolidone were added to 1000 mL of a three-necked flask. The temperature of the mixed solution was increased to 140° C. and the mixed solution was reacted by stirring for 24 hours. After the reaction was terminated, the temperature of the mixed solution was cooled to room temperature, and the reaction liquid was extracted to 600 mL of 2N HCl to obtain a tar-like solid. The tar was filtered to be slurry-washed using 1000 mL of water, and further slurry-washed using 1000 mL of methanol two times, and then filtered. The wet weight of an obtained tar was 65 g. The tar was dissolved in 300 mL of methylene chloride and then filtered (clogging occurs at the time of column chromatography without filtration). The mother liquor was concentrated to a liquid amount of approximately 200 mL, and a solution obtained by mixing a 1:1 ratio of methylene chloride and n-hexane was used for an eluent, and then a target was fractionated at the time of silica gel chromatography (250 g of silica gel). The weight of the main fraction was 23.0 g (tar-like).

[Chem. 44]

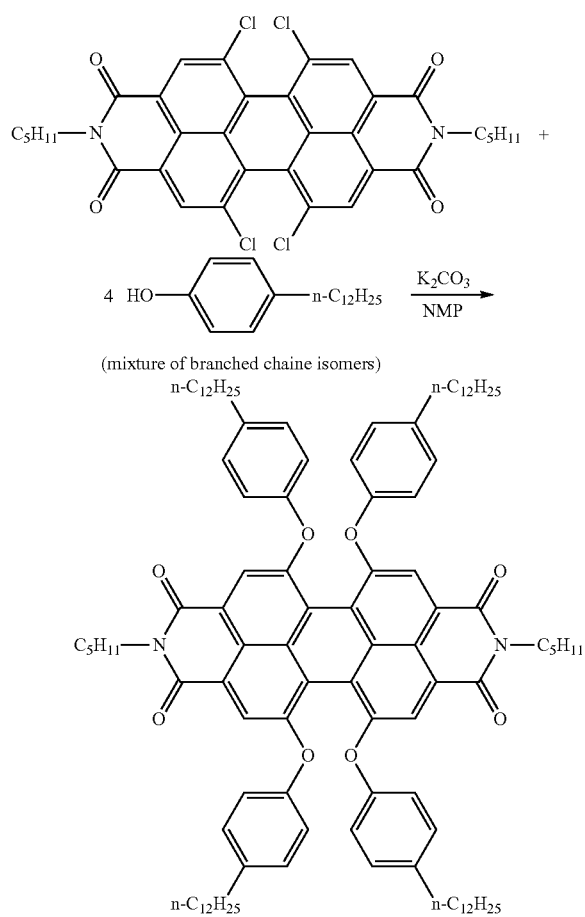

(1-13)

(mixture of branched chaine isomers)

Figure 12:
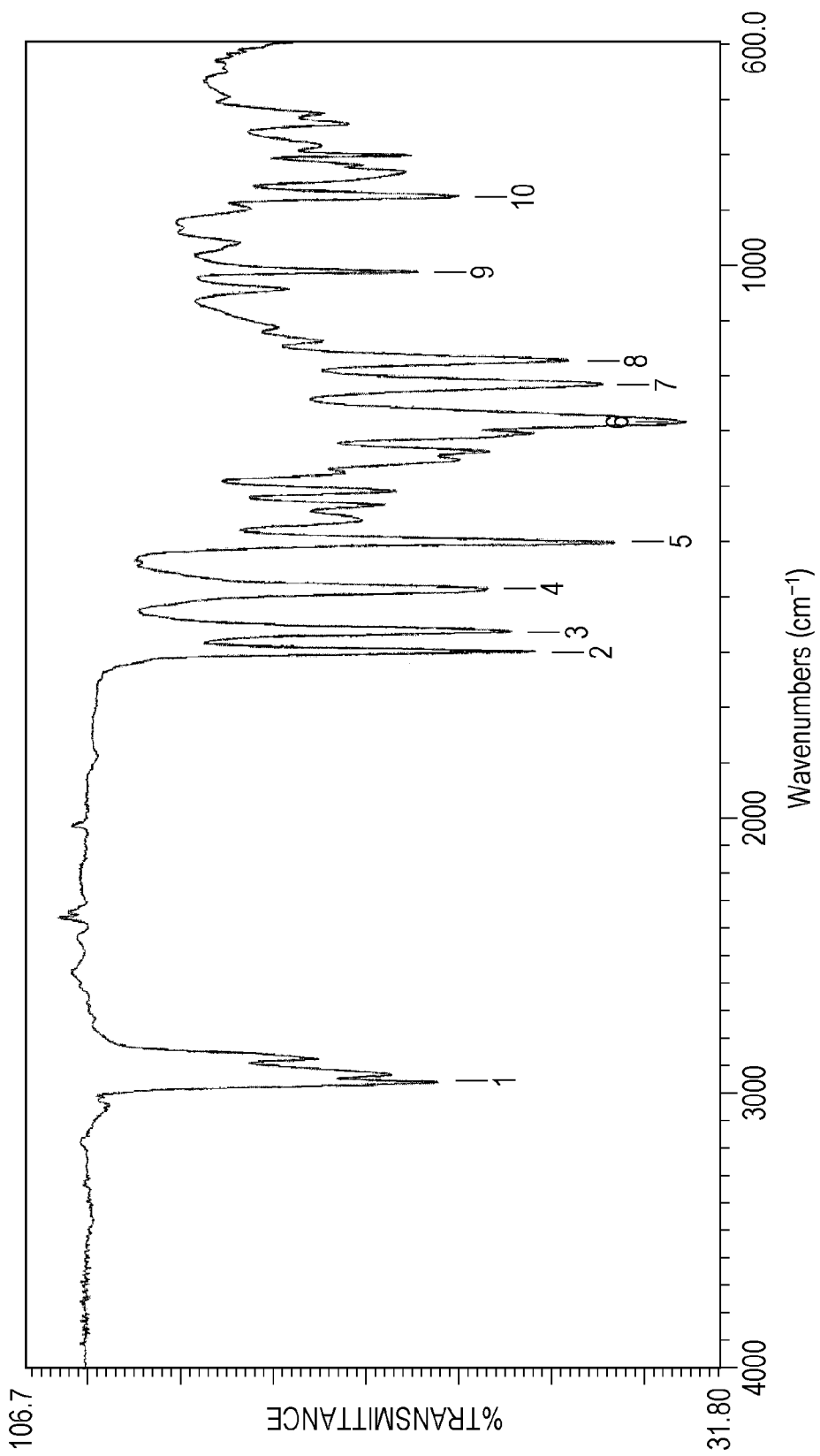
FIG. 12 is a diagram illustrating an IR spectrum of a product of a reaction formula (1-13) of Example 7.
Figure 13:
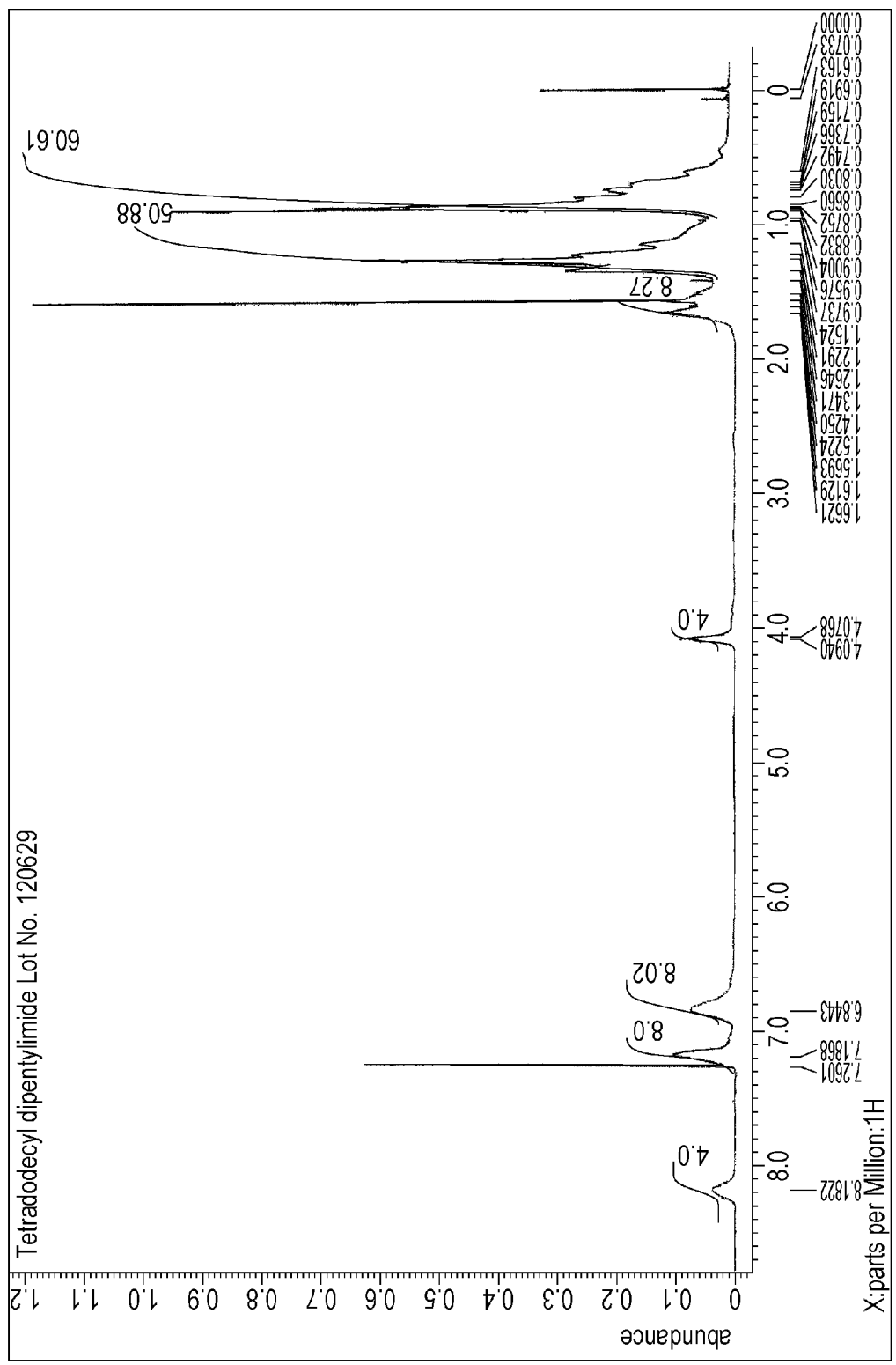
FIG. 13 is a diagram illustrating results of $^1$H-NMR of the product of the reaction formula (1-13) of Example 7.

Results of the IR spectrum of the obtained main fraction are shown in FIG. 12 and results of $^1$H-NMR are shown in FIG. 13. From the results obtained from the NMR method shown in FIG. 13, the number of Hs (hydrogen) of an alkyl group was compared to the total amount of the number of Hs of a benzene ring. As a result, H of the alkyl group: H of the benzene ring was 20.02H:123.76H (theoretical value 20H: 122H).

(Reaction Process 4)

A reaction represented by the reaction formula (1-14) was performed as a reaction process 4 using the compound obtained by the reaction process 3.

22 g (14 mmol) of N,N'-bis(n-pentyl)-1,6,7,12-tetrakis(4-dodecylphenoxy)perylene-3,4,9-10-tetracarboxylic acid imide, 98 g (1490 mmol) of 85% potassium hydroxide, and 220 mL of 2-propanol were added to 300 mL of a three-necked flask. The mixed solution was refluxed and then reacted by stirring for 72 hours. The color of the reaction liquid was changed from purplish red into green. After the stirring reaction was terminated, the temperature of the reaction liquid was cooled to room temperature, and pH of the reaction liquid was adjusted to be pH 4 in 8% HCl. A deposited tar-like solid was collected by filtration. The obtained tar was slurry-washed using 2 times 500 mL of water. Next, the washed tar was dispersed into 500 mL of methanol and a solid to which tar was dispersed was collected by filtration. Further, the tar was slurry-washed in 500 mL of methanol and a solid was collected by filtration. The collected solid by filtration was dried at room temperature. The wet weight of an obtained product was 18 g, the dry weight thereof was 14 g, and the yield thereof was 70%.

[Chem. 45]

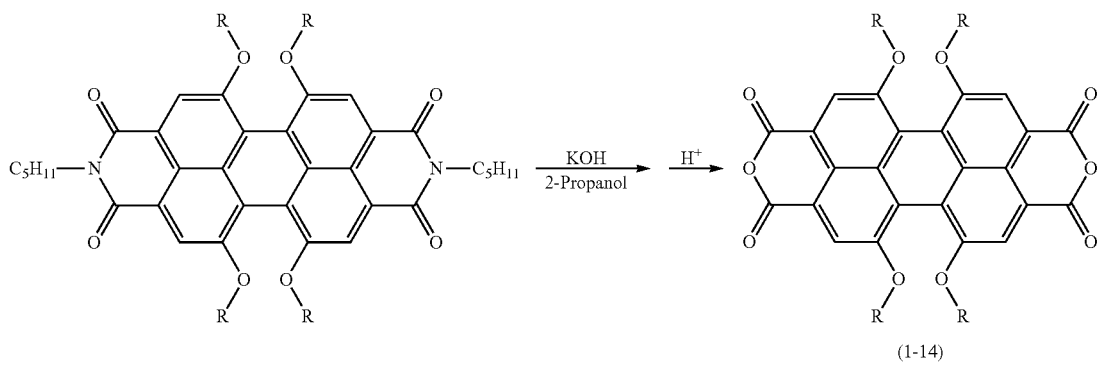

(1-14)

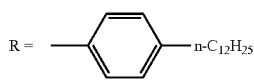

Figure 14:
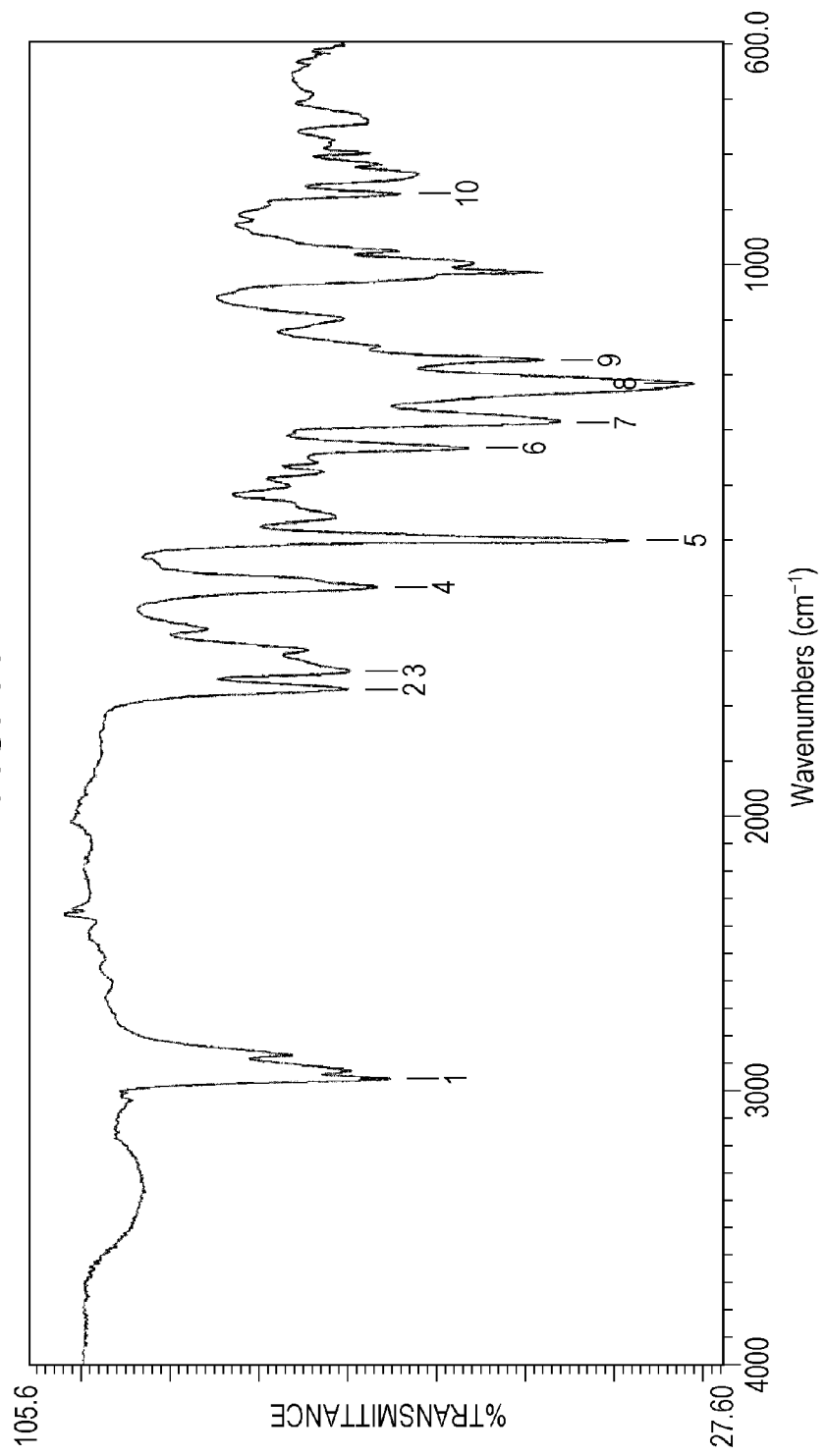
FIG. 14 is a diagram illustrating an IR spectrum of a product of a reaction formula (1-14) of Example 7.
Figure 15:
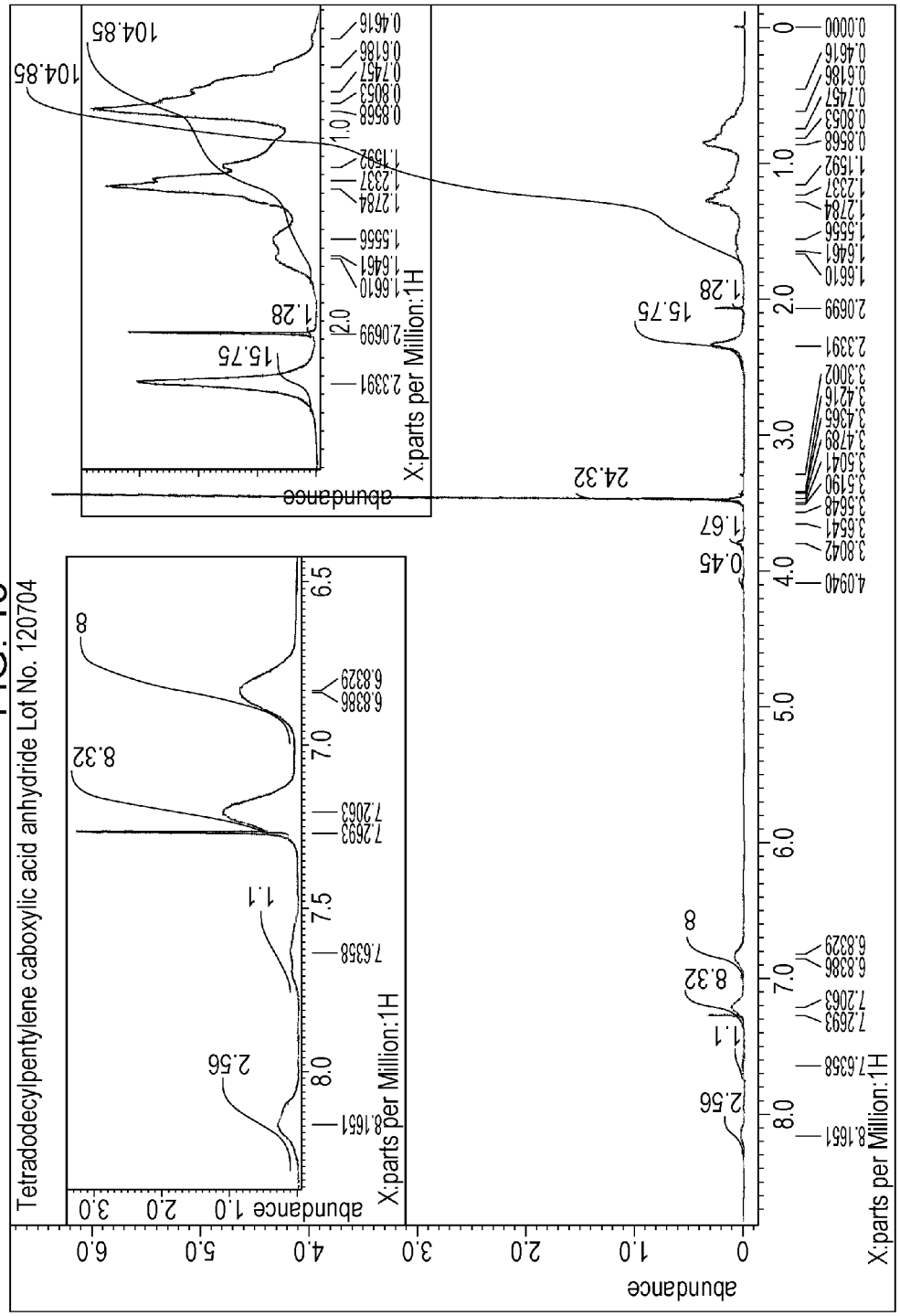
FIG. 15 is a diagram illustrating results of $^1$H-NMR of the product of the reaction formula (1-14) of Example 7.

Results of the IR spectrum are shown in FIG. 14 and results of $^1$H-NMR are shown in FIG. 15. From the results obtained from the NMR method shown in FIG. 15, the number of Hs (hydrogen) of an alkyl group was compared to the total amount of the number of Hs of a benzene ring. As a result, H of the alkyl group: H of the benzene ring was 19.98H: 104.80H (theoretical value 20H:100H).

(Reaction Process 5)

A reaction represented by the reaction formula (1-15) was performed as a reaction process 5 using the compound obtained by the reaction process 4.

5 g (3.48 mmol) of 1,6,7,12-tetrakis(4-dodecylphenoxy) perylene-3,4,9-10-tetracarboxylic acid dianhydride, 2.4 g (15.34 mmol) of 2,3-diaminonaphthalene, 1.2 g of pyrazine (15.34 mmol), 50 g of phenol, and 50 mL of toluene were added to 200 mL of a three-necked flask. The temperature of the mixed solution was increased and water secondarily produced in the system was extracted to out of the system using azeotropic dehydration with toluene. 100 g of phenol was added thereto at a distillation temperature of 100° C., the temperature thereof was increased to 145° C., and the reaction liquid was reacted by stirring for 24 hours. After the stirring reaction was terminated, the temperature of the reaction liquid was cooled to room temperature, and the reaction liquid was extracted in 1000 mL of methanol such that crystals were deposited. The crystals were filtered, slurry-washed using 1000 mL of methanol again, and then crystals were collected by filtration. The obtained crystals were dissolved in 200 mL of methylene chloride and then filtered. There were substantially no insoluble materials. A filtrate was purified by silica gel chromatography (120 g of silica gel) using an eluent obtained by mixing a 1:1 ratio of methylene chloride and hexane and 4.4 g of a main fraction was obtained. 4.4 g of the main fraction was dissolved in 100 mL of methylene chloride, 0.2 g of activated carbon was added thereto, and the mixture was stirred and then filtered. The filtrate was concentrated, hexane-substituted, and concentrated and dried. The obtained dried material was dispersed in methanol, crystals were collected by filtration, and then dried at room temperature. The wet weight of an obtained product was 8.0 g, the dry weight thereof was 3.9 g, and the yield thereof was 67.2%.

[Chem. 46]

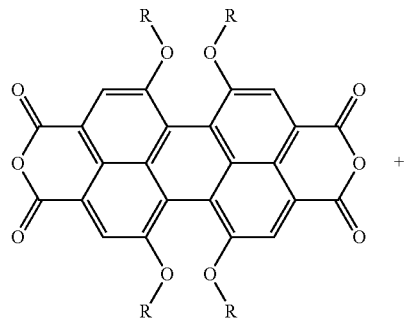

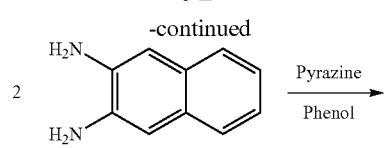

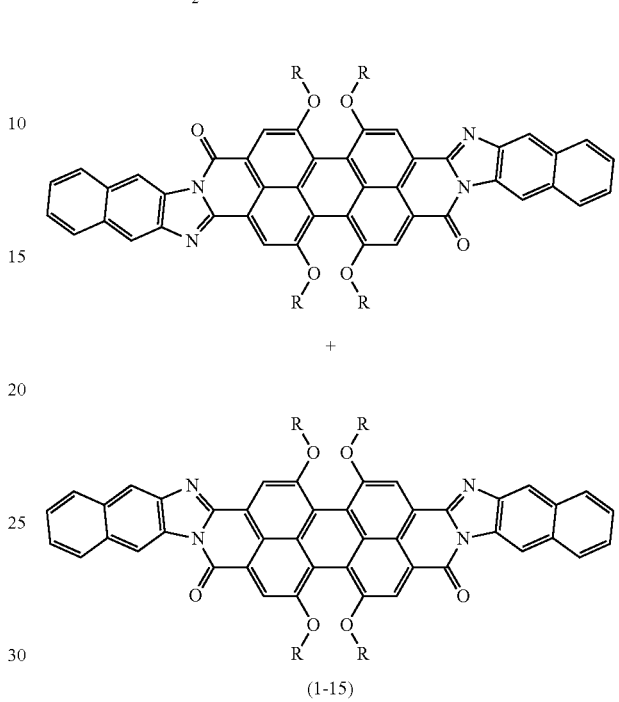

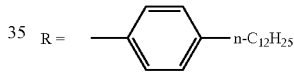

Figure 16:
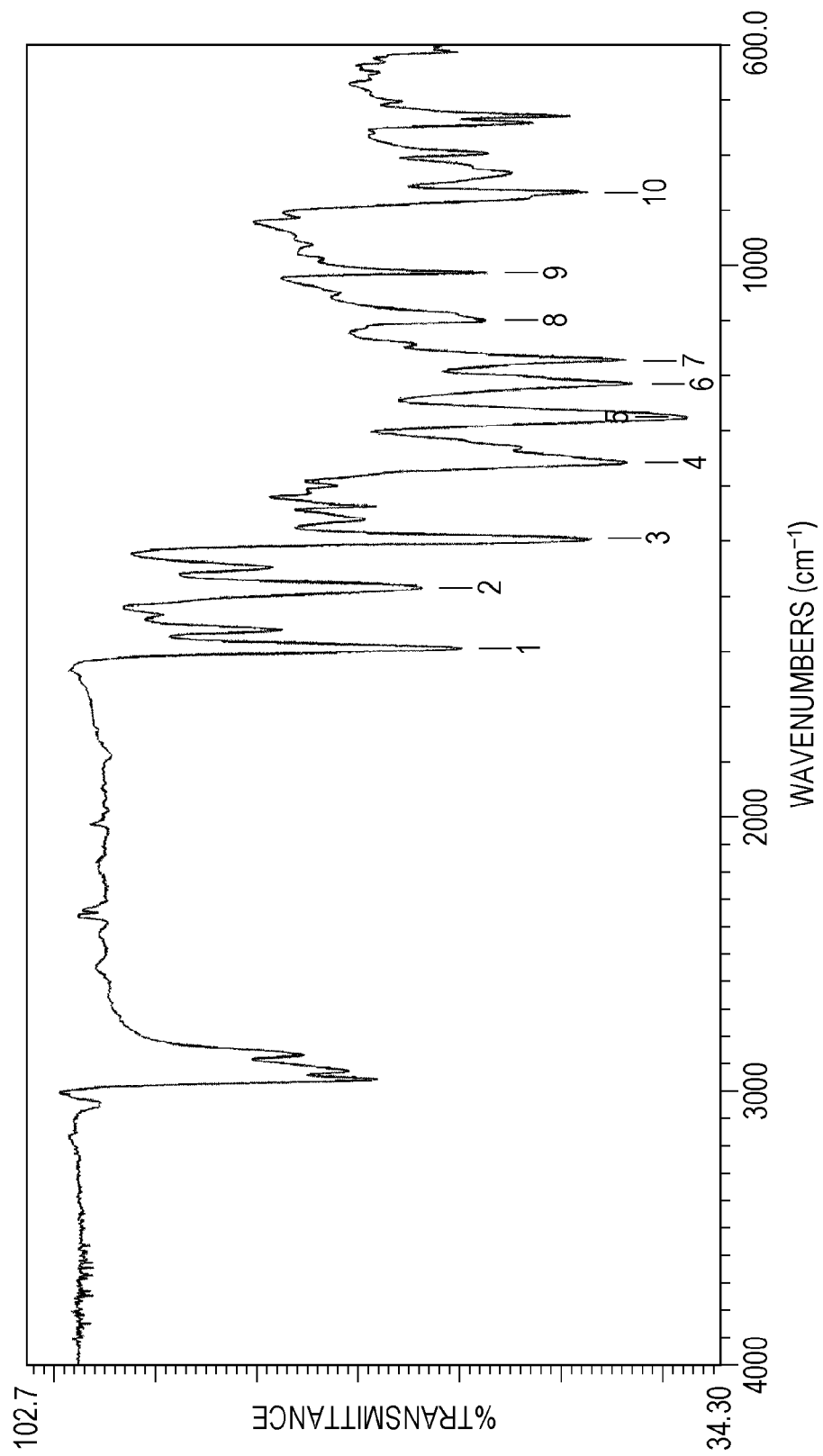
FIG. 16 is a diagram illustrating an IR spectrum of a product of a reaction formula (1-15) of Example 7.
Figure 17:
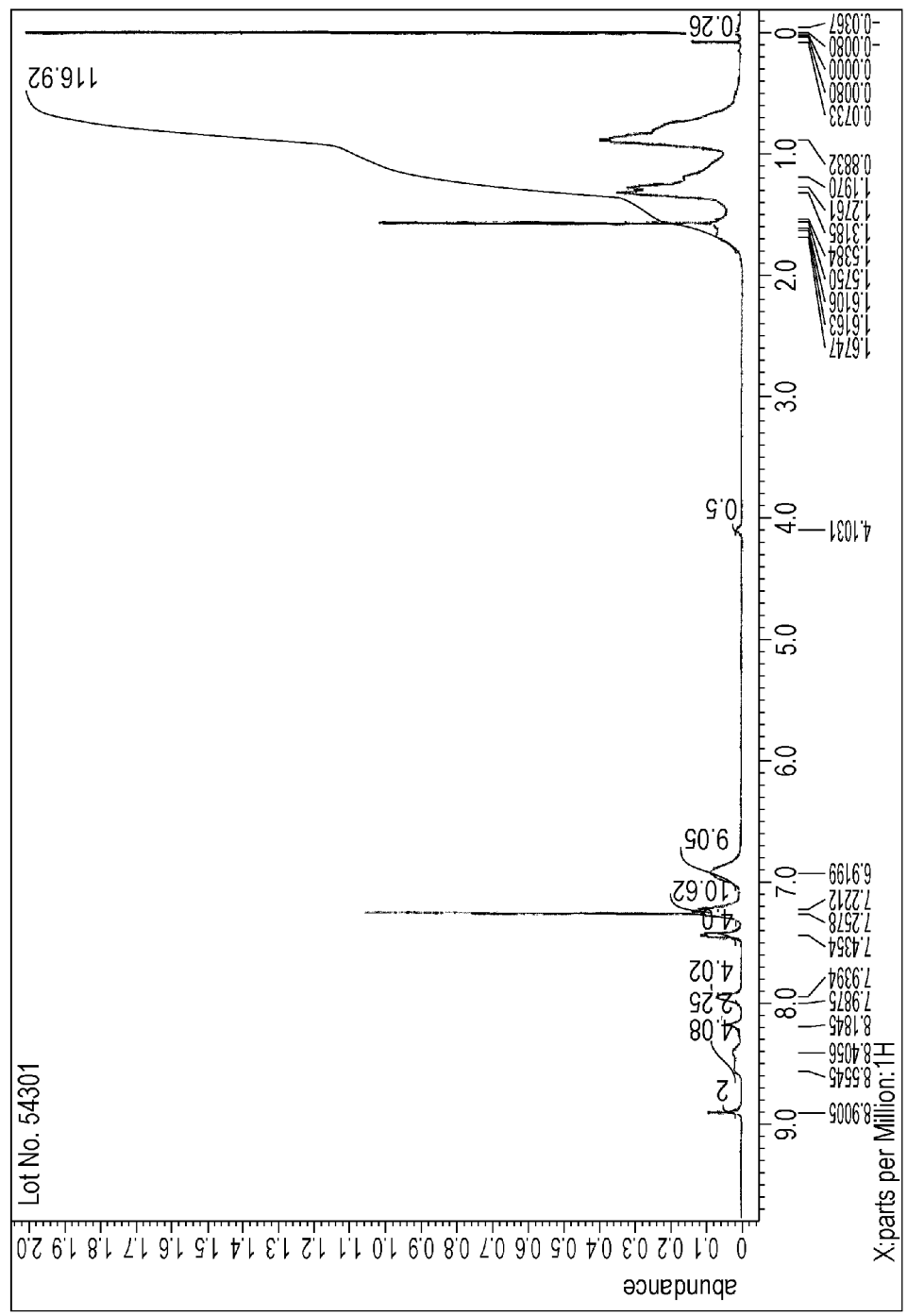
FIG. 17 is a diagram illustrating results of $^1$H-NMR of the product of the reaction formula (1-15) of Example 7.

The IR spectrum and the $^1$H-NMR spectrum of the obtained product are shown in FIGS. 16 and 17. As the results shown in FIG. 17, the number of Hs (hydrogen) of an alkyl group was compared to the total amount of the number of Hs of a benzene ring. As a result, H of the alkyl group: H of the benzene ring was 36.0H:116.9H (theoretical value 32H: 100H).

Figure 18:
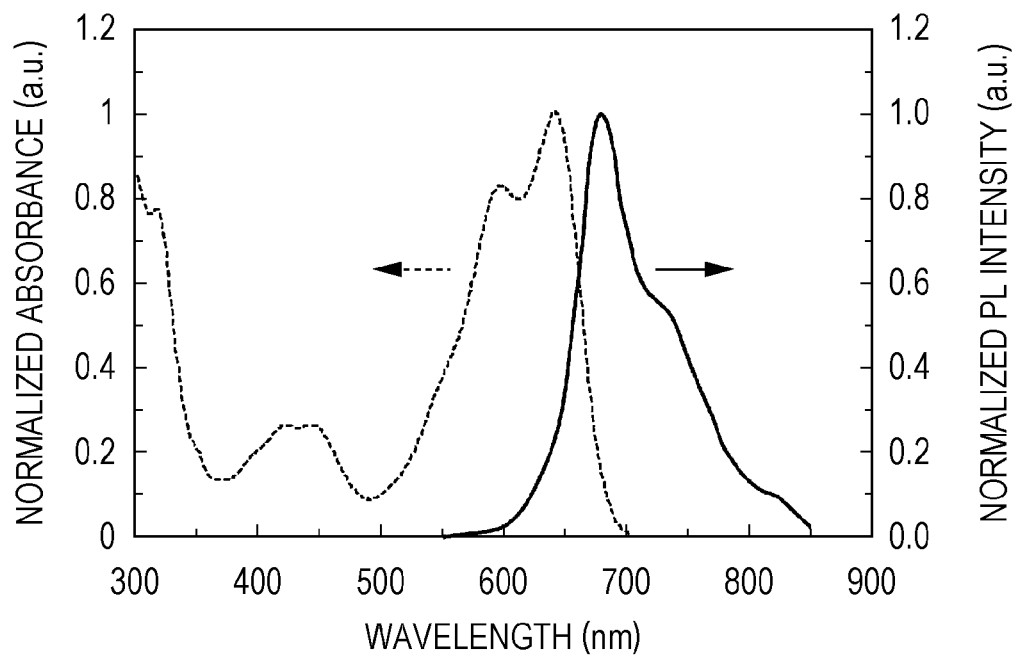
FIG. 18 is a diagram illustrating an absorption spectrum and a fluorescence spectrum of a compound of Example 7.
Figure 19:
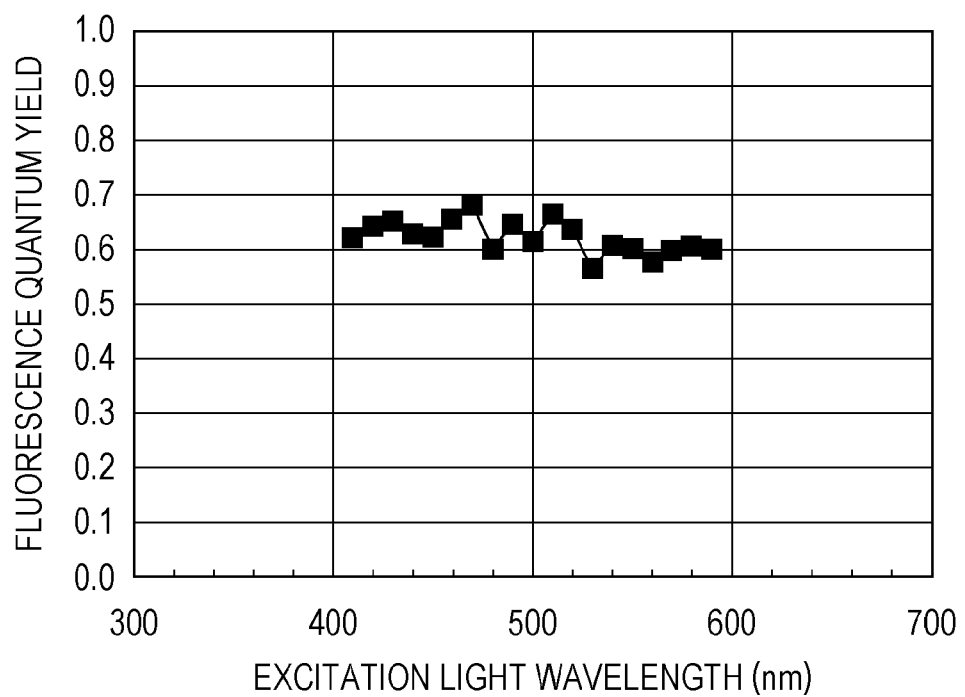
FIG. 19 is a diagram illustrating the relationship between an excitation light wavelength and a fluorescence quantum yield of the compound of Example 7.

The absorption spectrum and the fluorescence spectrum of the obtained product are shown in FIG. 18. A relationship between the excitation light wavelength and the fluorescence quantum yield of the obtained product is shown in FIG. 19.

An absorption peak wavelength λmax was 642 nm. The fluorescence peak wavelength was 681 nm and the average fluorescence quantum yield was 0.63.

Example 8

Process of Producing Compound (IIb)

Compounds represented by the following formulae (3A)-101 and (3B)-101 (hereinafter, simply written as a "compound (3A)-101" and a "compound (3B)-101" respectively) are produced as compounds (II) by following the procedures described below. The compounds (3A)-101 and (3B)-101 are compounds (II) in which four benzene ring skeletons bonded to a carbon atom on the fourth position are amino groups and others are all hydrogen atoms in Zs, all $R^{11}$s represent a hydrogen atom, and $n_{11}$ is 0. In addition, the same compounds are used herein as the compounds (IIc) and (IId).

A compound (1,6,7,12-tetrachloroperylene-3,4,9,10-tetracarboxylic acid dianhydride, hereinafter, simply written as a "compound (3)-101e") represented by the following formula (3)-101e as a compound (IIe) and a compound (1,2-diaminobenzene, hereinafter, simply written as a "compound (3)-101c") represented by the following formula (3)-101c as compounds (IIc) and (IId) are mixed with propionic acid. The amounts of the compound (3)-101c to be used is set to 4 molar times with respect to the compound (3)-101e.

The temperature of the mixed reaction liquid is increased and reacted at 140° C. for 6 hours.

Subsequently, the temperature of the reaction liquid is cooled to room temperature (25° C.), and deposited crystals are filtered, washed, and then dried, thereby obtaining a mixture of compounds represented by the following formulae (3A)-101b and (3B)-101b as the compounds (IIb) (hereinafter, simply written as a "compound (3A)-101b" and a "compound (3B)-101b" respectively).

(Process of Producing Compounds (II))

A mixture having the total amount of the compounds (3A)-101b and (3B)-101b, a compound represented by the following formula (IIa) (4-aminophenol, hereinafter, simply written as a "compound (3)-101a") as the compound (IIa), and potassium carbonate are mixed with N-methylpyrrolidone. The amounts of the compound (3)-101a and potassium carbonate to be used are respectively set to 6 molar times with respect to the total amount of the compounds (3A)-101b and (3B)-101b. The amount of N-methylpyrrolidone to be used is set to 20 mass times with respect to the compound (3)-101e.

The temperature of the mixed reaction liquid is increased to be reacted at 140° C. for 24 hours. Through this reaction, compounds (3A)-101 and (3B)-101 are obtained as the compounds (II).

Next, after the temperature of the reaction liquid is cooled to room temperature (25° C.), deposited crystals are filtered, washed, and subjected to silica gel column chromatography, a fraction containing the compound (3A)-101 is separated, an operation of separating a target is performed, the obtained fraction is concentrated, and a compound (3A)-101 is obtained by drying the obtained concentrated material under reduced pressure. Furthermore, a compound (3B)-101 is obtained by performing the same operation described above.

The compound (3A)-101 has a light absorption peak wavelength of 675 nm and is capable of absorbing light having a long wavelength.

Further, the peak wavelength of absorbable light is a value acquired by B3LYP/6-31G using Gaussian09 (manufactured by Gaussian, Inc.). The same applies to the examples below.

[Chem. 47]

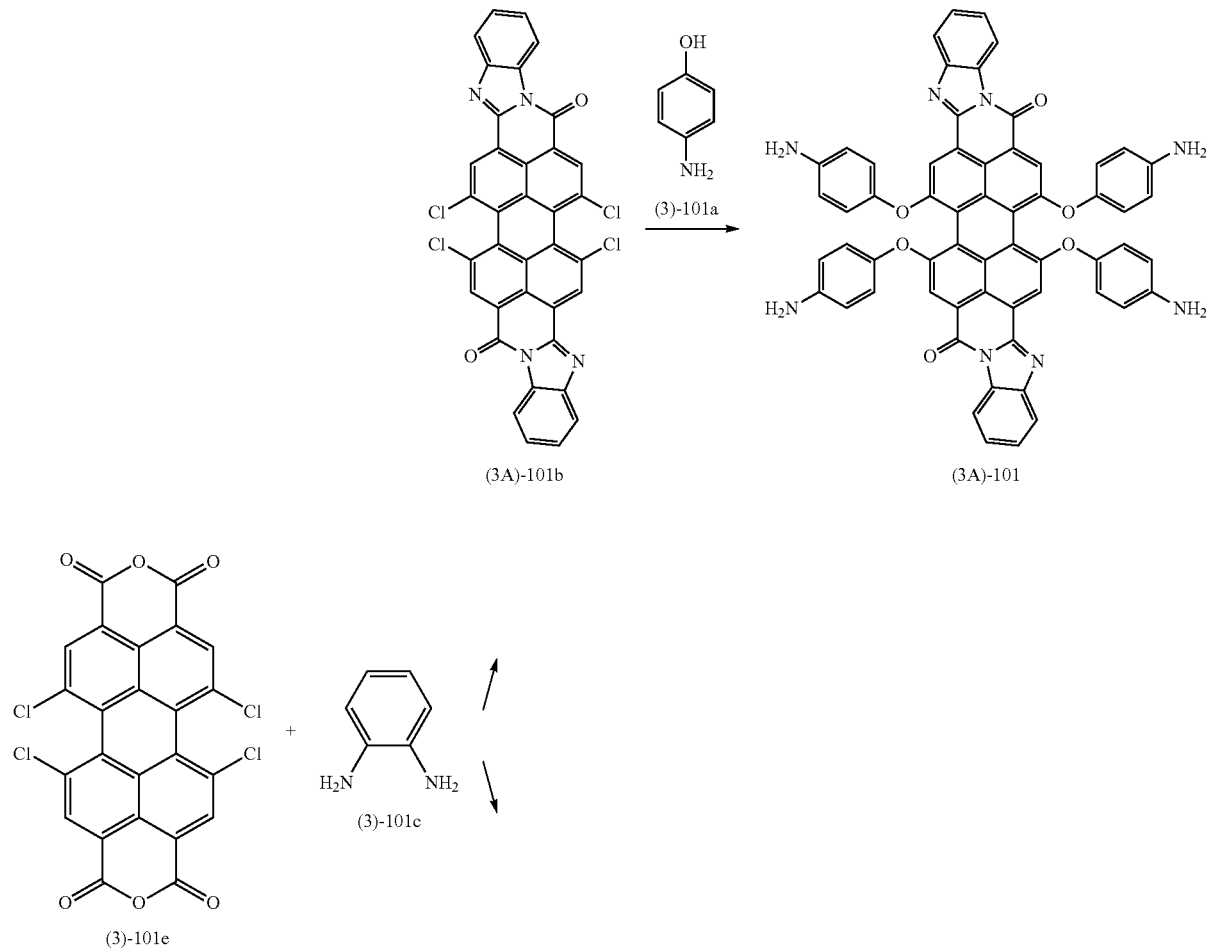

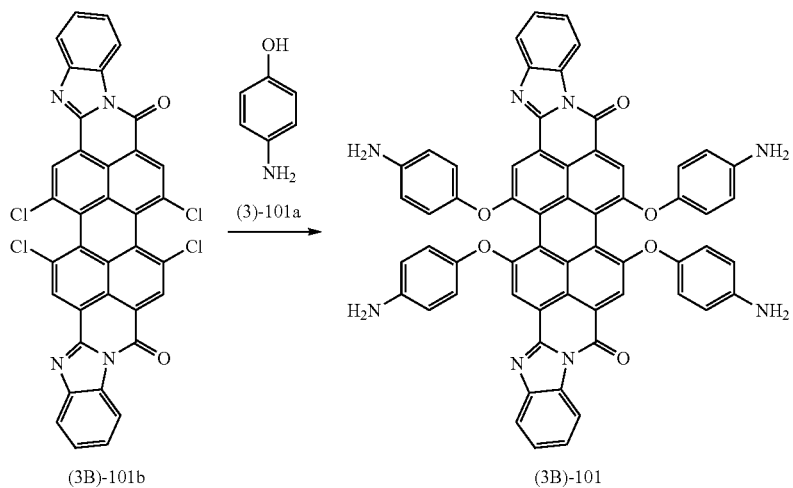

(3B)-101b             (3B)-101

Example 9

Compounds represented by the following formulae (3A)-102 and (3B)-102 (hereinafter, simply written as a "compound (3A)-102" and a "compound (3B)-102" respectively) are produced as the compounds (II) in the same method as that described in Example 1 except that a compound (3-aminophenol, hereinafter, simply written as a "compound (3)-102a") represented by the following formula (3)-102a is used instead of the compound (3)-101a as the compound (IIa). The compound (IIb) is produced through compounds represented by the following formulae (3A)-101b and (3B)-101b. The compounds (3A)-102 and (3B)-102 are compounds (II) in which four benzene ring skeletons bonded to a carbon atom on the third position are amino groups and others are all hydrogen atoms in Zs, all $R^{11}$s represent a hydrogen atom, and $n_{11}$ is 0.

The compound (3A)-102 can absorb light having a peak wavelength of 647 nm to 659 nm.

The reason why the peak wavelength has such a width described above is considered that a benzene ring skeleton to which Z is bonded is difficult to rotate when a relatively bulky group is included as Z, the benzene ring skeleton is difficult to rotate using a bond of adjacent oxygen atoms as an axis, and one or more stereoisomers are present. In the examples below, speculatively, the same applies to the compounds whose peak wavelength has a width.

[Chem. 48]

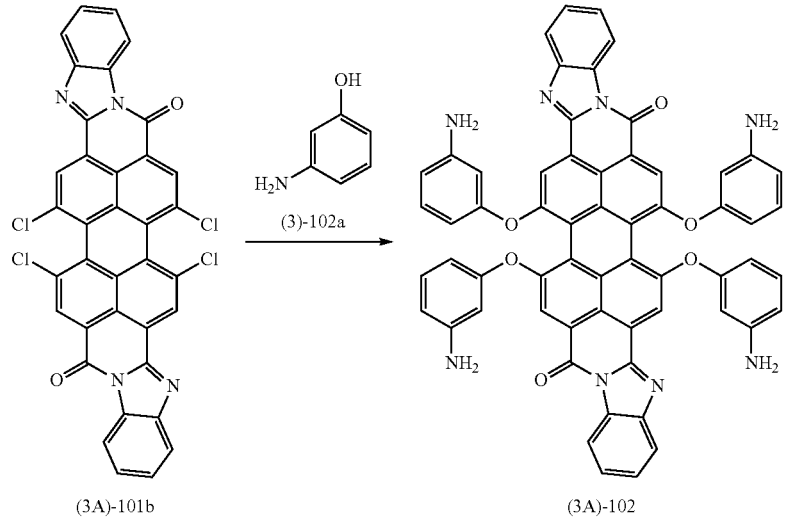

(3A)-101b             (3A)-102

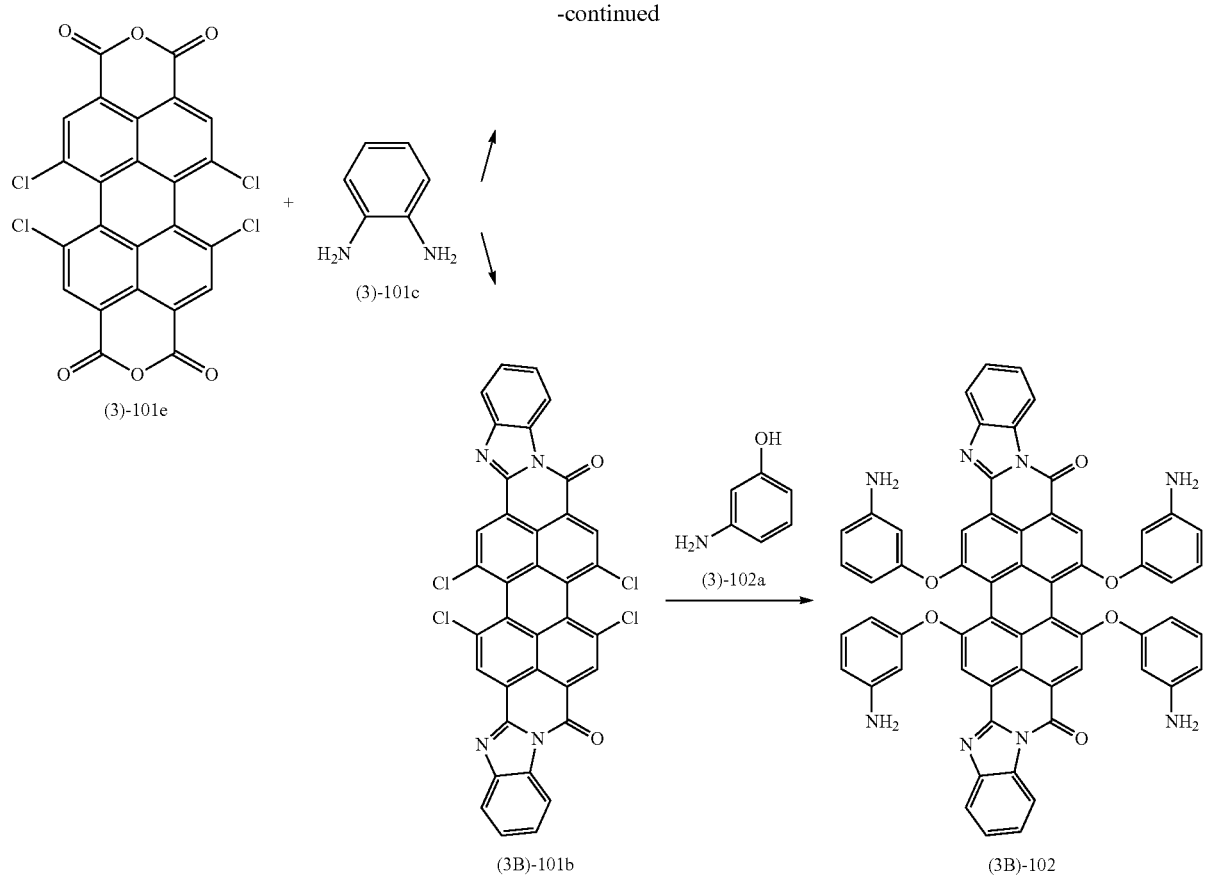

Example 10

Compounds represented by the following formulae (3A)-103 and (3B)-103 (hereinafter, simply written as a "compound (3A)-103" and a "compound (3B)-103" respectively) are produced as the compounds (II) in the same method as that described in Example 1 except that a compound (2-aminophenol, hereinafter, simply written as a "compound (3)-103a") represented by the following formula (3)-103a is used instead of the compound (3)-101a as the compound (IIa). The compound (IIb) is produced through compounds represented by the following formulae (3A)-101b and (3B)-101b. The compounds (3A)-103 and (3B)-103 are compounds (II) in which four benzene ring skeletons bonded to a carbon atom on the second position are amino groups and others are all hydrogen atoms in Zs, all $R^{11}$s represent a hydrogen atom, and $n_{11}$ is 0.

The compound (3A)-103 can absorb light having a peak wavelength of 687 nm to 722 nm.

[Chem. 49]

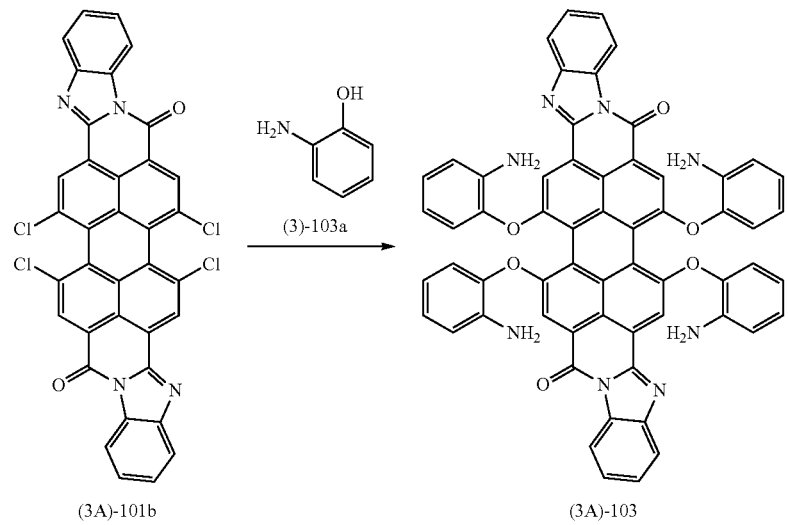

-continued

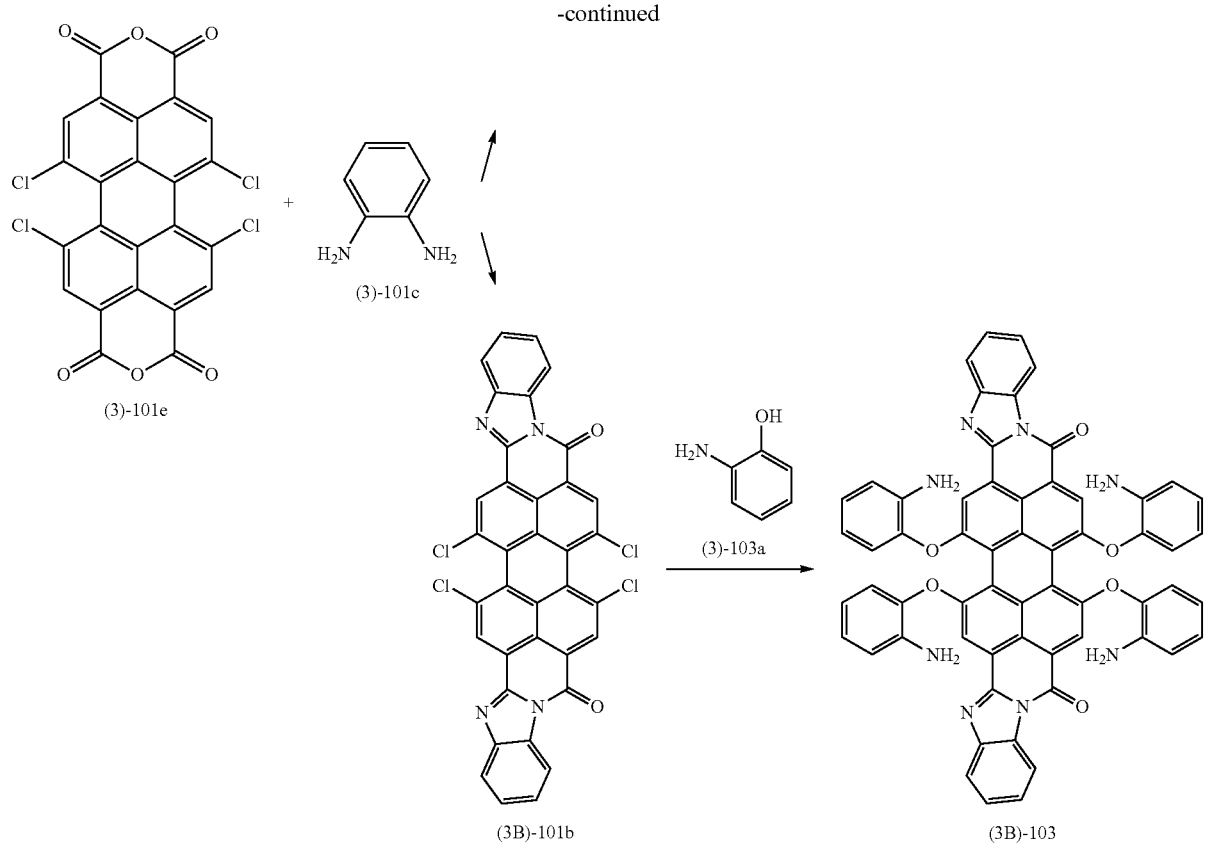

Example 11

Compounds represented by the following formulae (3A)-104 and (3B)-104 (hereinafter, simply written as a "compound (3A)-104" and a "compound (3B)-104" respectively) are produced as the compounds (II) in the same method as that described in Example 1 except that a compound (4-dimethylaminophenol, hereinafter, simply written as a "compound (3)-104a") represented by the following formula (3)-104a is used instead of the compound (3)-101a as the compound (IIa). The compound (IIb) is produced through compounds represented by the following formulae (3A)-101b and (3B)-101b. The compounds (3A)-104 and (3B)-104 are compounds (I) in which four benzene ring skeletons bonded to a carbon atom on the fourth position are dimethylamino groups and others are all hydrogen atoms in Zs, all $R^{11}$s represent a hydrogen atom, and $n_{11}$ is 0.

The compound (3A)-104 can absorb light having a peak wavelength of 705 nm.

[Chem. 50]

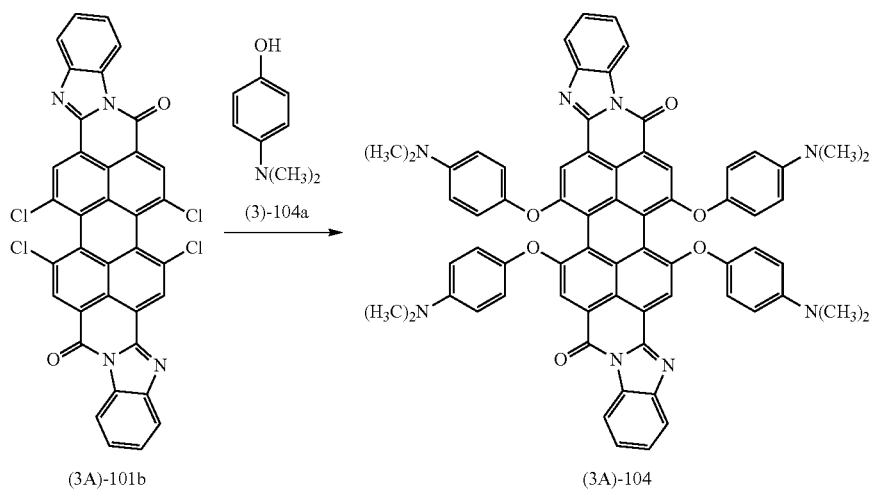

-continued

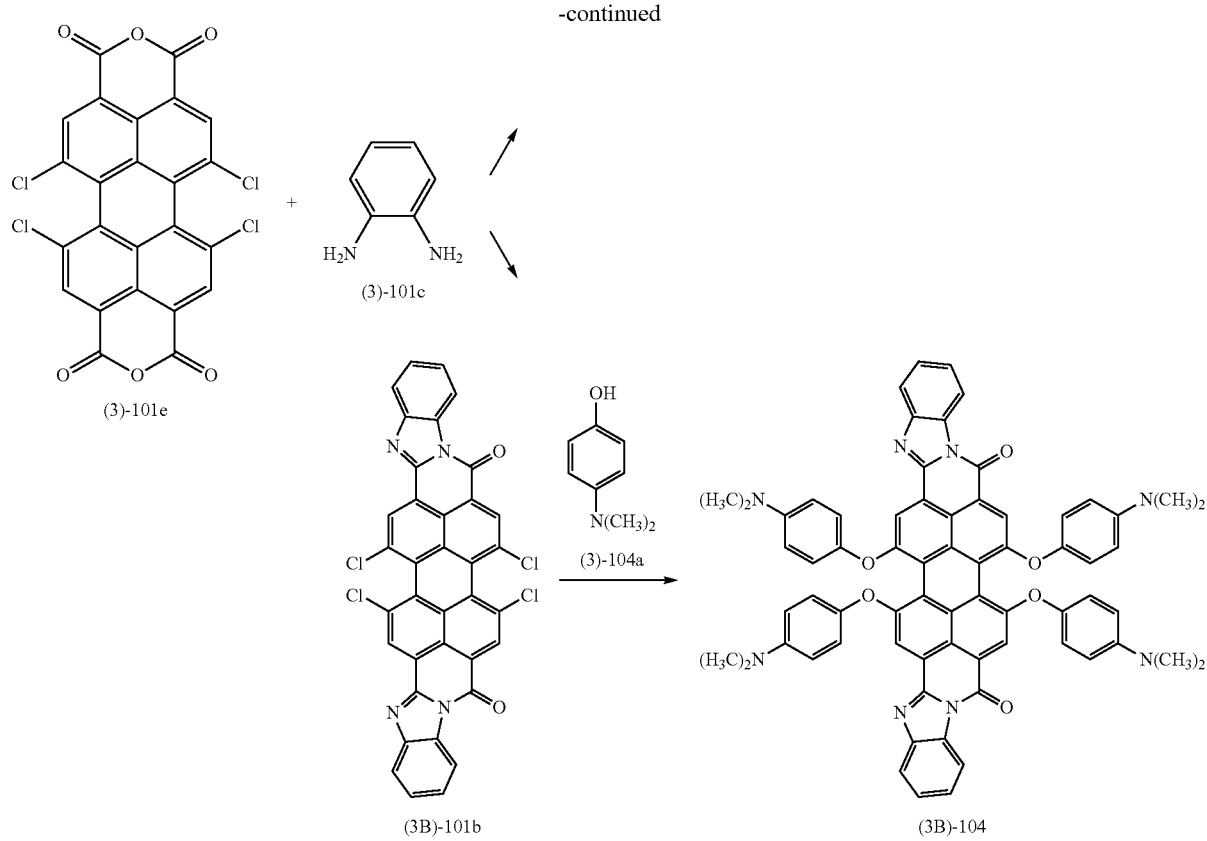

Example 12

Compounds represented by the following formulae (3A)-105 and (3B)-105 (hereinafter, simply written as a "compound (3A)-105" and a "compound (3B)-105" respectively) are produced as the compounds (II) in the same method as that described in Example 1 except that a compound (3,5-diaminophenol, hereinafter, simply written as a "compound (3)-105a") represented by the following formula (3)-105a is used instead of the compound (3)-101a as the compound (IIa). The compound (IIb) is produced through compounds represented by the following formulae (3A)-101b and (3B)-101b. The compounds (3A)-105 and (3B)-105 are compounds (II) in which eight benzene ring skeletons bonded to carbon atoms on the third position and the fifth position are amino groups and others are all hydrogen atoms in Zs, all $R^{11}$s represent a hydrogen atom, and $n_{11}$ is 0.

The compound (3A)-105 can absorb light having a peak wavelength of 656 nm.

[Chem. 51]

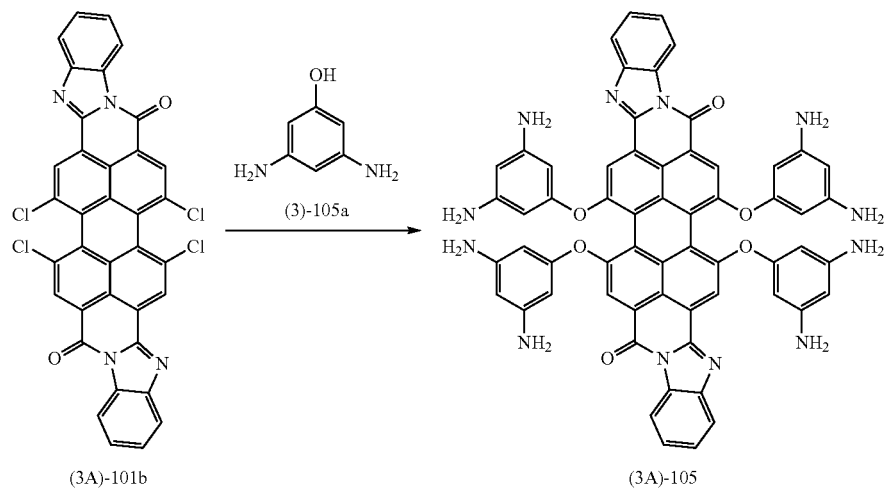

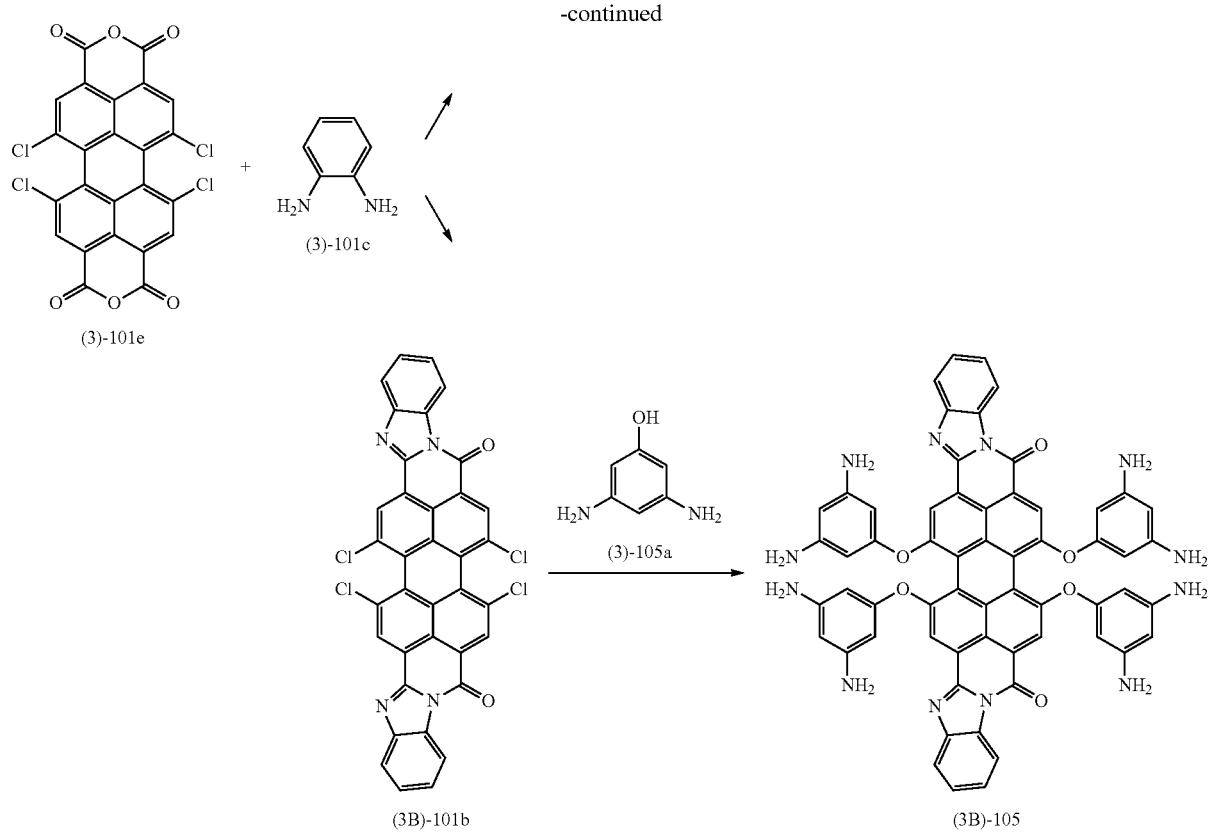

Example 13

Compounds represented by the following formulae (3A)-106 and (3B)-106 (hereinafter, simply written as a "compound (3A)-106" and a "compound (3B)-106" respectively) are produced as the compounds (II) in the same method as that described in Example 1 except that a compound (2,3-diaminophenol, hereinafter, simply written as a "compound (3)-106a") represented by the following formula (3)-106a is used instead of the compound (3)-101a as the compound (IIa). The compound (IIb) is produced through compounds represented by the following formulae (3A)-101b and (3B)-101b. The compounds (3A)-106 and (3B)-106 are compounds (II) in which eight benzene ring skeletons bonded to carbon atoms on the second position and the third position are amino groups and others are all hydrogen atoms in Zs, all $R^{11}$'s represent a hydrogen atom, and $n_{11}$ is 0.

The compound (3A)-106 can absorb light having a peak wavelength of 670 nm.

[Chem. 52]

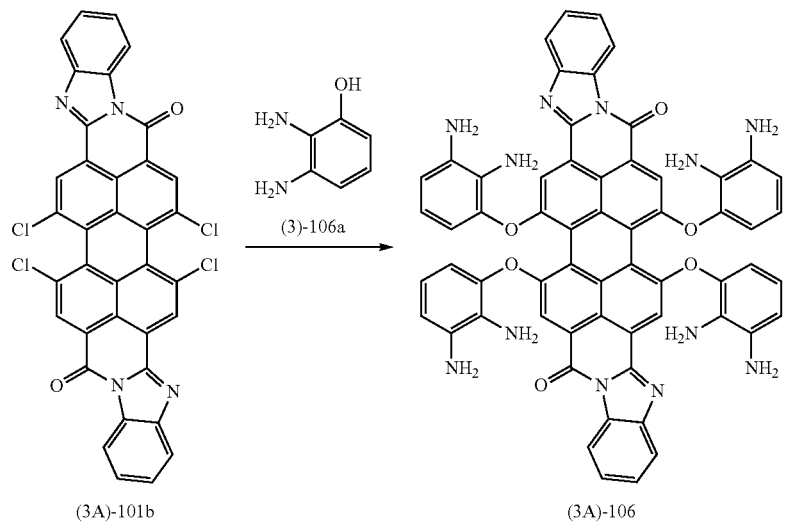

-continued

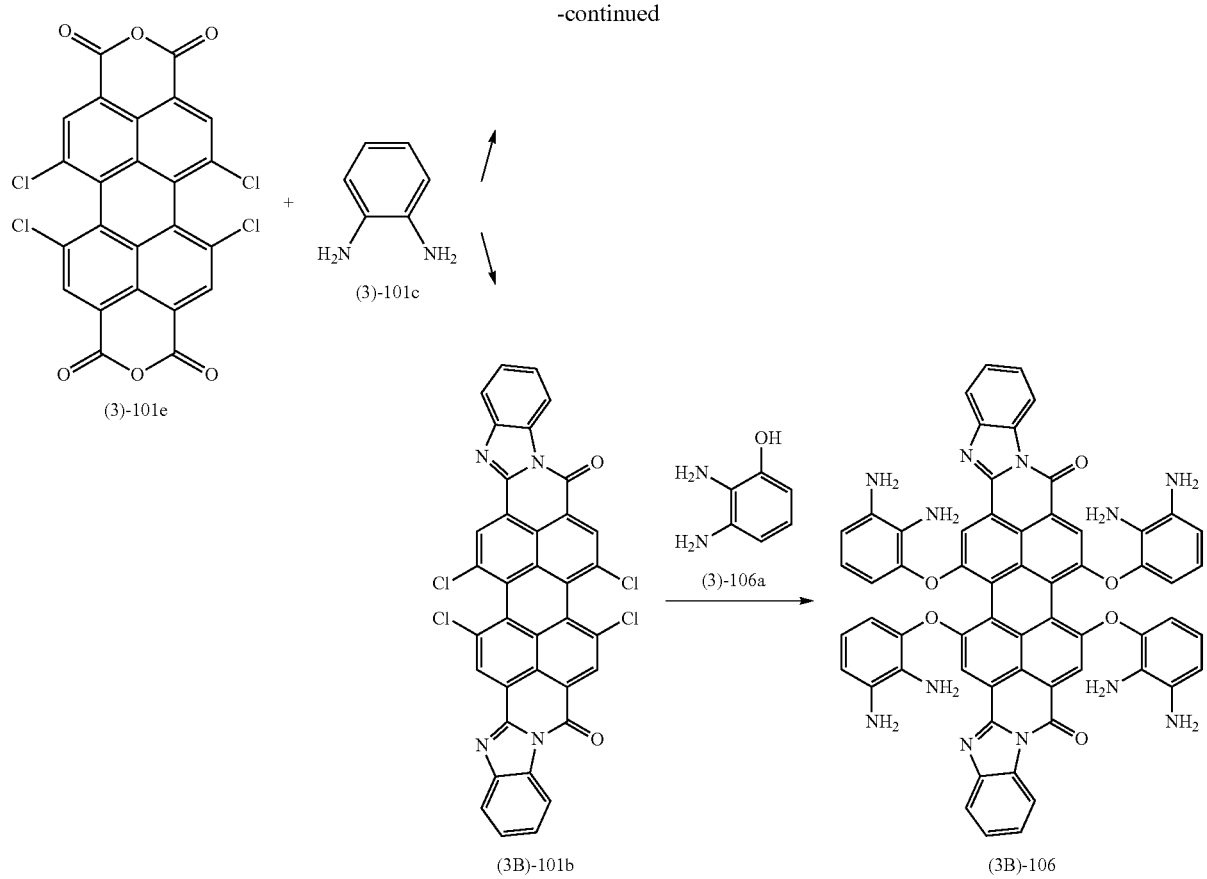

Example 14

Compounds represented by the following formulae (3A)-107 and (3B)-107 (hereinafter, simply written as a "compound (3A)-107" and a "compound (3B)-107" respectively) are produced as the compounds (II) in the same method as that described in Example 1 except that a compound (3,4-dimethoxyphenol, hereinafter, simply written as a "compound (3)-107a") represented by the following formula (3)-107a is used instead of the compound (3)-101a as the compound (IIa). The compound (IIb) is produced through compounds represented by the following formulae (3A)-101b and (3B)-101b. The compounds (3A)-107 and (3B)-107 are compounds (II) in which eight benzene ring skeletons bonded to a carbon atom on the third position and the fourth position are methoxy groups and others are all hydrogen atoms in Zs, all $R^{11}$s represent a hydrogen atom, and $n_{11}$ is 0.

The compound (3A)-107 can absorb light having a peak wavelength of 656 nm.

[Chem. 53]

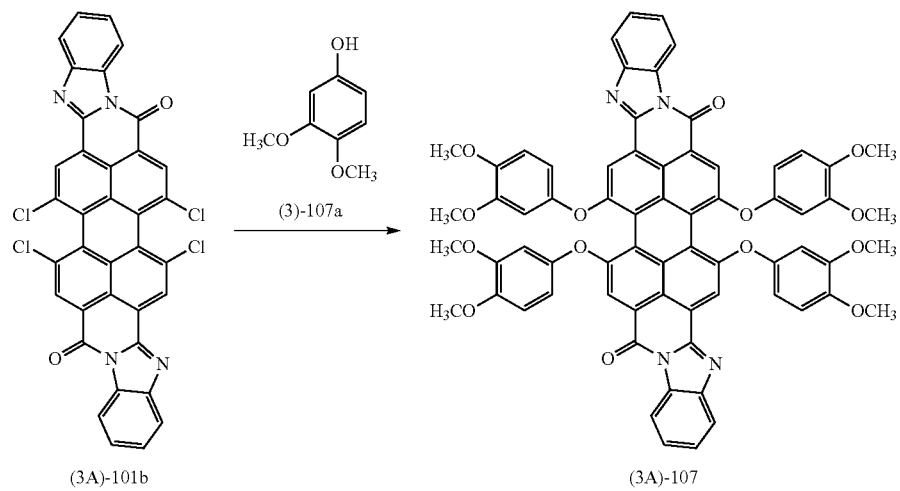

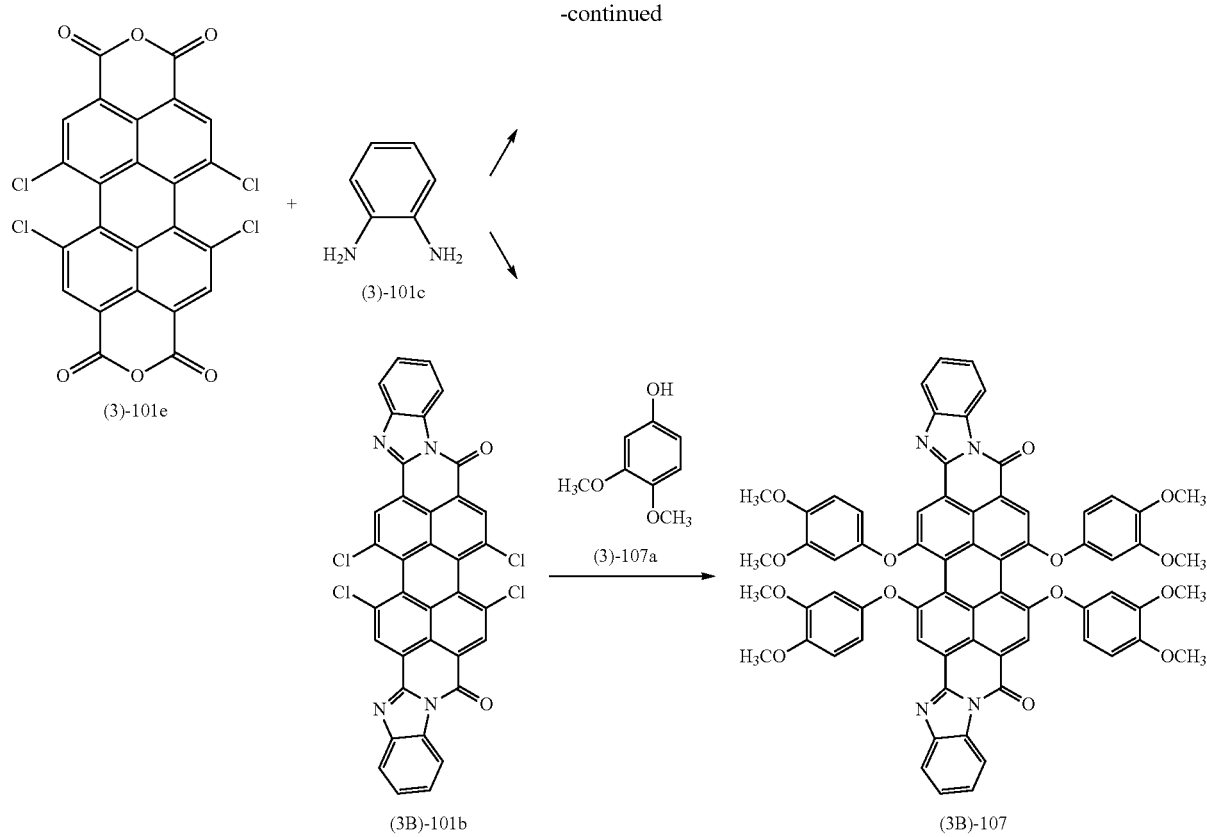

(3)-101e (3)-101c (3B)-101b (3)-107a (3B)-107

Example 15

Compounds represented by the following formulae (3A)-108 and (3B)-108 (hereinafter, simply written as a "compound (3A)-108" and a "compound (3B)-108" respectively) are produced as the compounds (II) in the same method as that described in Example 1 except that a compound (2,3-diaminonaphthalene, hereinafter, simply written as a "compound (3)-102c") represented by the following formula (3)-102c is used instead of the compound (3)-101c as the compounds (IIc) and (IId). The compound (IIb) is produced through compounds represented by the following formulae (3A)-102b and (3B)-102b. The compounds (3A)-108 and (3B)-108 are compounds (II) in which four benzene ring skeletons bonded to a carbon atom on the fourth position are amino groups and others are all hydrogen atoms in Zs, all $R^{11}$s represent a hydrogen atom, and $n_{11}$ is 0.

The compound (3A)-108 can absorb light having a peak wavelength of 695 nm.

[Chem. 54]

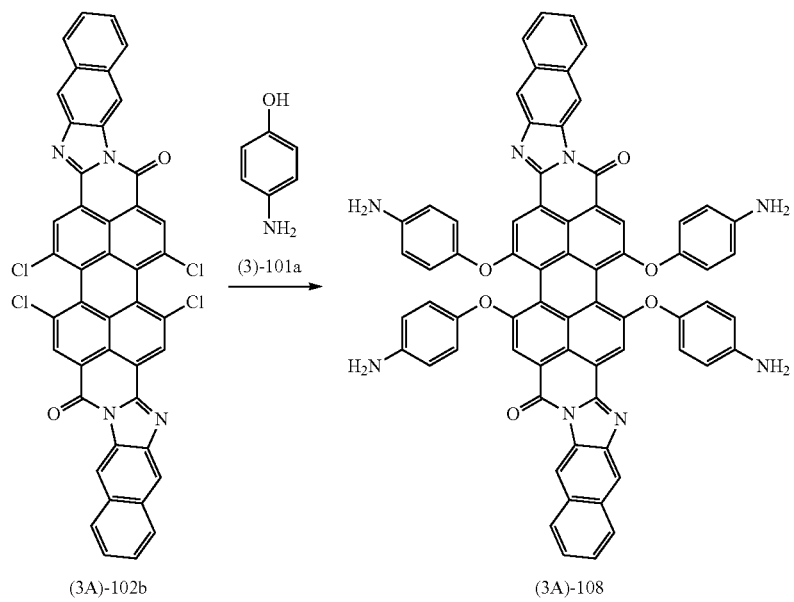

(3A)-102b (3)-101a (3A)-108

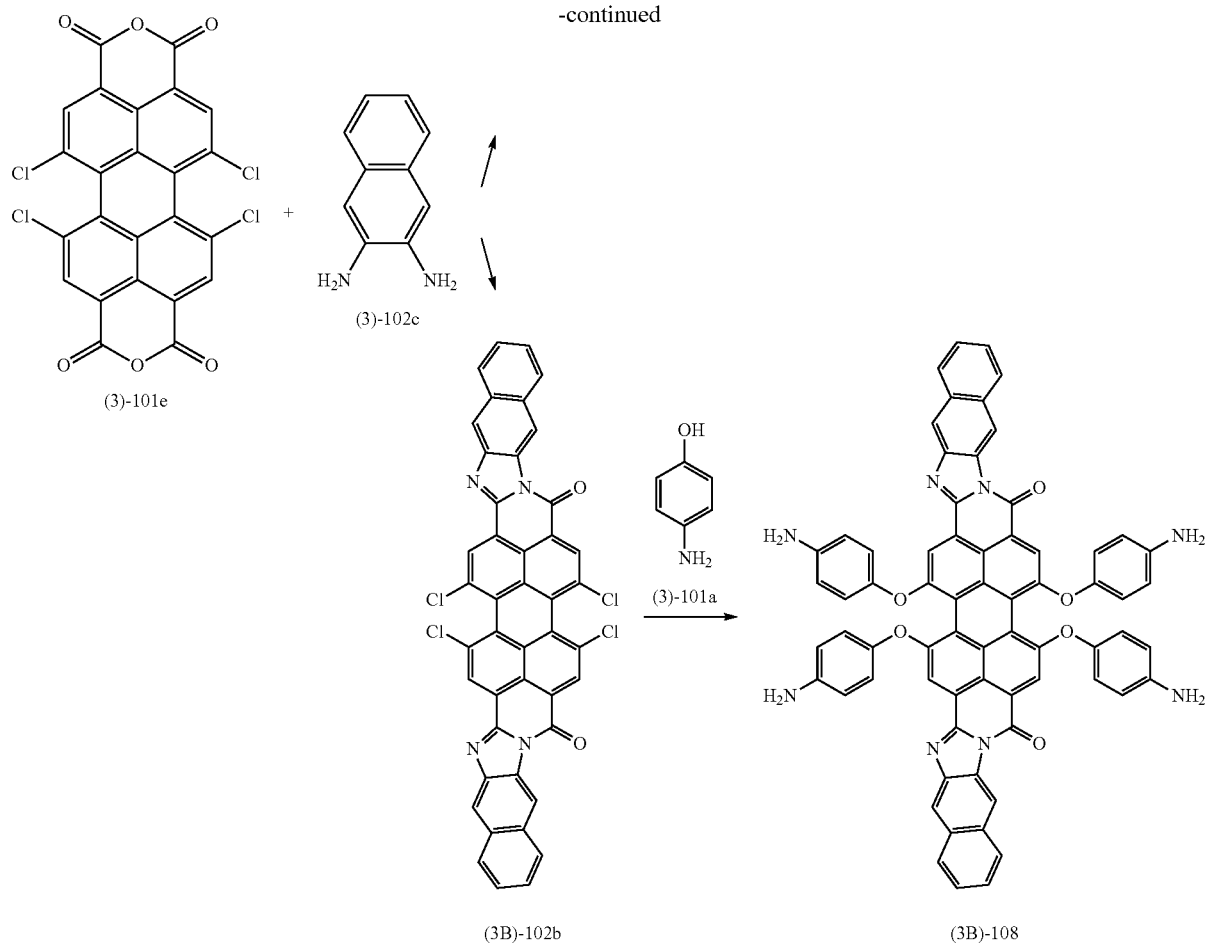

Example 16

Compounds represented by the following formulae (3A)-109 and (3B)-109 (hereinafter, simply written as a "compound (3A)-109" and a "compound (3B)-109" respectively) are produced as the compounds (II) in the same method as that described in Example 1 except that a compound (2-amino-4-methoxyphenol, hereinafter, simply written as a "compound (3)-108a") represented by the following formula (3)-108a is used instead of the compound (3)-101a as the compound

[Chem. 55]

(IIa). The compound (IIb) is produced through compounds represented by the following formulae (3A)-101b and (3B)-101b. The compounds (3A)-109 and (3B)-109 are compounds (II) in which four benzene ring skeletons bonded to a carbon atom on the second position are amino groups, four benzene ring skeletons bonded to a carbon atom on the fourth position are methoxy groups, and others are all hydrogen atoms in Zs, all $R^{11}$s represent a hydrogen atom, and $n_{11}$ is 0.

The compound (3A)-109 can absorb light having a peak wavelength of 760 nm.

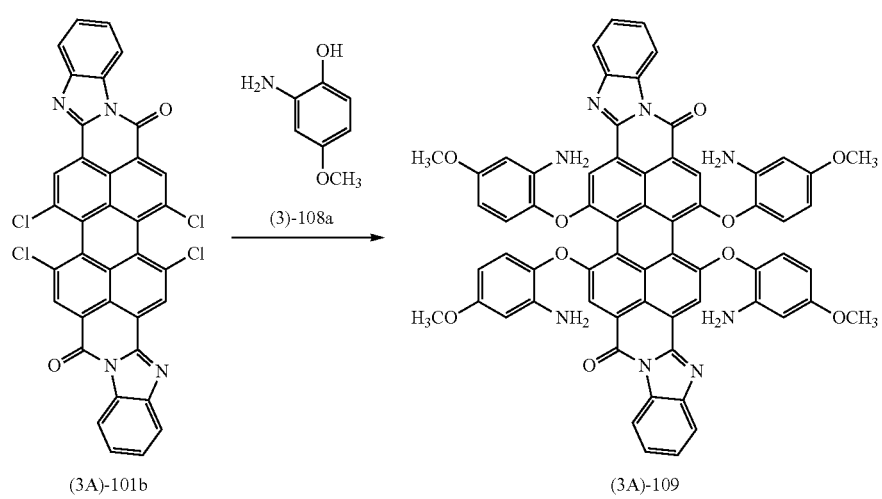

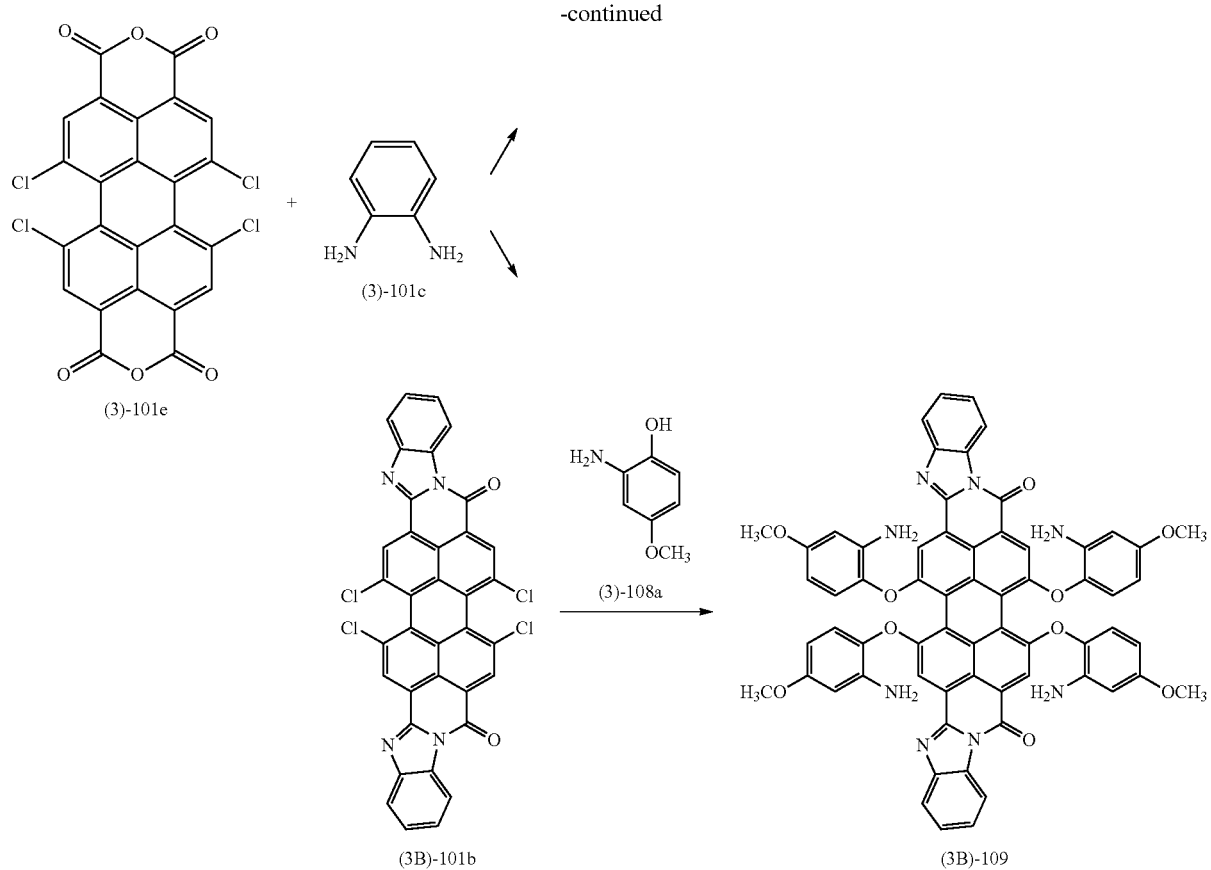

Example 17

Compounds represented by the following formulae (3A)-110 and (3B)-110 (hereinafter, simply written as a "compound (3A)-110" and a "compound (3B)-110" respectively) are produced as the compounds (II) in the same method as that described in Example 1 except that a compound (4-methoxyphenol, hereinafter, simply written as a "compound (3)-109a") represented by the following formula (3)-109a is used instead of the compound (3)-101a as the compound (IIa). The compound (IIb) is produced through compounds represented by the following formulae (3A)-101b and (3B)-101b. The compounds (3A)-110 and (3B)-110 are compounds (II) in which four benzene ring skeletons bonded to a carbon atom on the fourth position are methoxy groups and others are all hydrogen atoms in Zs, all $R^{11}$s represent a hydrogen atom, and $n_{11}$ is 0.

The compound (3A)-110 can absorb light having a peak wavelength of 651 nm.

[Chem. 56]

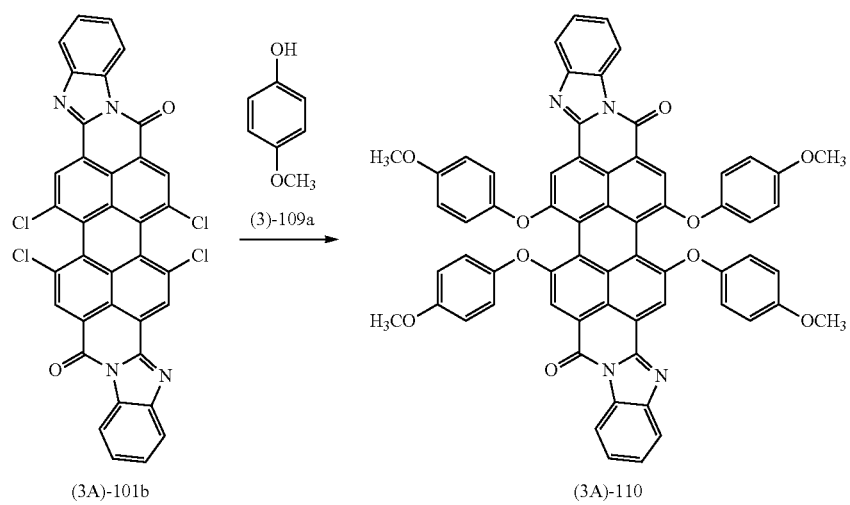

-continued

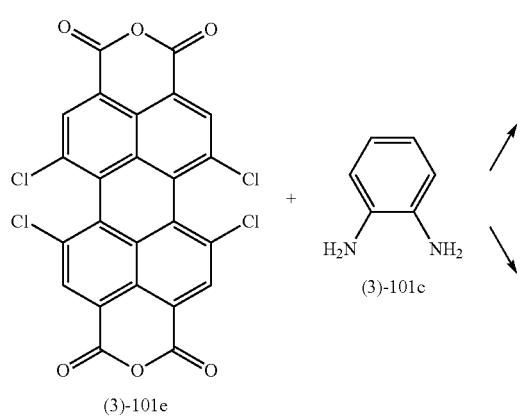

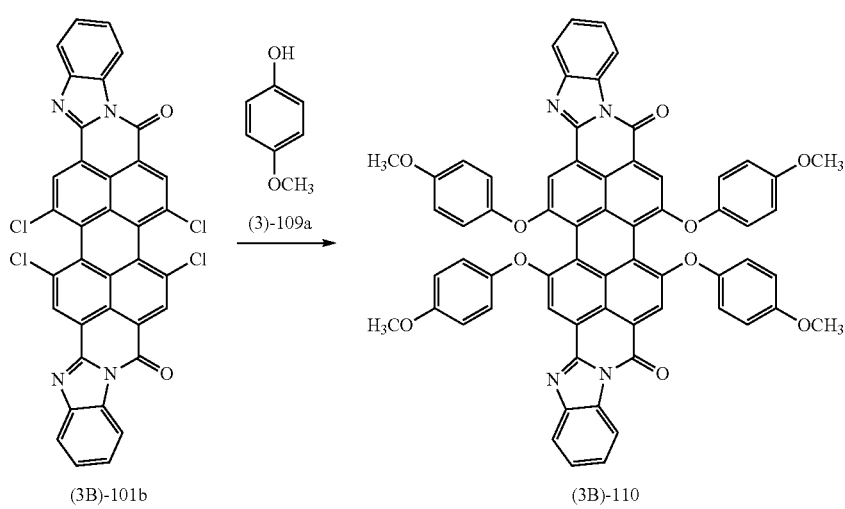

Production of Solar Cell Module

Example 18

The compounds (I) or (II) of Examples 1 to 17 are separately and respectively used as the phosphors 8, thereby producing the solar cell module 1 illustrated in FIGS. 1 to 3B.

Example 19

The compounds (I) or (II) of Examples 1 to 8 are separately and respectively used as the phosphors 8, and other phosphors other than the compounds (I) and (II) are used together, thereby producing the solar cell module 1 illustrated in FIGS. 1 to 3B.

INDUSTRIAL APPLICABILITY

The aspects of the present invention can be applied to a solar cell module and a solar power generation device.

REFERENCE SIGNS LIST

1, 1001 SOLAR CELL MODULE
2, 28, 30, 1002 LIGHT COLLECTOR (LIGHT GUIDE)
2*a*, 28*a* MAIN SURFACE (LIGHT INCIDENT SURFACE) OF LIGHT COLLECTOR
2*b* FIRST END SURFACE (LIGHT EMITTING SURFACE) OF LIGHT COLLECTOR
3, 1003 SOLAR CELL ELEMENT
7 TRANSPARENT BASE MATERIAL
8 PHOSPHOR (COMPOUND (I))
26 PHOSPHOR LAYER
1000 SOLAR POWER GENERATION DEVICE
L SOLAR LIGHT
L1 INCIDENT LIGHT

The invention claimed is:
1. A compound represented by the following general formula (IA0) or (IB0),

[Chem. 1]

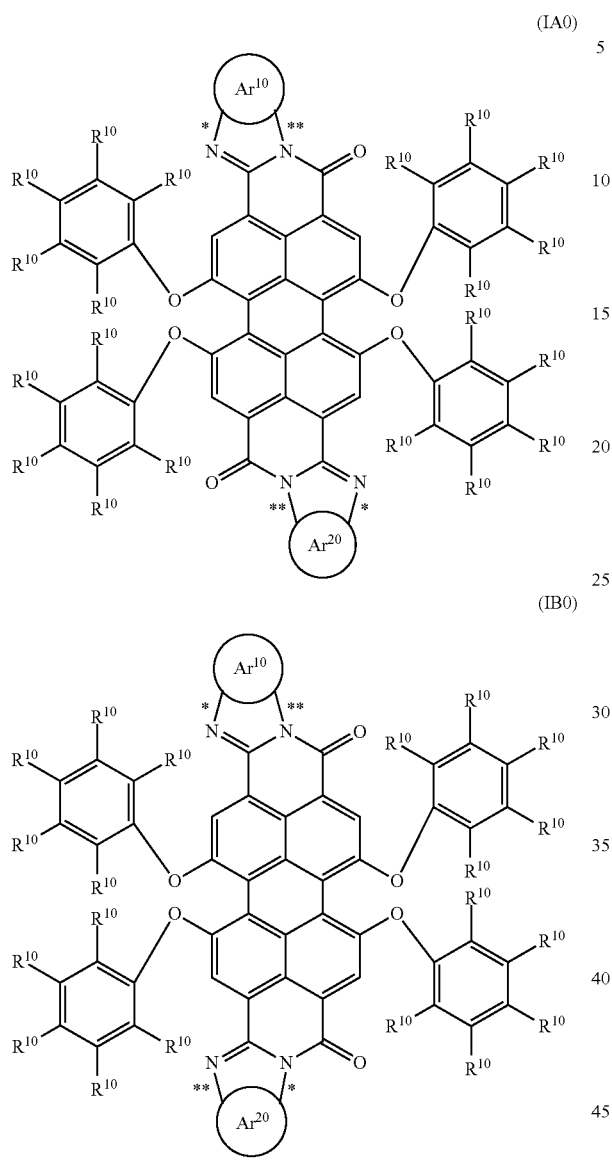

(in the formulae, $R^{10}$ represents a hydrogen atom, an alkyl group, an alkenyl group, an alkynyl group, an aryl group, an alkyl carbonyl amino group, or a group represented by the following general formula (z)-10 or (z)-20, and a plurality of $R^{10}$s may be the same as or different from one another;

$Ar^{10}$ and $Ar^{20}$ each independently represent a group represented by the following general formula (II)-110, (II)-120, (II)-130, (I)-210, or (I)-220;

$R^{10}$ represents a hydrogen atom or an alkyl group when $Ar^{10}$ and $Ar^{20}$ each independently represent a group represented by the following general formula (I)-210 or (I)-220; and a bond marked with a symbol "*" is attached to a carbon atom marked with the symbol "*" of the group, and a bond marked with a symbol "" is attached to a carbon atom marked with the symbol "" of the group),

[Chem. 2]

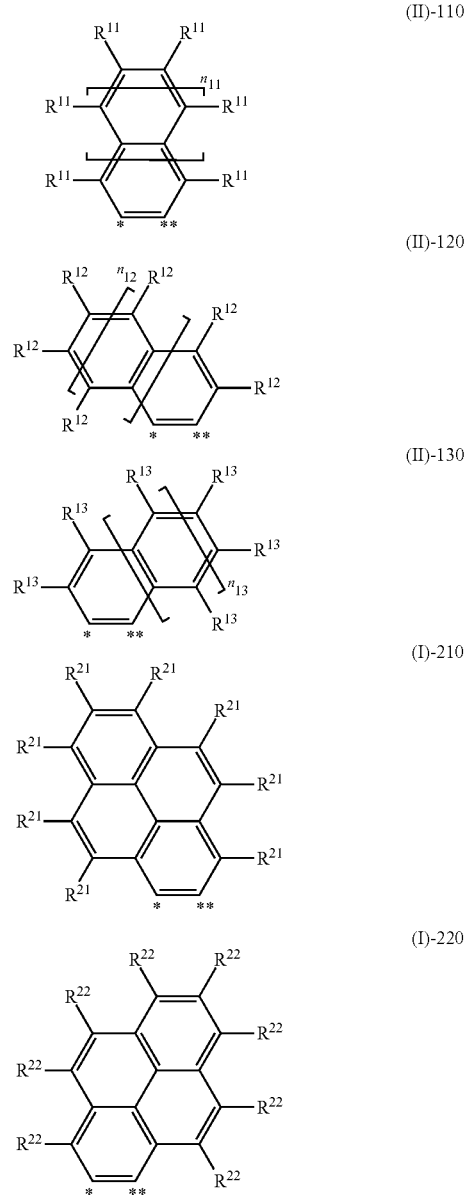

[Chem. 3]

(in the formulae, $R^1$ represents a hydrogen atom, an alkyl group, or an aryl group, and two $R^1$s may be the same as or different from each other;

$R^2$ represents a hydrogen atom or an alkyl group;

$R^{11}$, $R^{12}$, $R^{13}$, $R^{21}$, and $R^{22}$ each independently represent a hydrogen atom or an alkyl group, and a plurality of $R^{11}$s, $R^{12}$s, $R^{13}$s, $R^{21}$s, and $R^{22}$s may be the same as or different from one another;

when $n_{11}$ is an integer of 0, $R^{10}$ represents a hydrogen atom, an alkyl group, an alkenyl group, an alkynyl group, an aryl group, an alkyl carbonyl amino or a group represented by the following general formula (z)-10 or (z)-20, at least one of a plurality of $R^{10}$s is the group represented by the general formula (z)-10 and the plurality of $R^{10}$s may be the same as or different from one another;

when $n^{11}$ is an integer of 1 or 2, $R^{10}$ represents a hydrogen atom, an alkyl group, an alkenyl group, an alkynyl group, and aryl group, an alkyl carbonyl amino group, or a group represented by the general formula (z)-10 or (z)-20 and the plurality of $R^{10}$s may be the same as or different from one another;

$n_{12}$ and $n_{13}$ are each independently 1 or 2; and a plurality of $n_{11}$s, $n_{12}$s, and $n_{13}$s may be the same as or different from one another).

2. A compound represented by the following general formula (IA) or (IB),

[Chem. 4]

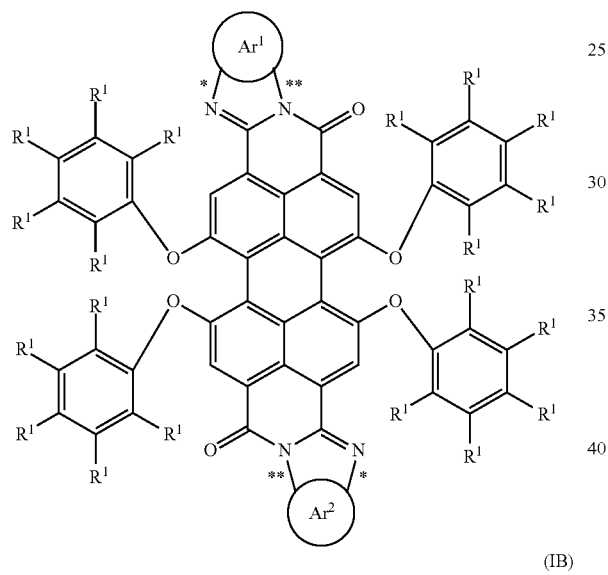

(IA)

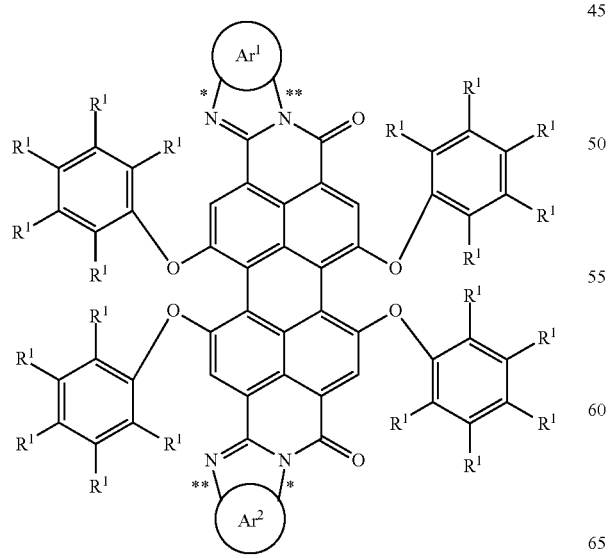

(IB)

(in the formulae, $R^1$ represents a hydrogen atom or an alkyl group, and a plurality of $R^1$s may be the same as or different from one another;

$Ar^1$ and $Ar^2$ each independently represent a group represented by the following general formula (I)-11, (I)-12, (I)-13, (I)-21, or (I)-22; and a bond marked with a symbol "*" is attached to a carbon atom marked with the symbol "*" of the group, and a bond marked with a symbol "" is attached to a carbon atom marked with the symbol "" of the group),

[Chem. 5]

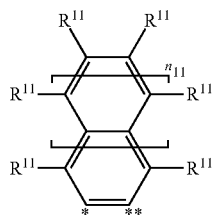

(I)-11

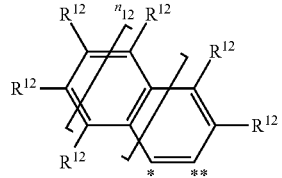

(I)-12

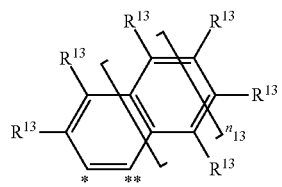

(I)-13

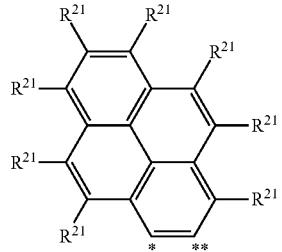

(I)-21

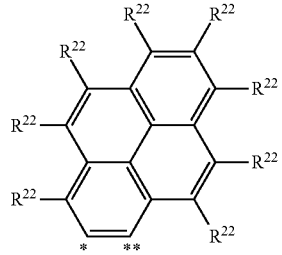

(I)-22

(in the formulae, $R^{11}$, $R^{12}$, $R^{13}$, $R^{21}$, and $R^{22}$ each independently represent a hydrogen atom or an alkyl group, and a plurality of $R^{11}$s, $R^{12}$s, $R^{13}$s, $R^{21}$s, and $R^{22}$s may be the same as or different from one another; and $n_{11}$, $n_{12}$, and $n_{13}$ are each independently 1 or 2, and a plurality of $n_{11}$s, $n_{12}$s, and $n_{13}$s may be the same as or different from one another).

3. The compound according to claim 2, wherein $R^1$, $R^{11}$, $R^{12}$, $R^{13}$, $R^{21}$, and $R^{22}$ each independently represent a hydrogen atom or an alkyl group having 1 to 22 carbon atoms.

4. The compound according to claim 3, wherein $R^1$, $R^{11}$, $R^{12}$, $R^{13}$, $R^{21}$, and $R^{22}$ each independently represent a hydrogen atom or an alkyl group having 6 to 18 carbon atoms.

5. A compound represented by the following general formula (IIA) or (IIB),

[Chem. 6]

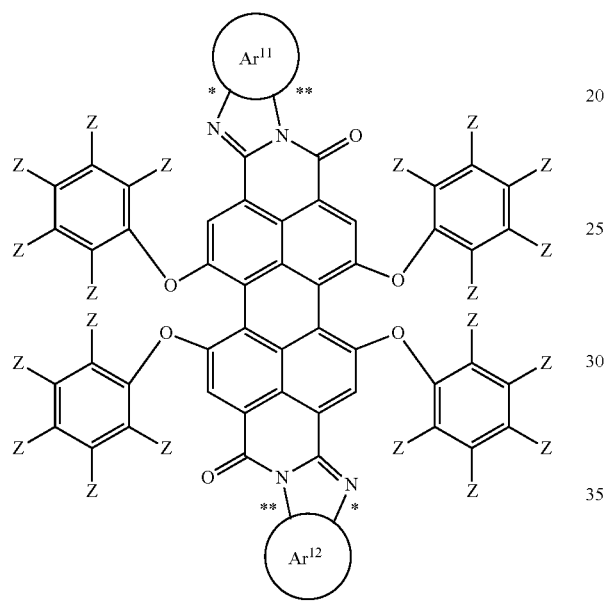

(IIA)

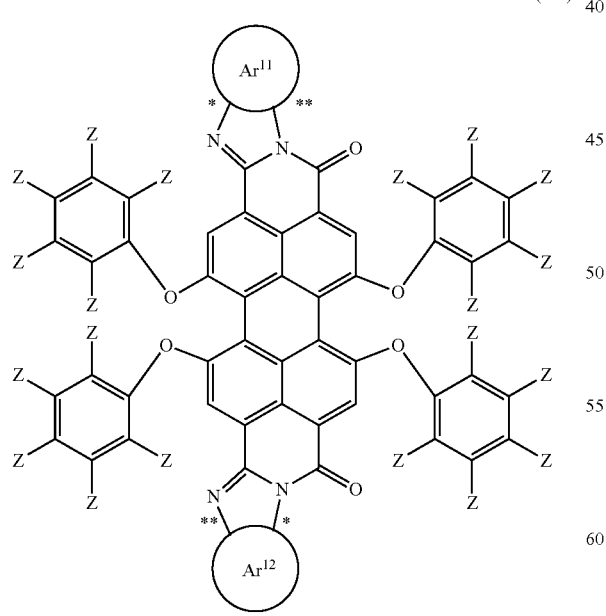

(IIB)

(in the formula, Z represents a hydrogen atom, an alkyl group, an alkenyl group, an alkynyl group, an aryl group, an alkyl carbonyl amino group, or a group represented by the following general formula (z)-1 or (z)-2, a plurality of Zs may be the same as or different from one another, and at least one Z represents an alkenyl group, an alkynyl group, an aryl group, an alkyl carbonyl amino group, or a group represented by the following general formula (z)-1 or (z)-2;

$Ar^{11}$ and $Ar^{12}$ each independently represent a group represented by the following general formula (II)-11, (II)-12, or (II)-13; and a bond marked with a symbol "*" is attached to a carbon atom marked with the symbol "*" of the group, and a bond marked with a symbol "" is attached to a carbon atom marked with the symbol "" of the group),

[Chem. 7]

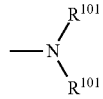

(Z)-1

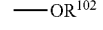

(Z)-2

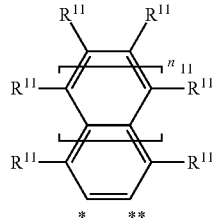

(II)-11

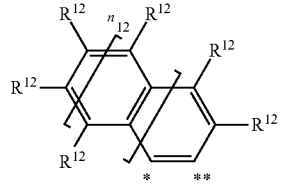

(II)-12

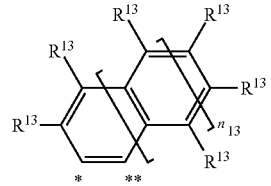

(II)-13

(in the formula, $R^{101}$ represents a hydrogen atom, an alkyl group, or an aryl group, and two $R^{101}$s may be the same as or different from each other;

$R^{102}$ represents a hydrogen atom or an alkyl group;

$R^{11}$, $R^{12}$, and $R^{13}$ each independently represent a hydrogen atom or an alkyl group, and a plurality of $R^{11}$s, $R^{12}$s, and $R^{13}$s may be the same as or different from one another;

when $n_{11}$ is an integer of 0,

Z represents a hydrogen atom, an alkyl group, and alkenyl group, an alkynyl group, an aryl group, an alkyl carbonyl amino or a group represented by the following general formula (z)-1 or (z)-2 at least one of a plurality of Zs is the group represented by the general formula (z)-1 and the plurality of Zs may be the same as or different from one another;

when $n_{11}$ is an integer of 1 or 2,

Z represents a hydrogen atom, an alkyl group, an alkenyl group, an alkynyl group, an aryl group, an alkyl carbonyl amino group, or a group represented by the general formula (z)-1 or (z)-2 and the plurality of Zs may be the same as or different from one another;

$n_{12}$ and $n_{13}$ are each independently 1 or 2; and a plurality of $n_{11}$s, $n_{12}$s, and $n_{13}$s may be the same as or different from one another).

6. The compound according to claim 5, wherein Z represents a hydrogen atom, an alkyl group having 1 to 22 carbon atoms, or a group represented by the general formula (z)-1 or (z)-2, $R^{101}$ represents a hydrogen atom, an alkyl group having 1 to 10 carbon atoms, or an aryl group having 6 to 12 carbon atoms, $R^{102}$ represents an alkyl group having 1 to 10 carbon atoms, and $R^{11}$, $R^{12}$, and $R^{13}$ each independently represent a hydrogen atom or an alkyl group having 1 to 22 carbon atoms.

7. The compound according to claim 5, wherein Z represents a hydrogen atom, an alkyl group having 6 to 18 carbon atoms, or a group represented by the general formula (z)-1 or (z)-2, and $R^{11}$, $R^{12}$, and $R^{13}$ each independently represent a hydrogen atom or an alkyl group having 6 to 18 carbon atoms.

8. A solar cell module which comprises the compound according to claim 1.

9. The solar cell module according to claim 8, comprising:

a light guide which includes a light incident surface and a light emitting surface whose area is smaller than that of the light incident surface; and a solar cell element which receives light emitted from the light emitting surface and generates power, wherein the light guide further contains the compound and uses, as the emitted light, radiation light from the compound that is generated by incident light on the light incident surface being absorbed by the compound.

10. A solar power generation device comprising the solar cell module according to claim 8.

* * * * *